United States Patent
Hennersperger et al.

(10) Patent No.: US 11,382,599 B2
(45) Date of Patent: Jul. 12, 2022

(54) ULTRASOUND IMAGING SYSTEM RECONSTRUCTING AN INTRAVASCULAR IMAGE USING ANGULAR POSITIONS OF A TRANSDUCER ARRAY

(71) Applicants: THE COLLEGE OF THE HOLY & UNDIVIDED TRINITY OF QUEEN ELIZABETH, Dublin (IE); National University of Ireland, Galway, Galway (IE)

(72) Inventors: Christoph Hennersperger, Bavaria (DE); Andrew Bourke, Dublin (IE); Fionn Lahart, Dublin (IE)

(73) Assignee: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 17/032,988

(22) Filed: Sep. 25, 2020

(65) Prior Publication Data
US 2021/0186457 A1     Jun. 24, 2021

Related U.S. Application Data

(63) Continuation of application No. 17/041,692, filed as application No. PCT/IB2019/000963 on Aug. 30, 2019.

(Continued)

(51) Int. Cl.
*A61B 8/08*      (2006.01)
*A61B 8/12*      (2006.01)

(Continued)

(52) U.S. Cl.
CPC .............. *A61B 8/12* (2013.01); *A61B 8/0883* (2013.01); *A61B 8/0891* (2013.01); *A61B 8/14* (2013.01);

(Continued)

(58) Field of Classification Search
USPC ......................................................... 600/443
See application file for complete search history.

(56) References Cited

U.S. PATENT DOCUMENTS

| 5,070,734 A | 12/1991 | Kawabuchi et al. |
| 5,313,949 A | 5/1994 | Yock |

(Continued)

FOREIGN PATENT DOCUMENTS

| WO | 2016/090175 A1 | 6/2016 |
| WO | 2020/044117 A2 | 3/2020 |

OTHER PUBLICATIONS

Grondin, J., Wan, E., Gambhir, A., Garan, H., & Konofagou, E. E. (2015). Intracardiac myocardial elastography in canines and humans in vivo. IEEE transactions on ultrasonics, ferroelectrics, and frequency control, 62(2), 337-349. (Year: 2015).*

(Continued)

*Primary Examiner* — Serkan Akar
*Assistant Examiner* — Renee C Langhals
(74) *Attorney, Agent, or Firm* — Brown Rudnick LLP; Adam M. Schoen

(57) ABSTRACT

A catheter-based ultrasound imaging system configured to provide a full circumferential 360-degree view around an intra-vascular/intra-cardiac imaging-catheter-head by generating a three-dimensional view of the tissue surrounding the imaging-head over time. The ultrasound imaging system can also provide tissue-state mapping capability. The evaluation of the vasculature and tissue characteristics include path and depth of lesions during cardiac-interventions such as abla- (Continued)

tion. The ultrasound imaging system comprises a catheter with a static or rotating sensor array tip supporting continuous circumferential rotation around its axis, connected to an ultrasound module and respective processing machinery allowing ultrafast imaging and a rotary motor that translates radial movements around a longitudinal catheter axis through a rotary torque transmitting part to rotate the sensor array-tip. This allows the capture and reconstruction of information of the vasculature including tissue structure around the catheter tip for generation of the three-dimensional view over time.

8 Claims, 32 Drawing Sheets

Related U.S. Application Data

(60) Provisional application No. 62/922,225, filed on Oct. 11, 2018, provisional application No. 62/725,655, filed on Aug. 31, 2018.

(51) Int. Cl.
| | |
|---|---|
| *A61B 8/00* | (2006.01) |
| *A61B 18/14* | (2006.01) |
| *A61B 8/14* | (2006.01) |
| *A61B 34/10* | (2016.01) |
| *A61B 18/00* | (2006.01) |
| *G06T 15/08* | (2011.01) |
| *A61B 17/00* | (2006.01) |

(52) U.S. Cl.
CPC .......... *A61B 8/4461* (2013.01); *A61B 8/4494* (2013.01); *A61B 8/466* (2013.01); *A61B 8/467* (2013.01); *A61B 8/483* (2013.01); *A61B 8/485* (2013.01); *A61B 8/5207* (2013.01); *A61B 8/5246* (2013.01); *A61B 8/54* (2013.01); *A61B 18/00* (2013.01); *A61B 18/1492* (2013.01); *A61B 34/10* (2016.02); *G06T 15/08* (2013.01); *A61B 2017/0011* (2013.01); *A61B 2018/00214* (2013.01); *A61B 2018/00351* (2013.01); *A61B 2018/00577* (2013.01); *A61B 2018/00904* (2013.01); *A61B 2034/102* (2016.02); *A61B 2034/107* (2016.02); *A61B 2562/04* (2013.01); *G06T 2210/41* (2013.01)

(56) References Cited

U.S. PATENT DOCUMENTS

| | | | |
|---|---|---|---|
| 5,485,846 | A | 1/1996 | Webler et al. |
| 5,699,805 | A | 12/1997 | Seward et al. |
| 5,752,518 | A | 5/1998 | McGee et al. |
| 5,846,204 | A | 12/1998 | Solomon |
| 6,503,199 | B1 | 1/2003 | Lennon |
| 9,901,321 | B2 | 2/2018 | Harks et al. |
| 2007/0073135 | A1 | 3/2007 | Lee et al. |
| 2010/0152590 | A1* | 6/2010 | Moore ................. A61B 8/4461 600/466 |
| 2012/0265069 | A1 | 10/2012 | Sliwa et al. |
| 2013/0102932 | A1 | 4/2013 | Cain et al. |
| 2014/0081262 | A1 | 3/2014 | Koblish et al. |
| 2014/0180273 | A1 | 6/2014 | Nair |
| 2014/0276084 | A1* | 9/2014 | Kemp ................. G01S 15/8918 600/467 |
| 2016/0157828 | A1 | 6/2016 | Sumi et al. |
| 2017/0120080 | A1 | 5/2017 | Phillips et al. |
| 2018/0199911 | A1 | 7/2018 | Harks et al. |
| 2019/0175035 | A1* | 6/2019 | Van Der Horst .... A61B 8/4477 |
| 2020/0214670 | A1* | 7/2020 | Ossmann ................. A61B 8/12 |

OTHER PUBLICATIONS

Grondin, 2015, Intracardiac mocardial elastography in canines and humans in vivo, IEEE Transactions on Ultrasonics, Ferroelectrics and Frequency Control, IEEE, US, 62(2):337-349.
International Preliminary Report on Patentability issued in International Patent Application No. PCT/IB2019/000963, dated Mar. 2, 2021, 21 pages.
International Search Report and Written Opinion issued in International Patent Application No. PCT/IB2019/000963, dated Jun. 17, 2020, 30 pages.
Montaldo, 2009, Coherent plane-wave compounding for very high frame rate ultrasonography and transient elastography, IEEE Transactions on Ultrasonics, Ferroelectrics and Frequency Control, IEEE, US, 56(3):489-506.
Nikolov, 2002, Three-Dimensional Real-Time Synthetic Aperture Imaging Using a Rotating Phased Arra Transducer, IEEE Ultrasonics Symposium Proceedings, Muenchen, Germany, 1585-1588.

* cited by examiner

1702 — ANGULAR DISTANCE BETWEEN SLICES (19.2 kHz 2D ACQUISITION RATE) [mm]

| REVOLUTION SPEED [rpm] | \ | DEPTH [mm] | | | | | | | | | |
|---|---|---|---|---|---|---|---|---|---|---|---|
| | | 0.5 | 5 | 10 | 15 | 20 | 25 | 30 | 35 | 40 | 45 |
| 600 | | 0.00 | 0.01 | 0.02 | 0.02 | 0.03 | 0.04 | 0.05 | 0.06 | 0.07 | 0.07 |
| 1200 | | 0.00 | 0.02 | 0.03 | 0.05 | 0.07 | 0.08 | 0.10 | 0.11 | 0.13 | 0.15 |
| 1800 | | 0.00 | 0.02 | 0.05 | 0.07 | 0.10 | 0.12 | 0.15 | 0.17 | 0.20 | 0.22 |
| 2400 | | 0.00 | 0.03 | 0.07 | 0.10 | 0.13 | 0.16 | 0.20 | 0.23 | 0.26 | 0.29 |

1704 — NUMBER OF PLANES CONSIDERED DEPENDING ON BEAM THICKNESS (1200 rpm ROTATIONAL SPEED)

| BEAM THICKNESS [mm] | \ | DEPTH [mm] | | | | | | | | | |
|---|---|---|---|---|---|---|---|---|---|---|---|
| | | 0.5 | 5 | 10 | 15 | 20 | 25 | 30 | 35 | 40 | 45 |
| 0.5 | | 305.58 | 30.56 | 15.28 | 10.19 | 7.64 | 6.11 | 5.09 | 4.37 | 3.82 | 3.40 |
| 1 | | 611.16 | 61.12 | 30.56 | 20.37 | 15.28 | 12.22 | 10.19 | 8.73 | 7.64 | 6.79 |
| 2.5 | | 1527.89 | 152.79 | 76.39 | 50.93 | 38.20 | 30.56 | 25.46 | 21.83 | 19.10 | 16.98 |
| 5 | | 3055.78 | 305.58 | 152.79 | 101.86 | 76.39 | 61.12 | 50.93 | 43.65 | 38.20 | 33.95 |

FIG. 17

ANGULAR DISTANCE BETWEEN TWO ROTATIONAL SLICES TO TRACK SHEAR WAVE IN 3D

| | | SHEAR WAVE SPEED [mm/ms] | | | | | | | |
|---|---|---|---|---|---|---|---|---|---|
| | | 0.5 | 1 | 1.5 | 2 | 2.5 | 3 | 3.5 | 4 | 4.5 | 4 |
| ANGULAR DISTANCE | 10 | 2.9° | 5.7° | 8.6° | 11.5° | 14.4° | 17.3° | 20.2° | 23.1° | 26.0° | 29.0° |
| | 20 | 1.4° | 2.9° | 4.3° | 5.7° | 7.2° | 8.6° | 10.0° | 11.5° | 12.9° | 14.4° |
| | 30 | 1.0° | 1.9° | 2.9° | 3.8° | 4.8° | 5.7° | 6.7° | 7.6° | 8.6° | 9.6° |
| | 40 | 0.7° | 1.4° | 2.1° | 2.9° | 3.6° | 4.3° | 5.0° | 5.7° | 6.4° | 7.2° |

EQUIVALENT ROTATIONAL SPEED IN REVOLUTIONS PER MINUTE (RPM)

| | | SHEAR WAVE SPEED [mm/ms] | | | | | | | |
|---|---|---|---|---|---|---|---|---|---|
| | | 0.5 | 1 | 1.5 | 2 | 2.5 | 3 | 3.5 | 4 | 4.5 | 4 |
| ANGULAR DISTANCE | 10 | 478 | 955 | 1434 | 1913 | 2394 | 2876 | 3360 | 3846 | 4334 | 4826 |
| | 20 | 239 | 478 | 716 | 955 | 1194 | 1434 | 1673 | 1913 | 2153 | 2394 |
| | 30 | 159 | 318 | 478 | 637 | 796 | 955 | 1115 | 1274 | 1413 | 1593 |
| | 40 | 119 | 239 | 358 | 478 | 597 | 716 | 839 | 955 | 1075 | 1194 |

FIG. 22

ULTRASOUND IMAGING SYSTEM RECONSTRUCTING AN INTRAVASCULAR IMAGE USING ANGULAR POSITIONS OF A TRANSDUCER ARRAY

CROSS-REFERENCE TO RELATED APPLICATIONS

This application is a continuation of U.S. Nonprovisional patent application Ser. No. 17/041,692, filed Sep. 25, 2020, which is a national stage entry of PCT/IB2019/000963 with an International Filing Date of Aug. 30, 2019, which claims the benefit of U.S. Nonprovisional patent application Ser. No. 16/157,465, filed Oct. 11, 2018 and U.S. Provisional Application No. 62/725,655, filed Aug. 31, 2018, the content of each of which are hereby incorporated by reference in their entireties.

FIELD OF THE DISCLOSURE

The present disclosure relates to systems and methods for visualization and characterization of human tissue using three-dimensional ultrasound monitoring. Specifically, the present disclosure relates to visualization and monitoring of the completeness of ablation of tissue during ablation and similar procedures using the disclosed tissue characterization methods.

BACKGROUND

In typical ultrasound systems configured to visualize inner body regions, dynamic forces are often employed, resulting in a dynamic movement of the body regions over time. These dynamic forces and movements make it difficult to stabilize internal imaging devices and generate consistent and accurate images if imaging of the structure cannot be enabled in real-time (e.g., >20 Hz). As a result, the captured images often lack the necessary quality required to prescribe appropriate treatment or therapy, and internal real-time imaging is limited to small two-dimensional areas or three-dimensional volumetric regions respectively. In addition, typical ultrasound systems are configured in such a way that tissue and anatomic structures tend to change the spacing or even contact the image acquisition element making the images difficult to analyze. External imaging modalities are also available for imaging but these modalities have their own shortcomings. For example, some subjects have negative reactions to X-ray imaging, or contrast agents introduced into the subject; Magnetic Resonance Imaging (MRI) requires extensive acquisition protocols impractical for intra-operative use; and external ultrasound systems can only visualize inner body regions and structures with well-controlled positioning of the body.

Fluoroscopy as imaging modality employing X-Ray to display moving images of the body is the common practice for performing ablation procedures in the heart or other locations within the vasculature. In endocardial ablation procedures, Fluoroscopy is used in conjunction with mapping systems, visualizing the position and orientation of catheters in relation to extracted anatomical models, and also displaying electrical activity overlaid with said anatomical models. Both Fluoroscopy and mapping systems are generally used to identify anatomic landmarks within the heart and locate the position of the ablation electrode or electrodes relative to the targeted ablation site. However, Fluoroscopy and mapping systems often fail to identify these anatomic sites. Furthermore, Fluoroscopy and mapping systems do not detect whether the desired lesion pattern has been created after one or multiple ablations in the target anatomical position. Instead, determining whether the lesion characteristics are as intended is inferred based upon empirical measurements of the applied ablation power, tissue temperature, and ablation time. Furthermore, Fluoroscopy is not able to distinguish between infarcted tissue and normal tissue, thereby making is difficult to assess the success of the procedure during the intervention.

Innovations in this area have offered many solutions to address the aforementioned drawbacks. For example, McGee et al. (U.S. Pat. No. 5,752,518) teaches a system for stabilizing a sensor inside the vasculature. However, McGee's system is unable to identify the depth of the ablation of the tissue. As a result, the solution provided in McGee makes it difficult to determine the success of the procedure even when the visible surface ablation regions are identifiable as complete. As another example, Koblish et al. (U.S. Patent Pub. No. 2014/0081262) discloses a system for depth of ablation evaluation; however, the system is limited to nearfield ultrasound and one-dimensional (forward-looking) evaluation only. As another example, Harks et al. (U.S. Pat. No. 9,901,321) describes a system for ablation evaluation that uses direct ultrasound intensities.

SUMMARY

In accordance with one aspect of the invention, an ultrasound imaging system is disclosed that includes a catheter comprising: a catheter tip, the catheter tip having an ultrasound transducer array comprising ultrasound transducers in the form of ultrasound transmitters and sensors within an acoustic housing; a catheter body configured for electrical, mechanical and rotational connection of the ultrasound transducers; and a catheter shaft configured to transfer both rotational and electrical signals to the ultrasound transducer array; and a console comprising: a rotary motor connected via the catheter shaft to the ultrasound transducer array to enable a rotation or a positioning of the ultrasound transducer array within the acoustic housing such that the ultrasound transducer array captures data continuously over a 360 degree angle circumferentially around the catheter tip; an ultrasound module electrically connected through the catheter shaft and the catheter body to the ultrasound transducer array; and an imaging workstation comprising a server, the imaging workstation coupled to the ultrasound module, the imaging workstation configured to provide a processing power and storage capability to the ultrasound module to process captured anatomical imaging data and functional imaging for tissue parameter extraction data from the ultrasound transducer array to generate two, three or four dimensional images from the data and enable display of the two, three or four dimensional images with interactive display manipulation.

The ultrasound transmitters and sensors may comprise a plurality of piezo-electric transducers configured to transmit ultrasound pulses and receive an echo of the ultrasound pulses with all piezo-electric transducers in parallel.

The catheter tip further may further comprise control elements configured to enable at least one of steering, tracking and rotating the plurality of ultrasound transducer array of the catheter tip.

The catheter body may comprise an outer sheath; a connector configured to couple to the ultrasonic transducer array; a first concentric catheter in the outer sheath, wherein the first concentric catheter is connected to the ultrasound transducer array and to the connector such that the first concentric catheter is rotatable from outside the catheter tip and is configured to rotate the ultrasound transducer array within the acoustic housing in the catheter tip; and a second concentric catheter comprising internal electrical wiring to electrically connect the ultrasound transducer array in full (i.e. each transducer element) to the connector and to the acoustic housing.

The ultrasound module may be configured to determine and control rotation of the ultrasound transducer array and firing of ultrasound pulses by the ultrasound transmitters in the ultrasound transducer array, supporting ultrafast imaging (planewave, diverging wave) along conventional scanline imaging The ultrasound module in combination with the imaging work station may be configured to schedule a firing sequence of ultrasound pulses by the ultrasound transmitters in the ultrasound transducer array and to process a collected reflected ultrasound data by the sensors in the ultrasound transducer array to produce the two, three or four dimensional images.

The ultrasound module in combination with the imaging work station may generate static or rotation corrected slice-based images from data collected by the sensors in the ultrasound transducer array.

The ultrasound module in combination with the imaging work station may be configured to generate volume-based images from the data collected by the sensors in the ultrasound transducer array.

The ultrasound sensor array tip may be static and the angular rotation may be accomplished by software.

Grayscale anatomical data (e.g. B-mode) may be captured using ultrafast imaging data.

Tissue functional imaging may be used to capture the elastic imaging for tissue parameter extraction data.

The imaging workstation may be further configured to extract tissue characterization and visual confirmation to determine completeness of ablation procedures over the surface of target tissue and depth of tissue.

The imaging workstation may be further configured to display at least one of anatomical images, functional images, and combined images from the captured anatomical imaging data and elastic imaging for tissue parameter extraction data.

The imaging workstation may be further configured to perform multi-mode imaging.

The displayed images may enable monitoring and verification of accuracy and completeness of ablation procedures while ultrasound imaging and ablation procedures are being performed.

In accordance with another aspect of the invention, a method to re-construct and visualize a slice-based image is disclosed that includes retrieving image data collected and stored in a database; consolidating channel data for single image sequence from brightness mode and functional tissue imaging based on the retrieved image data; reconstructing at least one of a two, a three or a four-dimensional image using the consolidated channel (echo) data; and outputting the at least one of the two, the three or the four-dimensional image to a display.

In accordance with a further aspect of the invention, a method to re-construct and visualize a volume-based image is described that includes retrieving image data collected and stored in a database; consolidating channel data for a single firing pattern from anatomical and functional tissue imaging based on the retrieved ultrasound echo data; reconstructing at least one of a three- or four-dimensional image using the consolidated channel data using an ultrasound imaging system; and outputting the at least one of the three- or four-dimensional image to a display.

In accordance with yet another aspect of the invention, an imaging system for real time control and verification of procedures in the vasculature is disclosed that includes: a catheter comprising a proximal end and a distal end, the distal end of the catheter comprising a catheter tip, the catheter tip comprising an ultrasound transducer array enclosed within an acoustic housing, wherein the distal end of the catheter is configured to be inserted into and guided to a site of a procedure in a vasculature, and wherein the ultrasound transducer array is rotatable within the acoustic housing while transmitting ultrasound pulses and receiving ultrasound echoes from the surrounding vasculature; and a console coupled to the catheter, the catheter comprising an embedded ultrasound module and an imaging workstation with a processor and storage capability, wherein the console is enabled for planning ultrasound imaging data capture, providing synchronized rotational and pulsing control to the ultrasound transducer array, and for receiving, consolidating and processing data captured from the received ultrasound echoes by the ultrasound transducer array to generate tissue image data and tissue characterization data for the vasculature surrounding the catheter tip at the site of the procedure, and wherein the imaging workstation is further configured to display at least a two, a three or a four-dimensional image of at least one of the received and processed tissue image data and tissue characterization data of the vasculature at the site of the procedure on a display for interactive and real-time control and verification of the procedure in the vasculature.

The imaging system may be attached to a procedural catheter or a procedural instrument for the real-time control and in-situ verification of the procedure as the procedures are being executed within the vasculature.

A method for ultrasound imaging using an imaging system including (i) a catheter comprising a proximal end and a distal end, the distal end of the catheter comprising a catheter tip, the catheter tip comprising an ultrasound transducer array enclosed within an acoustic housing and extending along a longitudinal axis of the catheter, wherein the distal end of the catheter is configured to be inserted into and guided to a site of a procedure in a medium, and wherein the ultrasound transducer array is rotatable within the acoustic housing while transmitting ultrasound pulses and receiving ultrasound echoes from the surrounding medium, and (ii) a controller communicatively coupled with the catheter, the method comprising: circumferentially rotating the catheter including the array of acoustic transducers about a longitudinal axis of the catheter; while rotating the catheter: transmitting, by the array of acoustic transducers at a set of different transmission angular positions, a plurality of incident acoustic wave signals representative of one or more plane waves in a volume of observation of the medium, receiving, by the array of acoustic transducers at a set of different reception angular positions, a plurality of reflected signals, wherein each of the plurality of reflected signals corresponds to one of the plurality of incident acoustic wave signals reflected by the medium, wherein at least one of the plurality of reflected signals is received by the array of acoustic transducers at a reception angular position that is different than the transmission angular position of the corresponding transmitted incident acoustic wave signal; and generating an image of the medium as a function of at least: the plurality of reflected signals, and for at least one of the respective reflected signals: (a) the transmission angular position of each of the acoustic transducers for the incident acoustic wave signal that corresponds to the respective reflected signal and (b) the reception angular position of each of the acoustic transducers for the respective reflected signal, wherein the reception angular position of the acoustic transducers for the respective reflected signal is different than the transmission angular position of the acoustic transducers for the respective reflected signal.

A method for ultrasound imaging using an imaging system including (i) a catheter comprising a proximal end and a distal end, the distal end of the catheter comprising a catheter tip, the catheter tip comprising an ultrasound transducer array enclosed within an acoustic housing and extending along a longitudinal axis of the catheter, wherein the distal end of the catheter is configured to be inserted into and guided to a site of a procedure in a medium, and wherein the ultrasound transducer array is rotatable within the acoustic housing while transmitting ultrasound pulses and receiving ultrasound echoes from the surrounding medium, and (ii) a controller communicatively coupled with the catheter, the method comprising: before an ablation procedure, circumferentially rotating the catheter including the array of acoustic transducers about a longitudinal axis of the catheter; while circumferentially rotating the catheter: transmitting, by an array of acoustic transducers, a plurality of pre-ablation incident acoustic wave signals representative of angled plane waves in an area of observation of the medium, receiving, by an array of acoustic transducers, a plurality of pre-ablation reflected signals, wherein each of the plurality of pre-ablation reflected signals corresponds to one of the plurality of pre-ablation incident acoustic wave signals reflected by the medium, wherein the plurality of pre-ablation reflected signals includes raw radio-frequency (i.e., directly after analog to digital conversion (minimal processing)) data represented in time domain; and after the ablation procedure, circumferentially rotating the catheter including the array of acoustic transducers about a longitudinal axis of the catheter; while circumferentially rotating the catheter: transmitting, by an array of acoustic transducers, a plurality of post-ablation incident acoustic wave signals representative of angled plane waves in an area of observation of the medium, receiving, by an array of acoustic transducers, a plurality of post-ablation reflected signals, wherein each of the plurality of post-ablation reflected signals corresponds to one of the plurality of post-ablation incident acoustic wave signals reflected by the medium, wherein the plurality of post-ablation reflected signals includes raw radio-frequency data represented in a time domain; and generating an image of the medium, including: for each pixel of the image: identifying a portion of the pre-ablation reflected signals that corresponds to the respective pixel and transforming the portion of the pre-ablation reflected signal from a time domain representation to a frequency domain representation; identifying a portion of the post-ablation reflected signals that corresponds to the respective pixel and transforming the portion of the post-ablation reflected signal from a time domain representation to a frequency domain representation; generating a lesion-spectral-change value by comparing the portion of the pre-ablation reflected signals in the frequency domain to the portion of the post-ablation reflected signals in the frequency domain.

A method for ultrasound imaging of a medium including a shear wave using an imaging system including (i) a catheter comprising a proximal end and a distal end, the distal end of the catheter comprising a catheter tip, the catheter tip comprising an ultrasound transducer array enclosed within an acoustic housing and extending along a longitudinal axis of the catheter, wherein the distal end of the catheter is configured to be inserted into and guided to a site of a procedure in a medium, and wherein the ultrasound transducer array is rotatable within the acoustic housing while transmitting ultrasound pulses and receiving ultrasound echoes from the surrounding medium, and (ii) a controller communicatively coupled with the catheter, the method comprising: determining a shear wave propagation speed of the shear wave; circumferentially rotating the catheter including the array of acoustic transducers about a longitudinal axis of the catheter at a catheter rotation speed, wherein the catheter rotation speed is based on the shear wave propagation speed; while circumferentially rotating the catheter: transmitting, by the array of acoustic transducers, a plurality of incident acoustic wave signals representative of one or more plane waves in an volume of observation of the medium, receiving, by the array of acoustic transducers, a plurality of reflected signals, wherein each of the plurality of reflected signals corresponds to one of the plurality of incident acoustic wave signals reflected by the medium; and generating one or more images of the medium including one or more observations of the shear wave based on the plurality of reflected signals.

Additional features and advantages of the disclosure will be set forth in the description that follows, and in part, will be obvious from the description; or can be learned by practice of the principles disclosed herein. The features and advantages of the disclosure can be realized and obtained by means of the instruments and combinations particularly pointed out in the appended claims. These and other features of the disclosure will become fully apparent from the following description and appended claims, or can be learned by the practice of the principles set forth herein.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings.

FIG. 17 are tables of angular distance between frames and number of planewave transmits used for 3D compounding, in accordance with one embodiment of the present invention.

FIG. 22 is a table of shear wave speed, in accordance with one embodiment of the present invention.

DETAILED DESCRIPTION

Figure 1:
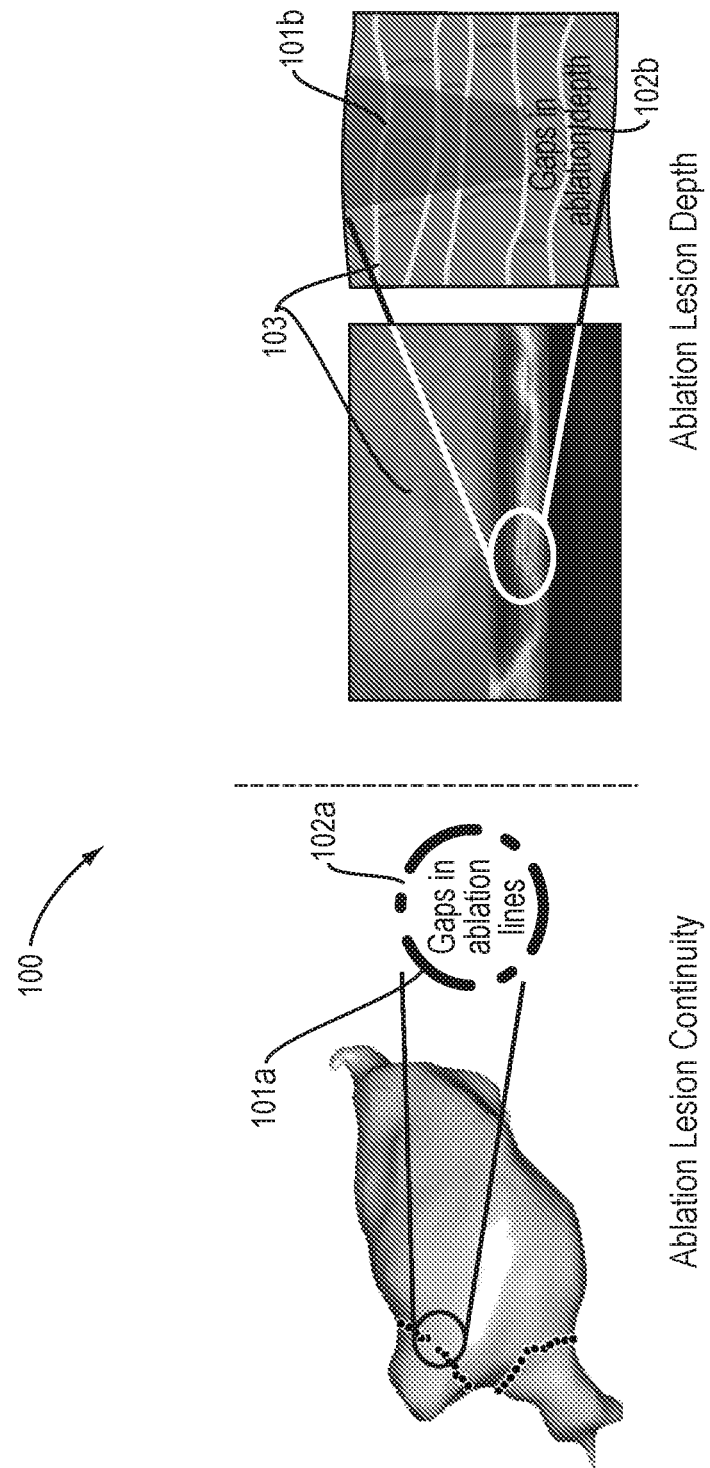
FIG. 1 is prior art that schematically depicts a human tissue undergoing a conventional atrial fibrillation treatment.

Embodiments will be described below in more detail with reference to the accompanying drawings. The following detailed descriptions are provided to assist the reader in gaining a comprehensive understanding of the methods, apparatuses, and/or systems described herein and equivalent modifications thereof. Accordingly, various changes, modifications, and equivalents of the methods, apparatuses, and/or systems described herein will be apparent to those of ordinary skill in the art. Moreover, descriptions of well-known functions and constructions may be omitted for increased clarity and conciseness.

The terms used in the description are intended to describe embodiments only, and shall by no means be restrictive. Unless clearly used otherwise, expressions in a singular from include a meaning of a plural form. In the present description, an expression such as "comprising" or "including" is intended to designate a characteristic, a number, a step, an operation, an element, a part or combinations thereof, and shall not be construed to preclude any presence or possibility of one or more other characteristics, numbers, steps, operations, elements, parts or combinations thereof.

Embodiments of the invention are directed to providing very high reliability real-time monitoring and control capability for treatment of problems of the vasculature. Specifically, embodiments of the invention are directed to real time monitoring for completeness of tissue ablation that include depth of ablation along a desired path during treatment of atrial fibrillation (AF) using ultrasound scanning.

Embodiments of the invention address the advantages and features of the use of multi-sensor acoustic/ultrasound system capable of three-dimensional scanning of the vasculature over time to generate and capture data that allows extraction of three-dimensional images of the surfaces, three-dimensional characterization of tissue depth, and specific three-dimensional tissue characteristics such as tissue state or stiffness.

Embodiments of the invention use unique imaging protocols to process collected data to extract anatomical and functional information, and tissue characteristics and evaluate completeness of ablation around the origin of the electrical signal to the appropriate depth.

Embodiments of the invention are directed to a catheter-based ultrasound imaging system (UIS) that provides a full circumferential 360-degree view around an intra-vascular/intra-cardiac imaging-catheter-head by generating a three-dimensional view of the tissue surrounding the imaging-head over time (e.g. throughout cardiac pulse phase). The UIS also provides tissue-state mapping capability. The evaluation of the vasculature and tissue characteristics using the UIS include both the anatomical depiction of the vasculature, as well as information about the path and depth of lesions during cardiac interventions such as ablation. The UIS comprises a catheter with a static or rotating ultrasound transducer array comprising ultrasound transmitters and sensors connected to an ultrasound module and respective processing machinery and a rotary motor that translates radial movements around a longitudinal catheter axis through a rotary torque transmitting part, such as an inner catheter or a torque wire inside the catheter, to rotate the ultrasound transducer array comprising ultrasound transmitters and sensors. Further to this the UIS supports a continuous rotation around its axis providing a full circumferential (360-degree) coverage around the catheter, which in combination with ultrafast imaging techniques enables real-time volumetric imaging. This allows the capture and reconstruction of information of the vasculature including tissue structure around the catheter tip for generation of the three-dimensional view over time. The imaging system when combined with procedural tips, such as ablation electrode tips, both irrigated and non-irrigated, used in ablation procedures in the vasculature; location and tracking electrodes in the distal end of the catheter tip for electromagnetic localization of the catheter; or electro-anatomical mapping electrode tips used for sensing electrical signals and conduction paths in the heart etc. allows for in-situ evaluation of procedures as they happen. The described rotating imaging tip can be considered as a defined active imaging section of the catheter, and can be integrated proximal to another active section (as described) or distal to the other active section for 2D or 3D image capture of an area of interest as described in further detail hereinafter.

Through continuously rotating the catheter circumferentially around its axis (360-degree rotation without requiring to stop the catheter motion or move back and forth), both anatomical and functional imaging of tissue can be retrieved in real-time from the target anatomy.

a) Functional imaging may refer to protocols and processing methods to allow for the extraction of tissue parameters describing the specific function of tissue. Thereby, the function of tissue can be characterized for example as healthy tissue (muscle fibers, fat, etc.), scar tissue (necrosis), oedema, and etc. However, clinically it is important to note that tissue function can be gradual with respect to the state of the tissue to be examined, and may also be characterized by various markers (e.g. tissue stiffness, scatterer spectral properties, anisotropy). Examples for functional parameters are tissue stiffness or elasticity (as described in more detail in FIG. 2-3 and FIG. 21-23), tissue anisotropy (directionality), specific statistic tissue parameters such as being modeled by statistic distributions (Rayleigh, Nakagami), speed of sound in the tissue (modeling the density), textural parameters, spectral parameters (frequency-specific reflection and attenuation of tissue as described in more detail below in FIG. 18-20), and etc. This list is indicative. Functional imaging can comprise either single acquisition protocols, or a plurality of acquisition protocols and acquisition times.

b) Anatomical imaging may relate to specific data generated by imaging protocols and processing methods that primarily aim at depicting the spatial/geometrical relationship of tissue. One example in ultrasound imaging would be a grayscale-like representation of received ultrasound echoes (i.e. brightness mode), which shows tissue interfaces such as vessel walls by evaluating the intensity of reflected ultrasound echoes.

Imaging in general relates to the acquisition of signal intensities over time by using specific acquisition protocols. This can be in the form of 1D, 2D, or 3D imaging over time (1D+t, 2D+t, 3D+t). Considering time spatial dimension as commonly performed in ultrasound imaging, this relates to 2D, 3D, and 4D information. By combining multiple acquisitions protocols, complementary information can be acquired for each sample in 2D (1D+T), 3D (2D+t), and 4D (3D+t)

Embodiments of the invention provide for a three-dimensional visualization and tissue characterization system for use in minimally invasive procedures in the vasculature. Though the system and methods described are general and usable in treatment of problems of the vasculature, it is especially useful in the treatment of Atrial Fibrillation (AF) and other cardiac disorders as well as endovascular procedures for which the catheter system is designed to. In the following, the system and application are explained in detail with an AF treatment focus, but can be directly employed also for ventricular tachycardia, and general lesion monitoring such as in the denervation of renal arteries, as examples application in field outside of cardiac procedures.

AF is a disease that affects over 1% of the global population. As the population gets older, the probability of AF increases. Today the incidence of AF globally is over 33 million and increasing. Of all the treated patients only about 53% get relief after the first ablation procedure and this number can increase to about 80% after multiple procedures. This lack of monitoring and control of the procedure even with the advanced systems for treatment and current monitoring method leave much to be desired to establish effectiveness of the treatment.

In view of the foregoing, embodiments disclosed herein are directed to a three-dimensional visualization and tissue characterization system to be implemented in vasculature procedures. While the disclosure teaches implementing the system in atrial fibrillation (AF), it should be understood that the present embodiments can be implemented in other vasculature treatments such as cardiac disorders and endovascular procedures. The disclosed system can also be implemented for ventricular tachycardia, and general lesion monitoring. For example, some general lesion monitoring can include denervation of renal arteries.

Atrial Fibrillation

AF is an irregular heart beat caused by electrical signals originating in the atrial chambers of the heart which disrupts the regular rhythm of the beating heart. AF is treated by isolating the origin of these electrical signals and limiting their transmission by ablation of the cells that surround the location of origin and conduct the electrical impulse. The current catheter-based visualization and monitoring systems are only partially effective in identifying complete ablation through the thickness of the tissue (transmural ablation) to prevent re-establishment of conductive paths. As a result, they do not provide a sufficient solution for differentiating partial or temporal electric block from a permanent one.

FIG. 1 shows prior art that schematically depicts a human tissue undergoing a conventional AF treatment 100. The conventional AF treatment 100 illustrates incomplete ablation that often occurs in the conventional treatment due to a lack of control of the ablation. Two types of incomplete ablation often occur. For the purposes of this example, surface ablation is illustrated as 101*a* and the depth of ablation is illustrated as 101*b*. The discontinuity of ablation lesion is illustrated as 102*a* with respect to the surface ablation 101*a*. The incomplete ablation in the thickness of the wall of the left atrium (LA) is illustrated as 102*b* with respect to the depth of ablation 101*b*. In any ablation procedure, if the ablation is incomplete, there is a risk of reconnection of the electrical paths that result in recurrence of AF. As a result, these discontinuities in ablation can result in re-establishment of electrical paths that result in AF recurrence.

The wall thickness of the atrium of the heart can vary from 0.4 to 4.4 mm based on the patient population and reaches up to 10 mm in the ventricles. To provide complete ablation of the tissue, this variation in tissue thickness has to be considered without exceeding or damaging the organs around the heart. This requires an accurate monitoring of the depth of ablation. The present disclosure provides reconstruction of the tissue parameters for tissue characterization, with anatomical information. As a result, the anatomical image information is reconstructed from ultrasound image data received.

The present application is able to accomplish tissue reconstruction by capturing data related to the extraction of perfusion, stiffness, strain, anisotropy, coherence, specific statistical distributions in tissue (Rayleigh, Nakagami), spectral parameters of tissue (frequency power spectrum) and other parameters. This data can be captured using a rotating three-dimensional multi-element ultrasound transducer array. Data can be captured either a single point in time, or at different stages of the ablation procedure. The captured data can be processed using the disclosed imaging protocols to extract anatomical and functional information, and tissue characteristics. The extracted anatomical and functional information, and tissue characteristics can be used to evaluate the completeness of ablation around the origin of the signal to the appropriate depth and closed path. This provides evidence-based control of ablation to ensure completeness and success of treatment of AF.

Imaging Protocols

The disclosed imaging protocols and algorithms are used to reconstruct the functional tissue parameters of an organ of interest. For the purposes of this disclosure, the imaging protocols and algorithms are used to reconstruct functional tissue parameters of a heart; however, it should be understood other organs can be reconstructed using the process disclosed herein. The protocols and algorithms typically used exploit some of the special characteristics of the organ being verified.

As an initial matter, the strain of the heart muscles can be tracked by capturing the physiological movement of the heart using cardiac strain elastography. The multi-sensor ultrasound system disclosed is able to acquire the movement of the walls of the atrium through a cardiac contraction cycle. The imaging protocols and algorithms can generate a two-dimensional image of a selected region, a sub-volumetric three-dimensional image or a full three-dimensional volumetric image around the catheter. As a result, scatter displacement and tissue deformation can be tracked using the three-dimensional image or scatter within a two-dimensional plane to identify stress-based differentiation through the depth of the left atrium wall.

Micro-perfusion of blood in the atrium walls can be tracked over time using Ultrafast-Doppler effects to identify and reconstruct strain and general tissue motion. This tracking can be accomplished by capturing the signals, filtering out the strong signals related to the blood flow around the catheter, and performing micro-Doppler reconstruction. Micro-Doppler reconstruction can be accomplished using, for example, a modified autocorrelation technique to retrieve the micro-profusion values in the regions of interest.

By implementing multiple configurable ultrasound transmitters using an ultrasound transducer array, the disclosed system is able to produce strong acoustic pushes to specific target areas by focusing the transmitted energy. As a result, data can be collected to generate intra-cardiac slice-based imaging using the rotation of the ultrasound transducer array around the catheter location. This technique uses a capability similar to shear wave elastography (SWE) but in three dimensions to reconstruct the tissue parameters of the areas of interest of the atrium and is discussed in further detail below with respect to FIGS. 7-9 and 21-23.

The statistic and spectral properties of reflected ultrasound signals are evaluated within the desired spatial regions from a series of ultrafast acquisitions. This is accomplished by capturing signals from different angular acquisitions (using either emitted plane-waves or focused ultrasound beams as imaging protocols) and over a defined frequency range (multiple transmit frequency acquisitions with receive frequency filters). Furthermore, backscattered and coherence statistics are reconstructed to retrieve the spatial coherence and specific statistical values (e.g. Nakagami or Rayleigh distribution parameters) or the frequency distribution (spectral fit, frequency power spectrum, offer referred to as quantitative ultrasound) in the regions of interest in relation to different angular acquisitions, as discussed in greater detail with respect to FIGS. 7-9 and FIGS. 18-20.

The different processes discussed above can be integrated with a machine-learning based estimation of parameters. Specifically, the specific imaging protocols described are combined with a dedicated acquisition of specific training and test data to derive a specific machine-learning architecture (using e.g. decision trees and forests or a deep learning architecture such as convolutional or recurrent neural networks) to enable fast analysis of data and extraction of results.

It should also be understood that the final retrieval of tissue parameters eventually can include a combination of one or more methods described above. In this way, the final retrieval of tissue parameters can improve the robustness and specificity of retrieved tissue parameters. The disclosed system is able to acquire a 360-degree volumetric image of the vasculature and surrounding tissue or a subsection thereof. This 360-degree volumetric image can include an image of the walls of the atria, and the depth into the wall of the atria. This enables the system to collect tissue information. The data acquisition can be further refined by focusing the ultrasound beam to cover specific regions within the atria. The data collected is integrated to generate two- and three-dimensional image of the vasculature of interest. The tissue state mapping or functional imaging is performed by integration of the tissue data with the appropriate imaging protocols and reconstruction algorithms, as described above. These individual protocols and algorithms are integrated to evaluate and extract information from the data on, for example, stiffness, micro-vasculature, elasticity, perfusion, flow, shear wave speed, and other information that indicates the tissue state.

Figure 2:
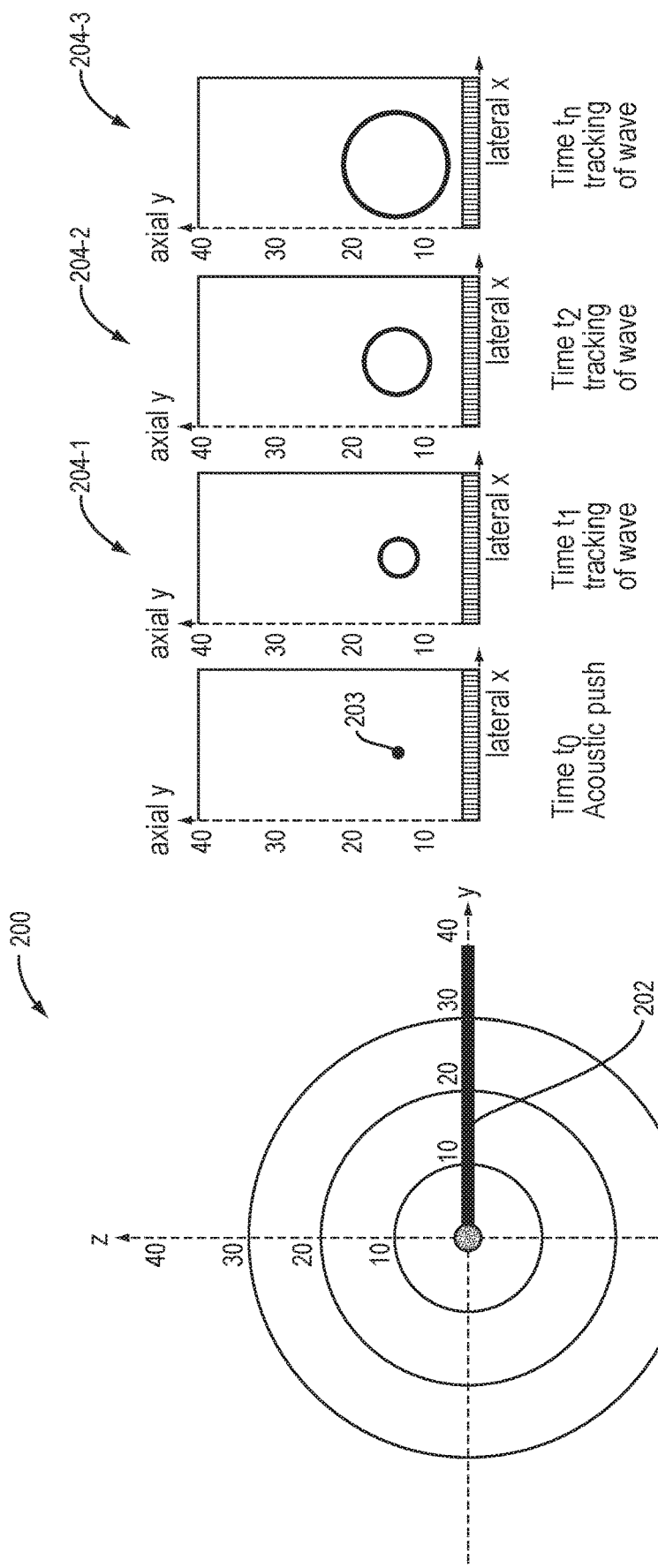
FIG. 2 is an illustration of a slice-based imaging to reconstruct both anatomical data from and functional data using ultrafast imaging modes for an example of shear wave imaging, in accordance with one embodiment of the invention.

FIG. 2 is an illustration of slice-based imaging 200 for the exemplary reconstruction of functional data from a propagating shear wave along with anatomical imaging data, which is in accordance with an embodiment of the disclosure. The slice-based imaging 200 can be captured with a fixed rotary position 202 of the sensor 201. An acoustic push 203 can be created at a location with a focused beam from multiple acoustic transmitters. The acoustic push causes deformation of tissue and the creation of shear wave propagating traversing the tissue laterally. Using ultrafast acquisition modes, the propagation of the shear wave through tissue can be observed in high resolution. Thereby, the time related spreading of the shear wave beam reflections provides data related to the shear stress introduced within the slice being analyzed. This data can be used to characterize the tissue structure of the slice of heart muscle to ensure ablation to the complete depth or thickness of the muscle. Further to this, by using ultrafast acquisition modes such as diverging or planewave transmissions, anatomical data (e.g. grayscale representation of tissue) can be reconstructed. This data can also provide an ability to decide the thickness and structure of the tissue prior to an ablation procedure and also the depth of ablation to ensure that the ablation is complete.

Figure 3:
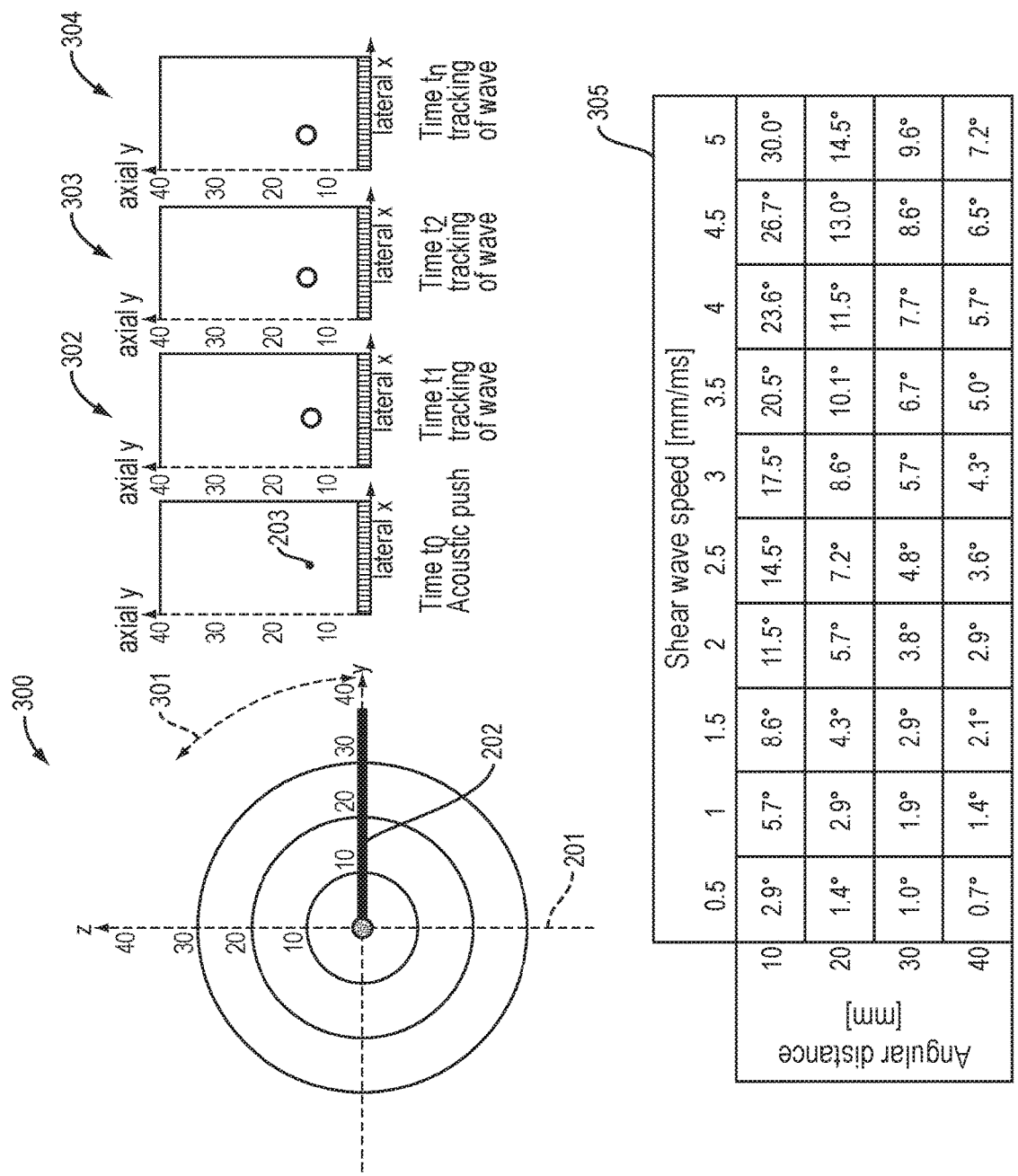
FIG. 3 is an illustration of a volume-based imaging to reconstruct both anatomical and functional data using ultrafast imaging modes for an example of shear wave imaging using rotating transducers that are ultrasound transmitters and sensors and the resultant speed of propagation of the wave within the tissue, in accordance with one embodiment of the invention.

FIG. 3 is an illustration of volume-based imaging 300 for the exemplary reconstruction of functional data from a propagating shear wave using a rotating sensor and the resultant speed of propagation of the wave within the tissue in accordance with an embodiment of the disclosure. In this functional reconstruction, the speed of spreading of a shear wave as induced by an acoustic push 203 within the volume covered by the arc 301 at different time periods 302, 303 and 304 is captured and analyzed. The analysis can determine the shear wave speed correlating to tissue stiffness and thus the characteristics of the atrium wall region. The typical speed of transition of the acoustic signal captured over time and related to thickness of the heart wall is shown as table 305. By using ultrafast acquisition modes, anatomical data (e.g. grayscale representation of tissue) can be reconstructed along with the functional data. This data can also provide an ability to decide the thickness and structure of the tissue prior to an ablation procedure and also the depth of ablation to ensure that the ablation is complete.

Figure 4:
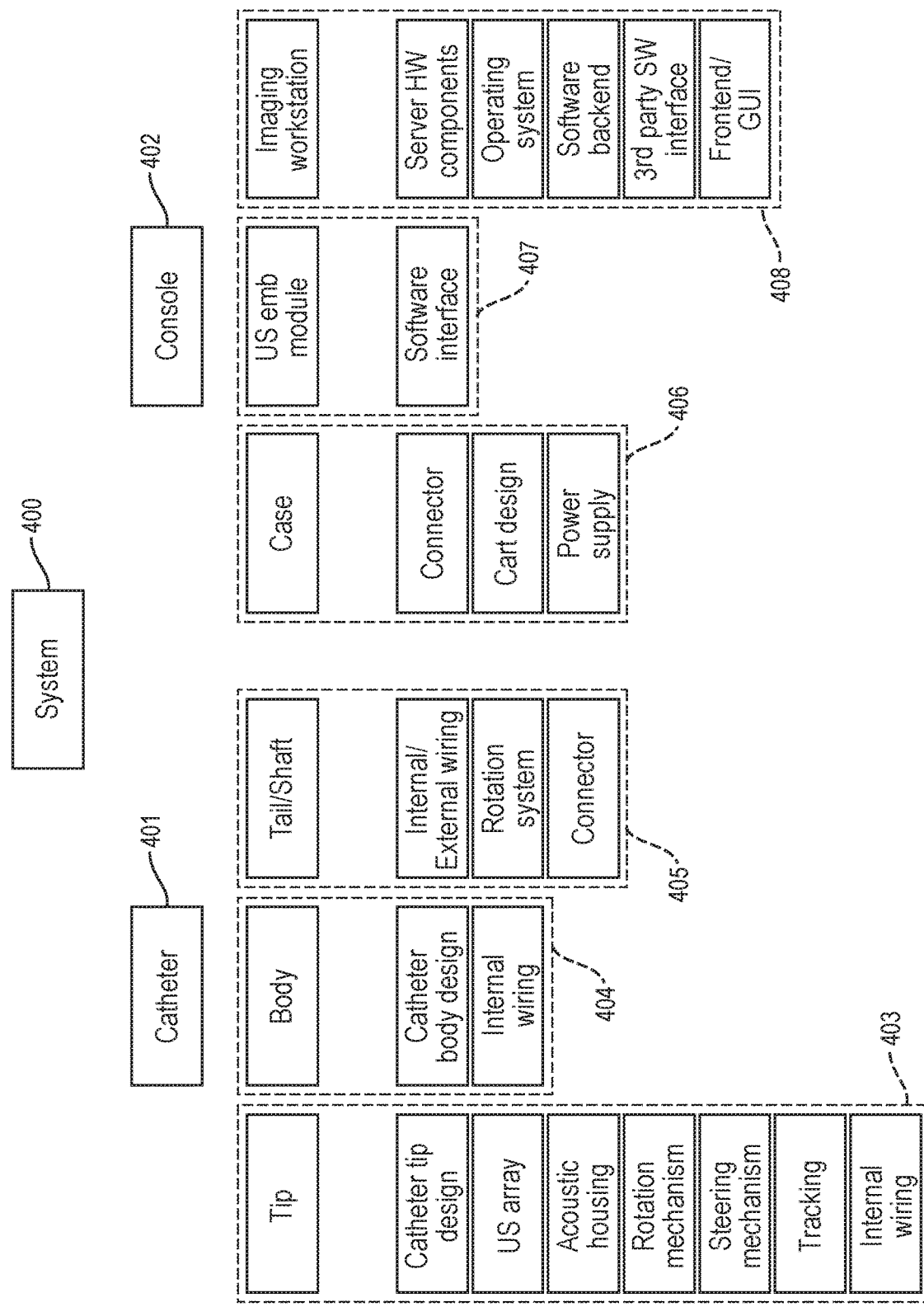
FIG. 4 is a schematic representation of an acoustic/ultrasound imaging system design in accordance with one embodiment of the invention.

FIG. 4 is a schematic representation of a design concept of an imaging system 400 in accordance with an embodiment of the disclosure. As shown in FIG. 4, the imaging system 400 includes a catheter 401 and a console 402.

The catheter 401 includes a catheter tip (or tip) 403. The catheter tip 403 includes an ultrasound transducer array 403B as part of the catheter tip 403A. The ultrasound transducer array 403B comprise ultrasound transmitters and sensors for transmitting pulses and for receiving an echo of the pulses. The tip 403 also includes an acoustic housing 403C or housing for the ultrasound transducer array 403B. The catheter tip 403 also includes control elements that enable steering 403E, tracking 403F, and controlled rotation 403D of the ultrasound transducer array within the acoustic housing 403B to allow the use of a rotating ultrasound transducer array or a stationary ultrasound transducer array where the control of rotation of the pulsing by the ultrasound transmitters is software controlled with no physical rotation. The transmitters send out ultrasound pulses in a predetermined rotational format and the sensors capture data from a 3-dimensional space around the catheter tip 403. The acoustic housing also houses the electrical wiring 403G for connectivity to the rotating ultrasound transducer array or the stationary ultrasound transducer array for control of transmission and reception of ultrasound data.

The catheter 401 also includes a body design 404. The body design 404 includes two concentric catheter elements. In some embodiments, the first concentric catheter element is a rotating shaft connection through a connector 405C which allows for rotation of the ultrasound transducer array of the catheter tip 403. The second concentric catheter element that is inside the first catheter element carries the electrical connections 404B to the connectors 405C between the ultrasound transducer array comprising ultrasound transmitters and sensors and other catheter tip controls to the connector 405C for connecting the electrical internal wiring 403G inside the acoustic housing to an external wiring cabling or shaft that connects to a processing and other analysis capability implemented in the console 402.

The catheter 401 can also include the tail or shaft 405 which provides for the catheter tip 403 to be moved away a distance from the console 402. In some embodiments, the shaft 405 can be configured to carry the rotating inner catheter, the rotation control wires and the sensor wire connections 405B from the internal wiring within the catheter tip 403 to the connector 405C that connects the rotation catheter and the external electrical connection to a second connector 406A of the console 402 through the shaft 405. The electrical wiring 403G supports a direct connection of each ultrasound transducer element in the catheter tip 403 to the ultrasound module 407 as required for transmission and receive of signals at all ultrasound elements in parallel (flat transmit, full receive).

The console 402 design can include three sub-units: a case 406, an ultrasound module 407, and a workstation 408 for processing and imaging. The console case 406 is a design of a holding cart 406B designed to allow the connector 405C from the shaft 405 of the catheter 401 to mate with a connector 406A on the console 402 and enable the transfer of rotational torque and to send and receive electrical signals to and from the catheter 401 to the console 402. The console case 406 also houses the processing workstation including a sever and storage capabilities for software and hardware. The case also holds a power supply module to provide power to the components of system 400.

The embedded ultrasound (US) module 407 comprises an embedded software based US module implemented on a work station 408 having a processing capability with interfaces 407A to the processing capability and electrical coupling via the coupling 406A to the shaft 405 and hence to the catheter 401. The embedded US module 407 provides operational guidance and control to the catheter tip 403 and also compiles and extracts data from the results received from the catheter tip 403.

The design of the imaging work station 408 further includes server hardware 408A, an operating system 408B and other software such as back-end software 408C and third party software 408D for data analysis, extraction and compilation of data and for generation of image data from the result analysis as well as all the necessary processing and storage capability that enable the embedded US module 407. The display work station also includes the display module and graphical user interface (GUI) 408E needed for generating two and three dimensional display and providing an interactive display manipulation capability to the user interacting with the display of the result.

The ultrasound module 407 can include software and processing capability for rotational control, programming of firing of ultrasound pulses based on planned sequences and a collection of raw data (echoes) received from the sensors. The imaging work station 408 can contain the server with the processing capability for handling all the planning, scheduling and implementation for ultrasound transducer firing and tip rotation and collection of reflected data by the sensors of the ultrasound transducer array. The ultrasound module 407 can also include software programs and capability to process the received and compiled ultrasound data. The received and compiled ultrasound data can be implemented to generate the necessary slice-based (two-dimensional) or volume based (three-dimensional) results. The server can also be configured to display the results on the display screens that are coupled to and form part of the server system. Further details of the system and its operation are disclosed below with respect to FIGS. 5 and 6.

Figure 5:
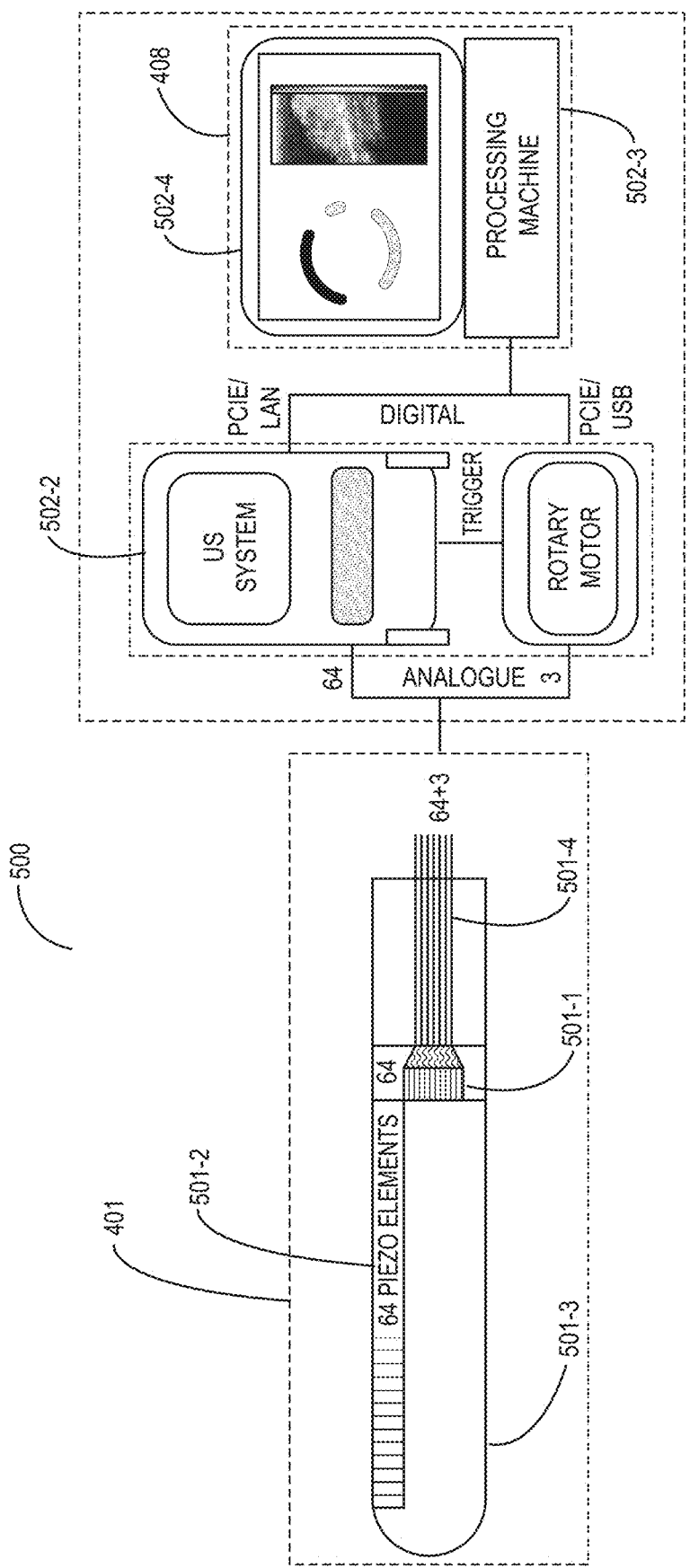
FIG. 5 is a schematic representation of an acoustic/ultrasound imaging system in accordance with one embodiment of the invention.
Figure 6:
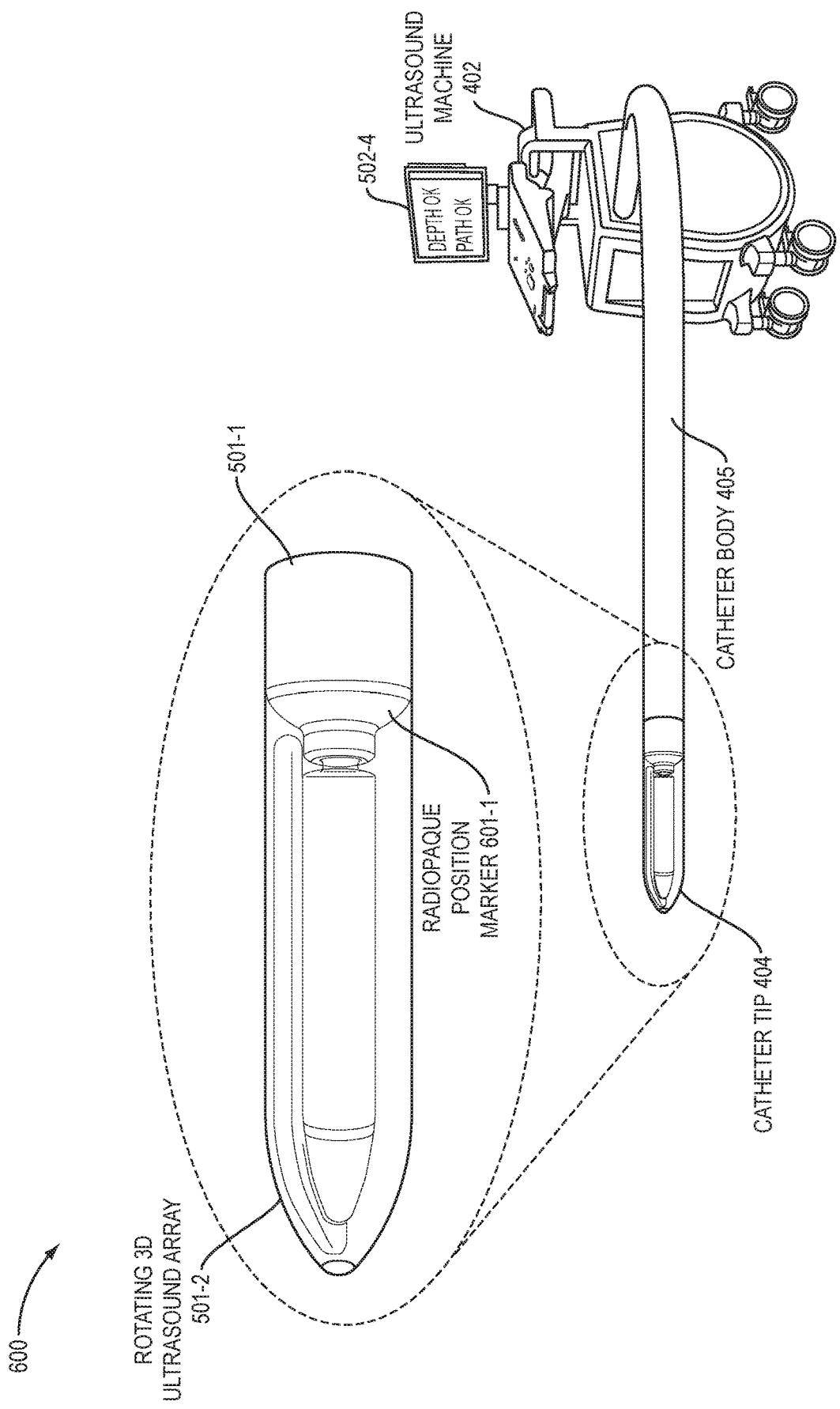
FIG. 6 is a schematic representation of a mechanical construct of an acoustic/ultrasound imaging system in accordance with one embodiment of the invention.

FIG. 5 is a schematic representation 500 of the system constructed from the design in FIG. 4 in accordance with an embodiment of the disclosure. FIG. 6 is a schematic representation of a mechanical ultrasound system 600 in accordance with an embodiment of the disclosure.

The following description relates to the design shown FIG. 4, and an implemented embodiment of system 400 shown in FIGS. 5 and 6. The catheter 401 includes an acoustic/ultrasound transducer array 501-2 and a console 402. The catheter 401 includes a catheter tip 403 that houses the acoustic/ultrasound transducer array 501-2. The ultrasound transducer array 501-2 includes a plurality of piezoelectric transducers, typically 1 to 64 or more (e.g. 128, 256, 512) piezoelectric transducers as transmitters for firing pulses and sensors or receivers for sensing the received echoes. In some embodiments, the ultrasound transducer array 501-2 comprises piezoelectric transducers (e.g. single crystal, composite ceramic) or alternative transducer designs (e.g. capacitive or piezoelectric micromachined ultrasound transducers, CMUT/PMUT) all of which work as both ultrasound transmitters and ultrasound receivers and in some other embodiments the acoustic/ultrasound array 501-2 comprise transducers, that are configured to operate separately some as ultrasound transmitters and others as receivers. The ultrasound transducer array 501-2 is housed in an acoustic housing 501-3 and the acoustic housing 501-3 is further enabled for steering and tracking of the catheter tip 403. The acoustic housing 501-3 uses radio-opaque markers 601-1 for insertion of the catheter tip 403 into the vasculature and tracking its movements within the vasculature. Although the acoustic housing 501-3 is shown housing the acoustic units and their connections only, it should be understood that the illustrated embodiment is not meant to be limiting.

The acoustic housing 501-3 can house additional/alternative sensors. For example, the acoustic housing 501-3 can house sensors for tracking the angular speed and position of the rotating ultrasound transducer arrays 501-2. The acoustic housing 501-3 can also house other supplementary sensors, such as temperature or pressure sensors, or tracking sensors. The acoustic housing 501-3 can also enable the rotation of the ultrasound transducer array 501-2 within the housing without disrupting the electrical interconnections through the body 404 of the catheter 401. The acoustic housing 501-3 can also be configured to provide an interface and coupling 501-1 of the ultrasound transducer array 501-2 with the catheter body 404 for rotation and for data transfer. Specifically, the acoustic housing 501-3 can provide interfacing for both electrical and mechanical, namely rotating attachments within itself. The coupling or connector 501-1 provides 360-degree rotation capability around the longitudinal axis for the acoustic transducer array 501-2.

The catheter body 404 is the mechanical and electrical connectivity for the rotating ultrasound transducer array 501-2, and other sensors and controls within the non-rotating acoustic housing 501-3 of the catheter tip 403 to the external connector or coupling 501-1. The catheter body 404 can include a concentric catheter with a core that is a rotating catheter capable of transferring rotation from a rotary motor 502-1 to the ultrasound transducer array 501-2 and an electrical cabling 501-4 inside the rotating catheter for electrically coupling the ultrasound transducer array 501-2 and other sensors and control wires to the connector 501-1. In some embodiments, the rotary motor 502-1 is configured to rotate at variable speeds between 10 and 3000 RPM. The rotating catheter provides the drive connection from the rotary motor 502-1 through a shaft 405 of the catheter 401 to the catheter body 404 and through the connector 501-1 to the ultrasound transducer array 501-2. The inner rotating section, within the acoustic housing 501-3, that includes the ultrasound transducer array 501-2 of the catheter tip 403, can rotate at a variable speed between 10 and 3,000 RPM. The inner core of the catheter body 404 also includes the electrical cabling 501-4 configured to carry electrical wires for data and control, typically at least 64 transducer wires and 6 ground wires for the ultrasound transducer array 501-2 of the catheter tip 403, and the electrical cabling 501-4 includes at least an additional 3 control wires connecting to the motor control to enable synchronization of the transmitter firing with the rotation of the ultrasound transducer array 501-2. If additional sensors are included in the rotating section of the catheter tip 403, connection wires to these are also included in the cabling 501-4. The electrical cabling 501-4 connects to an electrical interface at the coupling mechanism 501-1 to the wires from the ultrasound transducer array 502-2. The catheter body 404 is part of the catheter tip 403 and is attached to the coupling mechanism 501-1 that is the connecting interface for both mechanical rotation and electrical connections to the ultrasound transducer array 501-2 within tis acoustic housing 501-3 of the catheter tip 403.

The tail or shaft 405 of the catheter 401 allows the catheter 401 to interface with the console 402. In this configuration, the catheter tip 403 is able to rotate using the cable through the shaft 405 connecting to the coupling mechanism 501-1 of the catheter body 404. The shaft 405 of the catheter 401 also enables the connection of the signal and control wires 501-4 to the ultrasound system 502-2 for controlling the generation and transmission of the ultrasound pulses by the ultrasound array 501-2. The shaft 405 of the catheter 401 also enables the delivery of collected response data to the ultrasound module 502-2 in the case 406 of the console 402. The shaft 401 can be coupled to the console via a second interface connector 406B for transferring the data and the mechanical movements.

Figure 11:
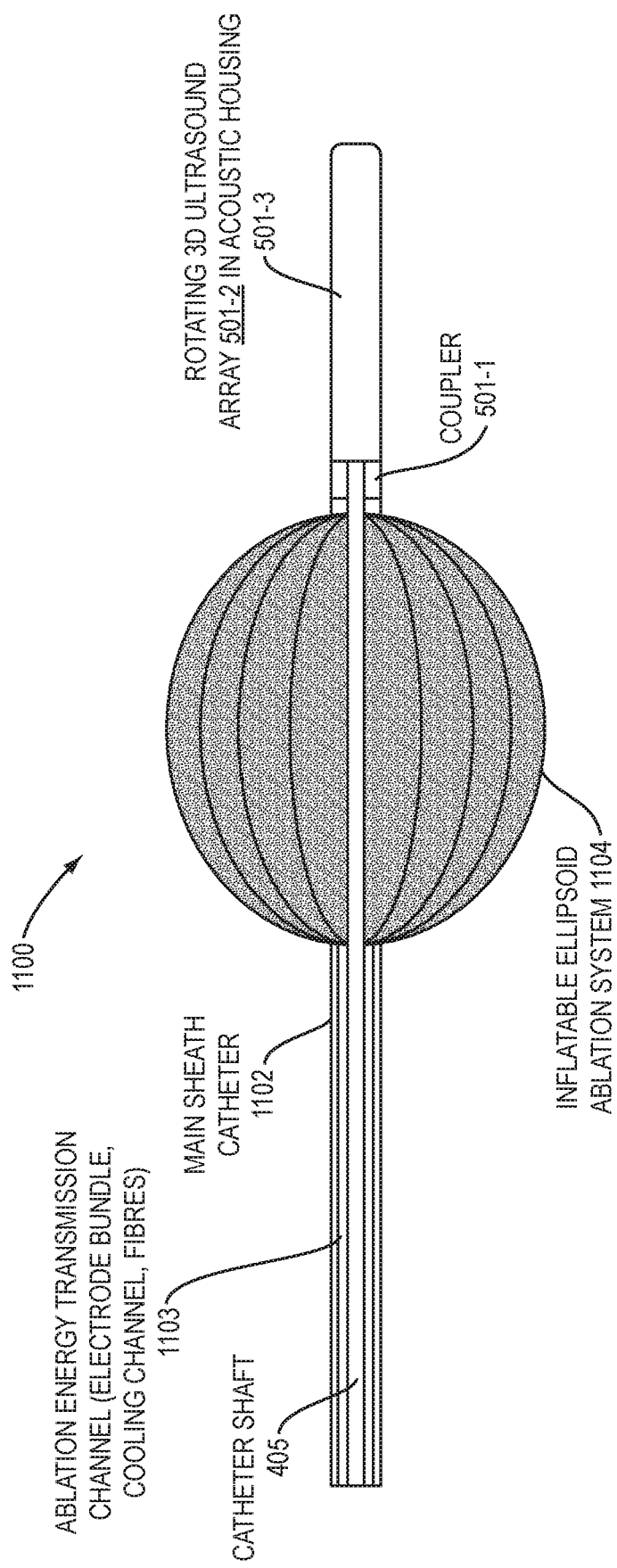
FIG. 11 is a detailed schematic diagram of the distal end of the acoustic/ultrasound imaging system design in accordance with one embodiment of the invention.
Figure 12:
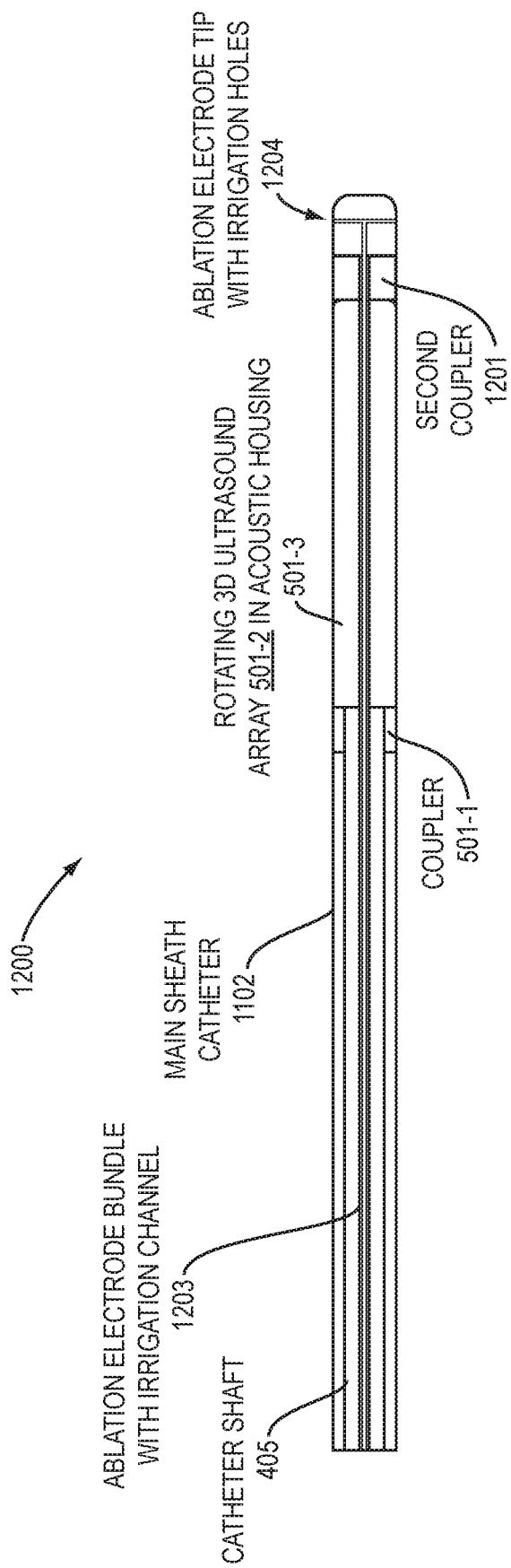
FIG. 12 is a detailed schematic diagram of the distal end of the acoustic/ultrasound imaging system design in accordance with one embodiment of the invention.

FIGS. 11 and 12 show two exemplary implementations of the active imaging section of the catheter in combination with another active section. In particular, FIG. 11 is an exemplary implementation 1100 used for an ablation operation using an inflatable ellipsoid ablation system 1104. The inflatable ellipsoid ablation system 1104 is attached proximally to the rotating 3D ultrasound array 501-2 in its acoustic housing 501-3. The imaging array 501-2 in its acoustic housing 501-3 is used for capturing images during ablation procedure. FIG. 11 shows a main sheath catheter 1102 carrying the catheter shaft 405 of the catheter 401 and the ablation energy transmission channel 1103. The catheter shaft 405 connects through the coupling 501-1 to the rotating 3D ultrasound array 501-2 in the acoustic housing 501-3. The ablation energy transmission channel 1103 carries the electrode bundle and channel for coolant etc. for the inflatable ellipsoid ablation system 1104.

FIG. 12 is another exemplary implementation 1200 used for an ablation operation using an ablation electrode tip coupled distally to the rotating 3D ultrasound array 501-2 in its acoustic housing 501-3 used for capturing images during ablation procedure. The main sheath catheter 1102 in this implementation carries the catheter shaft 405 and the ablation electrode bundle and an irrigation channel 1203. The coupler 501-1 couples the main sheath and the catheter shaft to the rotating 3D ultrasound array 501-2 in the acoustic housing 501-3. A second coupler 1201 is used to couple the ablation tip with irrigation holes 1204 to the ablation electrode bundle and an irrigation channel 1203 to allow the ablation procedure and cooling of the location of the procedure while 3D images are captured by the rotating 3D ultrasound array.

Referring back to FIG. 4, in some embodiments, the case 406 forms a protective cover for the console 402 with all the rest of the components needed for planning the ultrasound imaging procedure as well as generating and processing of the results of the imaging procedure by the ultrasound system 400. The console 402 houses at least a software based embedded ultrasound module 407, the rotary motor and a imaging work station 408 with the necessary processing power, the storage capability for software and data storage capability etc. The case 406 also includes the interfacing capabilities and power supplies for the operation of the system 400.

In some embodiments, the ultrasound module 407 can include an ultrasound system 502-2, which has the capability, processing power, and the software to plan the procedure, and initiate pulse firing by the transmitters of the ultrasound transducer array 501-2 within the catheter tip 403. The ultrasound module 407 can also have the rotary motor 502-1 coupled through an inner core of the catheter shaft 405. The rotary motor 502-1 can be configured to control the rotation of the catheter tip 404 and synchronize the rotation with the transducer firing based on the plan of the procedure. The synchronization can be achieved by having the ultrasound system 502-2 providing the necessary trigger signals to the rotary motor 502-1 and the rotating ultrasound transducer array 501-2. The trigger signal and rotation synchronization with feedback are achieved through the 3 signal lines connecting the motor with the ultrasound transducer array 501-2 of the catheter tip 403. All the electrical connections, typically 64 transducer and sensor wires and the 3 motor control and synchronization wires, are connected from the console or ultrasound machine 402 to the wiring of the catheter body 404 of the catheter tip 403 through the catheter shaft 405 of the catheter 401. An imaging work station is used as a processing machine 502-3. The processing machine 502-3 may be used to provide the synchronization signal and computation and supervision/control of the motor rotations. The link between the motor and the processor typically is a USB, RS232 or Ethernet connection, though it is not meant to be limiting.

The console 402 also includes the work station and display 408 providing the processing capability using one or more processors in a processing machine 502-3 for the system 400. The processing machine as shown being within the console is not to be considered as limiting. The processing machine 502-3 may be implemented as distributed processors including implementation as cloud-based processors. It can also be implemented as a single processor or a multi-processor configuration within the constraints of the application. The processing machine provides the capability to the ultrasound system 502-2 for control of features and compilation and analysis of data collected. As may be well understood by individuals conversant with ultrasound imaging the sensed data at the input to the ultrasound processing system 502-2, through the 64 electrical connections, is analog in nature and is converted to a digital format within the ultrasound system 502-2 and stored. The data and results are stored in a dedicated storage on the imaging work station or in a cloud storage associated with the processing machine. The results are compiled and processed to produce two, three or four dimensional display to be displayed on the display unit 502-4 of the console 408. The digital connections are achieved, typically over a high speed peripheral Component interface (PCI) or a local area network (LAN) Ethernet connection.

Figure 10:
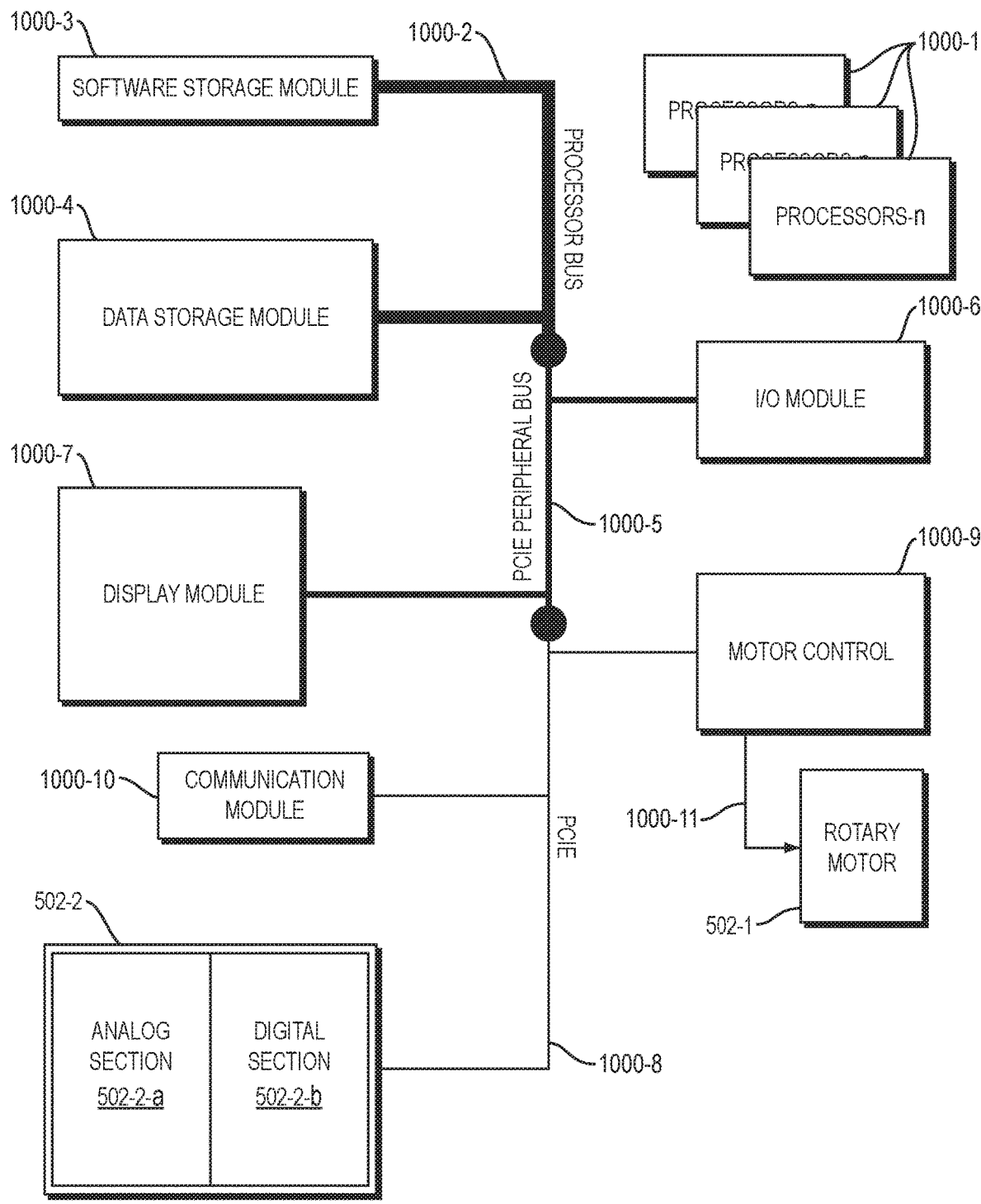
FIG. 10 is a schematic diagram of a processing system in accordance with one embodiment of the invention.

FIG. 10 shows a typical processing system that may be used as part of the disclosed ultrasound system. The processing system may comprise a single processor or a multiprocessor 1000-1, implementation. The processors are connected over a processor bus 1000-2, that also connect to the software storage memory 1000-3, and the data storage memory 1000-4. A PCIE peripheral bus 1000-5 is used to connect the processor bus to peripheral devices like input-output modules 1000-6 such as drawing tablets, key boards etc., and display module 1000-7. A PCIE based local area network (LAN) 1000-8 is used to connect to the motor control module 1000-9, communication module 1000-10, and the Ultra sound processing system 502-2 comprising an analog section 502-2-a and a digital section 502-2-b. The motor control module 1000-9 is coupled to the rotary motor 502-1 via a motor control link 1000-11 that is either a USB, RS232 or Ethernet connection. Though a specific implementation of the processing system is shown for the current application, it is not meant to be limiting alternate configurations of processors and peripherals that are interconnected for use are possible, as will be well understood by practitioners of the art. These are expected to be covered by the description and figures presented herein.

Figure 7:
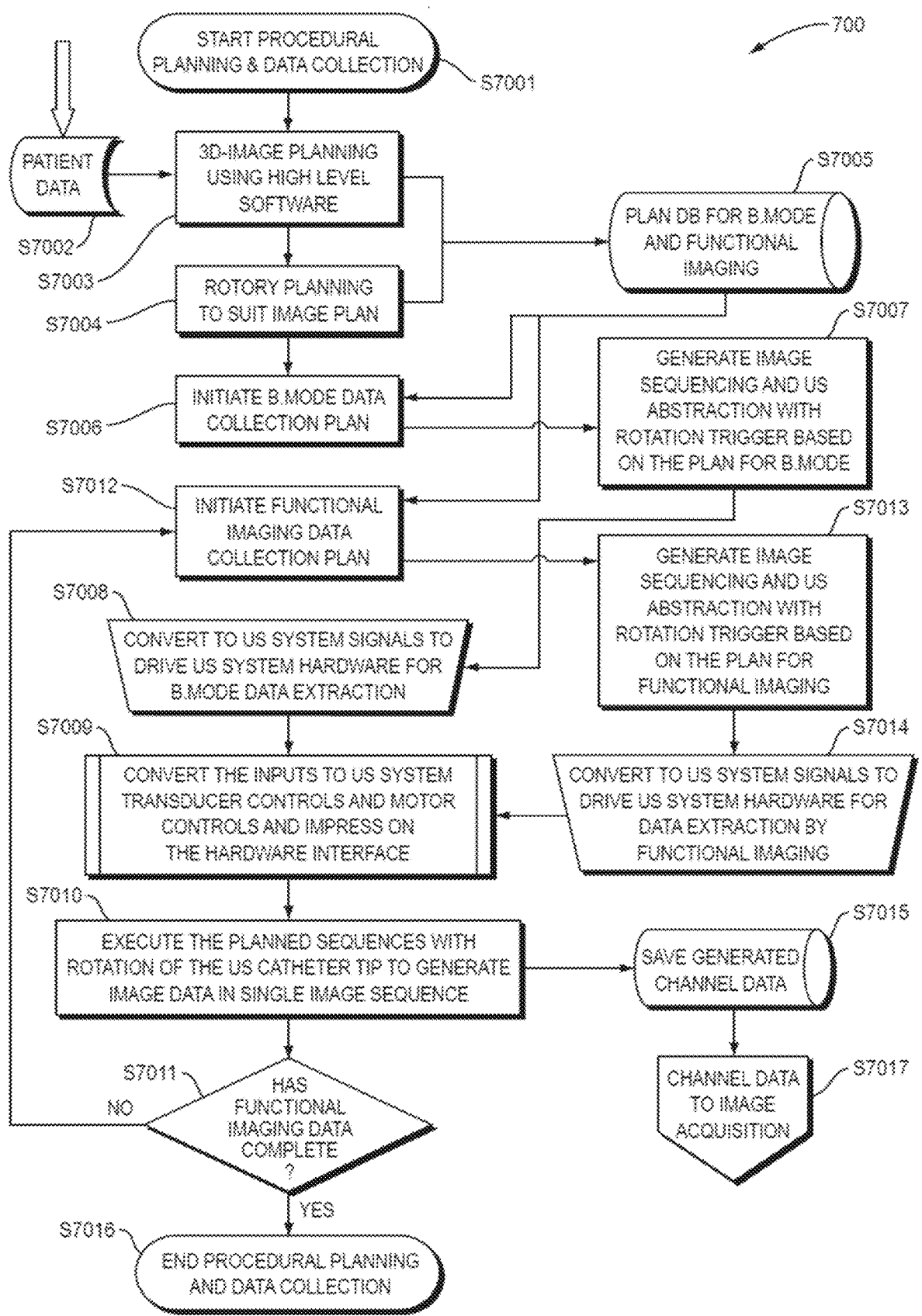
FIG. 7 is a flow chart illustrating a process for planning and collecting data in accordance with one embodiment of the invention.

FIG. 7 depicts a flow chart describing a process 700 for planning and collecting data to be implemented in an ultrasound system, such as the one shown in FIGS. 4-6, in accordance with an implementation of the present disclosure. The process 700 can use inputs from the patient, the medical tests conducted on the patient and the capabilities of the system 400. The procedure planning is a pre-requisite of the process that enable the data collection using the system 400. At S7001, the procedure planning and data collection process 700 of the system 400 is initiated. At S7002, the information of the patient, including information from medical tests, are input into the system through the user interface. At S7003, high level software of the ultrasound system is used with the patient-related inputs to generate three-dimensional image planning.

The image planning also includes the rotary planning to synchronize the rotation of the imaging sensors with the ultrasound transducer and response collection sensors at S7004. At S7005, the planned procedure with the planned rotary plan is saved in the planning database of the ultrasound system. In some embodiments, there can be at least two types of image data collection. For example, there can exist B. mode (brightness mode) which is two-dimensional imaging using ultrasound imaging. The other type of image data collection can include intra-vascular functional imaging using ultrasound imaging to characterize the tissue using one or more of the previously described extraction protocols (for example elasticity imaging, tissue micro-Doppler, coherence imaging, etc.). In this exemplary flow chart, elastic imaging is discussed.

At S7006, the saved plan for B. mode can be retrieved from the plan database and the B. mode data collection plan can be initiated. For B. mode, the three-dimensional functional anatomical software can be implemented to generate image sequencing and ultrasound abstraction with rotation trigger based on the plan design (S7007). At S7008, the generated image sequencing and ultrasound abstraction with rotation trigger based on B. mode is converted to ultrasound system signals to drive the ultrasound system hardware.

The converted signals to drive the ultrasound system hardware are provided to the hardware interface of the ultrasound system 400 (S7009). At S7010, the ultrasound system hardware executes the instructions in the planned sequences by firing the ultrasound transducers and collecting the reflected data signals with rotation of the ultrasound catheter tip in synchronized fashion to generate and collect the image data in a single image sequence.

At S7015, the generated B. mode data can be stored in the channel data store. At S7011, a determination can be made whether the second data collection plan, the functional tissue imaging plan for intra vascular tissue characterization imaging, has been completed. If not completed, the plan for functional tissue imaging can be retrieved from the plan database and the elasticity imaging data plan execution can be initiated (S7012).

For functional tissue imaging, the three-dimensional functional anatomical software is implemented to generate image sequencing and ultrasound abstraction with rotation trigger based on the plan design (S7013). At S7014, the generated image sequencing and ultrasound abstraction with rotation trigger based on functional tissue imaging is converted to ultrasound system signals to drive the ultrasound system hardware.

The converted signals to drive the ultrasound system hardware are provided to the hardware interface of the ultrasound system 400 (S7009). At S7010, the ultrasound system hardware executes the instructions in the planned sequences by firing the ultrasound transducers and collecting the reflected data signals with rotation of the ultrasound catheter tip in synchronized fashion to generate and collect the image data in a single image sequence.

At S7015, the generated data from functional tissue imaging is stored in the channel data store with the B. mode data. At S7011, a determination is made as to whether the functional tissue imaging mode is completed to ensure that both B. mode and tissue elasticity mode data imaging has been completed. Where it is determined that the functional tissue imaging mode is completed, then the procedural planning and data acquisition process is stopped (S7016). At S7017, the channel data-store now contains all data generated, ready for processing and image acquisition.

Figure 8:
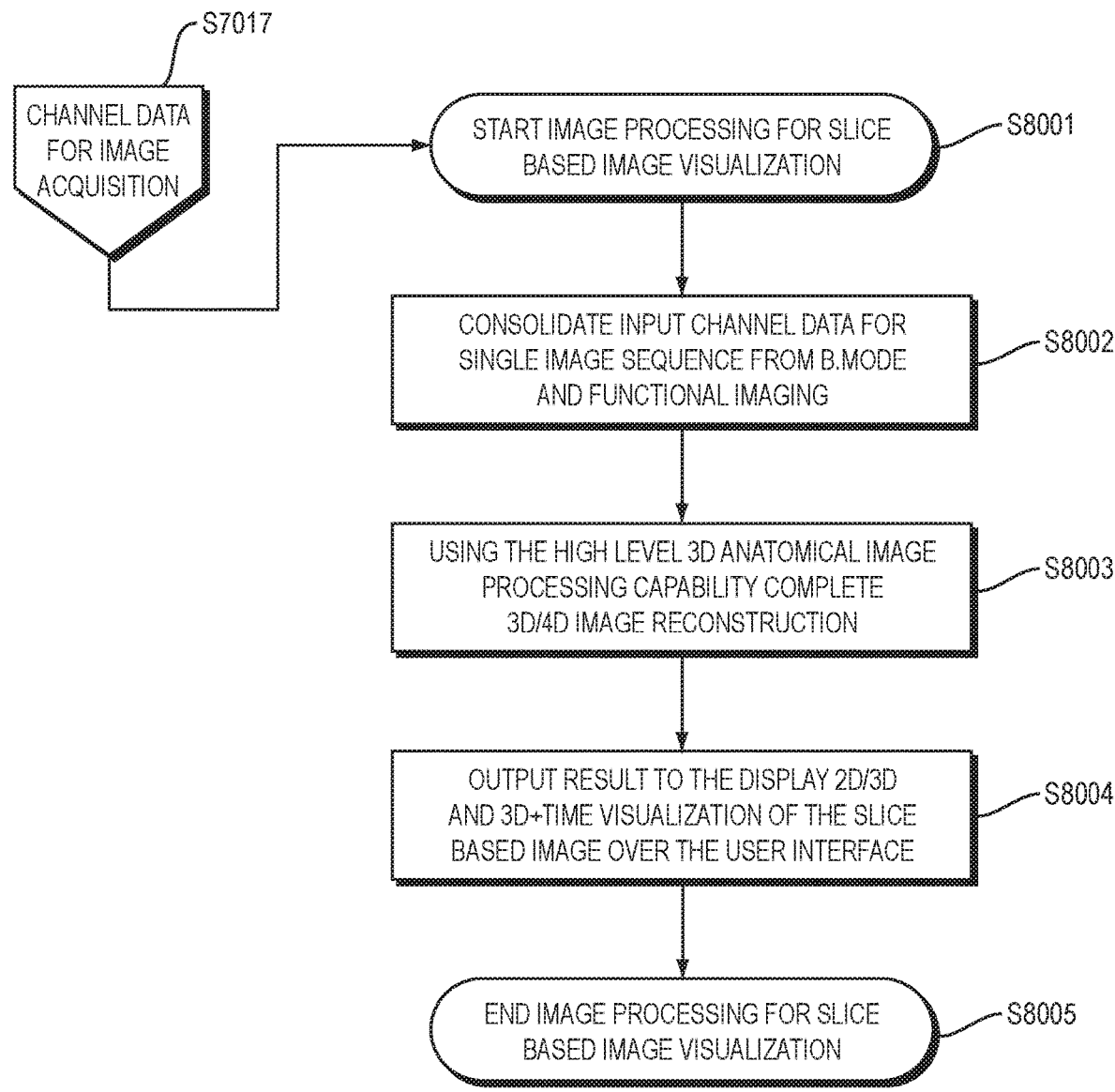
FIG. 8 is a flow chart illustrating a process for reconstructing and visualizing two- or three-dimensional slice-based imaging in accordance with one embodiment of the invention.

FIG. 8 depicts a flow chart describing a process 800 for reconstructing and visualizing two- or three-dimensional slice-based imaging in accordance with an implementation of the present disclosure. The image data collected and stored in the channel data-store can be retrieved and the processing can be commenced for slice-based image visualization (S8001). At S8002, the channel data for single image sequence from B-Mode and functional tissue Imaging can be consolidated. At S8003, two- or three-dimensional image reconstruction can be performed using the consolidated imaging data and the high-level three-dimensional anatomical image processing capability of the ultrasound system 400.

The two/three-dimensional image reconstruction result can be output to the display on the system display, as two- or three-dimensional visualization of the slice-based image over the user interface of the ultrasound system. The displayed image can be provided for review by the experts (S8004). At S8005, the image data processing for slice-based image reconstruction is complete and the process is stopped.

Figure 9:
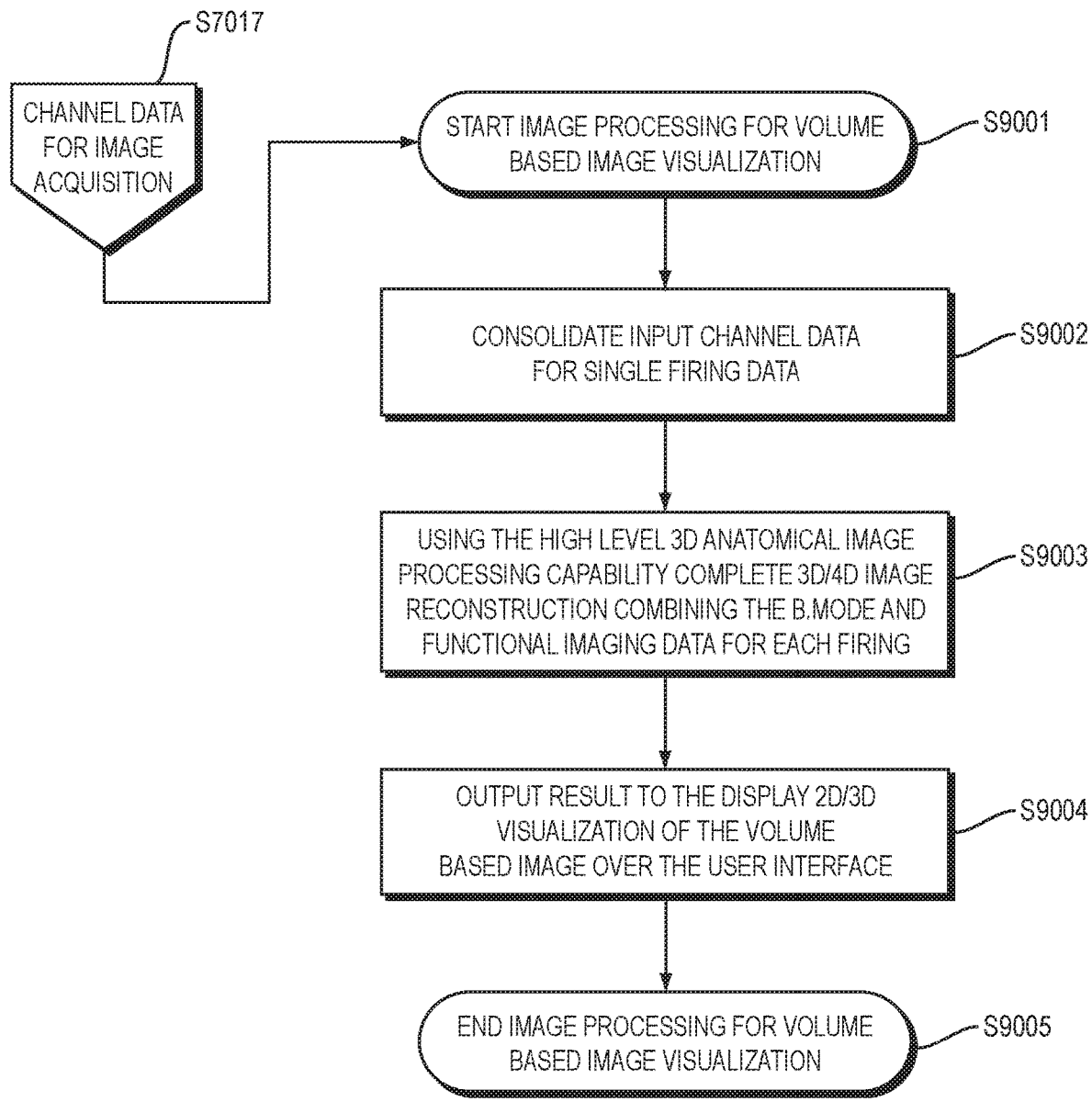
FIG. 9 is a flow chart illustrating a process for reconstructing and visualizing three- or four-dimensional volume-based imaging in accordance with one embodiment of the disclosure.

FIG. 9 depicts a flow chart describing a process 900 for reconstructing and visualizing three- or four-dimensional slice-based imaging in accordance with an implementation of the present disclosure. The image data collected and stored in the channel data-store can be retrieved and the processing can be initiated for volume-based image visualization (S9001).

At S9002, the input channel data from B-mode and tissue parameter imaging can be consolidated for single firing pattern. Three- or four-dimensional image reconstruction combining the B-mode and functional imaging data for each firing can be re-constructed using the high-level three-dimensional anatomical image processing capability (S9003).

The result can be output as a three- or four-dimensional image over user interface to display on the system display of the ultrasound system 400. The results can be displayed for review and by experts (S9004). At S9005, the image data processing for volume-based image reconstruction is complete and the process is stopped. By using the combination of B-mode and tissue functional parameter imaging to collect and generate both slice based and volume based images of the surfaces and into the tissue, embodiments of the invention are able to use unique algorithms to ensure completeness of procedures, especially AF procedures.

FIG. 10 depicts a schematic diagram of a processing system in accordance with one embodiment of the invention.

FIG. 11 is a detailed schematic diagram of the distal end of the acoustic/ultrasound imaging system design in accordance with one embodiment of the invention.

FIG. 12 illustrates is a detailed schematic diagram of the distal end of the acoustic/ultrasound imaging system design in accordance with one embodiment of the invention.

Ultrafast Imaging

On the foundation of the specific requirements of electrophysiology (EP) ablation procedures as well as the potential enabled by ultrafast imaging techniques, the device may integrate state of the art imaging with a bespoke rotational 3D-intracardiac echocardiography (ICE) catheter system to provide a system fully tailored to the requirements of ablation procedures in the EP lab. The ultrafast imaging techniques may enable both the required anatomical capture range (>80 mm volumetric coverage) as well as the specific monitoring of ablation lesions from the retrieved rotational 3D+t data.

The imaging system may allow for the reconstruction of a cylindrical imaging volume. Within this field of view, the system may provide both anatomical information, as well as functional tissue information for ablation monitoring:

a) Anatomical information as mentioned above in the detailed description.

b) Functional information as mentioned above in the detailed description.

Focusing on optimal image quality, both the impact of cardiac pulsation due to the volumetric update rate as well as the spatial resolution per volume need to be considered for the hardware design. As patients are treated under sedation or general anaesthesia, anticipated heart rates in ablation procedures are between 50 bpm and 120 bpm, which is equivalent to a maximum cardiac rate $f_{c,max}$ of 2 Hz. Previous studies have suggested that a total update rate of >20 Hz may be sufficient to fully capture dynamic movements with this maximum cardiac rate.

Anatomical evaluations showed cardiac walls in the range between 0.5 mm and 4.4 mm, with the pulmonary veins exhibiting diameters between 10 mm and 20 mm. In one example, by reconstructing volumetric data with 40 mm, imaging depth all around the catheter, and a ≤0.25 mm isotropic spatial resolution for reconstructed 3D volumetric data allows for a depiction of all required structures in sufficient detail, exceeding all currently available imaging methods.

Achieving optimal spatial resolution while enabling artifact-free imaging of dynamic cardiac structures may require a careful balance between spatial sampling and volumetric update rate. Thereby, the achievable angular spatial resolution within a rotationally-acquired 3D volume may be directly related to the angle φ between individually acquired 2D images around the catheter as shown in the following equation:

$$\delta_e = d_a \sin\left(\frac{\phi}{2}\right) \quad (1)$$

where $d_a$ is the target imaging depth. The angular resolution may be limited by half of the rotational sampling rate (i.e. distance between two image planes), where smaller angles intuitively lead to better resolutions (smaller $\delta_e$). However, the volumetric update rate is inversely proportional to ø and the time required per 2D ($t_{2D}$) image acquired at each position, as shown in the following equations:

$$f_{3D} = \frac{\phi}{2\pi} f_{2D} \qquad (2)$$

$$t_{2D} = n_\alpha \frac{2d}{c} \qquad (3)$$

where intuitively smaller angles (i.e. less spacing between 2D imaging planes) may lead to a lower volumetric update rate (more time required per volume).

Considering the requirements above, in one embodiment, in order achieve a target $\delta_e$=0.25 mm, angles between each image plane need to fulfill ø=0.72°. With a fixed ø, 500 individual images may be required per catheter revolution to reconstruct one volume. To maintain volumetric update rates of ≥20 Hz, the catheter system may need to support ≥1200 revolutions per minute (rpm). Finally, from Eq. (2), it follows that $f_{2D}$ needs to be ≥10 kHz to allow for a volumetric imaging rate of ≥20 Hz with a spatial resolution 0.25 mm. From the requirements with respect to $f_{2D}$ it becomes evident that ultrafast imaging techniques may be required to enable imaging with the constraints given by the application and system design. The latter, however, may require a full electrical connection from each transducer element to a respective imaging channel, as for both transmit and receive modes, all transducer elements are utilized in parallel. This may be in contrast to scanline-based approaches, where subapertures are employed, enabling the utilization of multiplexing techniques at the tip to avoid a full 1:1 interconnect between transducer and imaging channel. Thereby, a channel provides the analogue and digital frontends to allow for transmit pulsing and receive analogue to digital conversion along with amplification and other analogue processing stages. To enable ultrafast imaging with fulfilling the requirements discussed above, at least one embodiment of the system provides a full 64-channel array design. Thus, in contrast to other catheter designs, this allows for a direct utilization of all native Ultrafast imaging techniques such as planewave or diverging wave imaging. As used herein, planewave imaging may refer to an ultrasound imaging modality where, through a flat transmit of all transducer elements (at different angles), a plane wave front may traverse the tissue and may be partially scattered back to the transducer. From the received RF (channel) data the overall image may be reconstructed at once in parallel by dynamically beamforming the received RF data for each target position. Other (native 3D) transducer arrays presented in literature for intracardiac imaging do not allow for the generation of full aperture imaging, nor do they allow for full 360 coverage around the catheter, both of which are prerequisites for accurate depth and contiguity/permanency monitoring of ablations.

Ultrafast imaging techniques allows for the reconstruction of image data with both superior image quality and high imaging rates. Thereby, at least one embodiment of the system herein employs coherent planewave compounding, where multiple planewave transmit cycles are used to receive echoes allowing for the reconstruction of image data with high signal to noise ratio. Considering a single planewave scenario at first, a planewave front with angle α is generated at the transducer array by a respective time delay of the individual transducer elements according to their distance from the transducer center as shown in the equation below:

$$\Delta_i = \frac{\sin(\alpha) x_i}{c} = \frac{\sin(\alpha)(\delta_{lat} i_{lat})}{c} \qquad (4)$$

Where:
α is the planewave tilt angle,
$x_i$ the lateral distance to the transducer centerpoint,
$\delta_{lat}$ the lateral spacing of ultrasound elements,
$i_{lat}$ the number of the i-th element,
c the speed of sound in the medium, and
$\Delta_i$ the specific time delay for element i for the given parametrization.

With a planewave transmission, the transmit-time until a wave reaches a desired target $p_k=(x_k,y_k)$ point in the 2D imaging plane is given by the equation below below:

$$\tau_{tx}(x_k, y_k, \alpha) = \frac{(x_k \sin(\alpha) + y_k \cos(\alpha))}{c} \qquad (5)$$

Figure 13A:
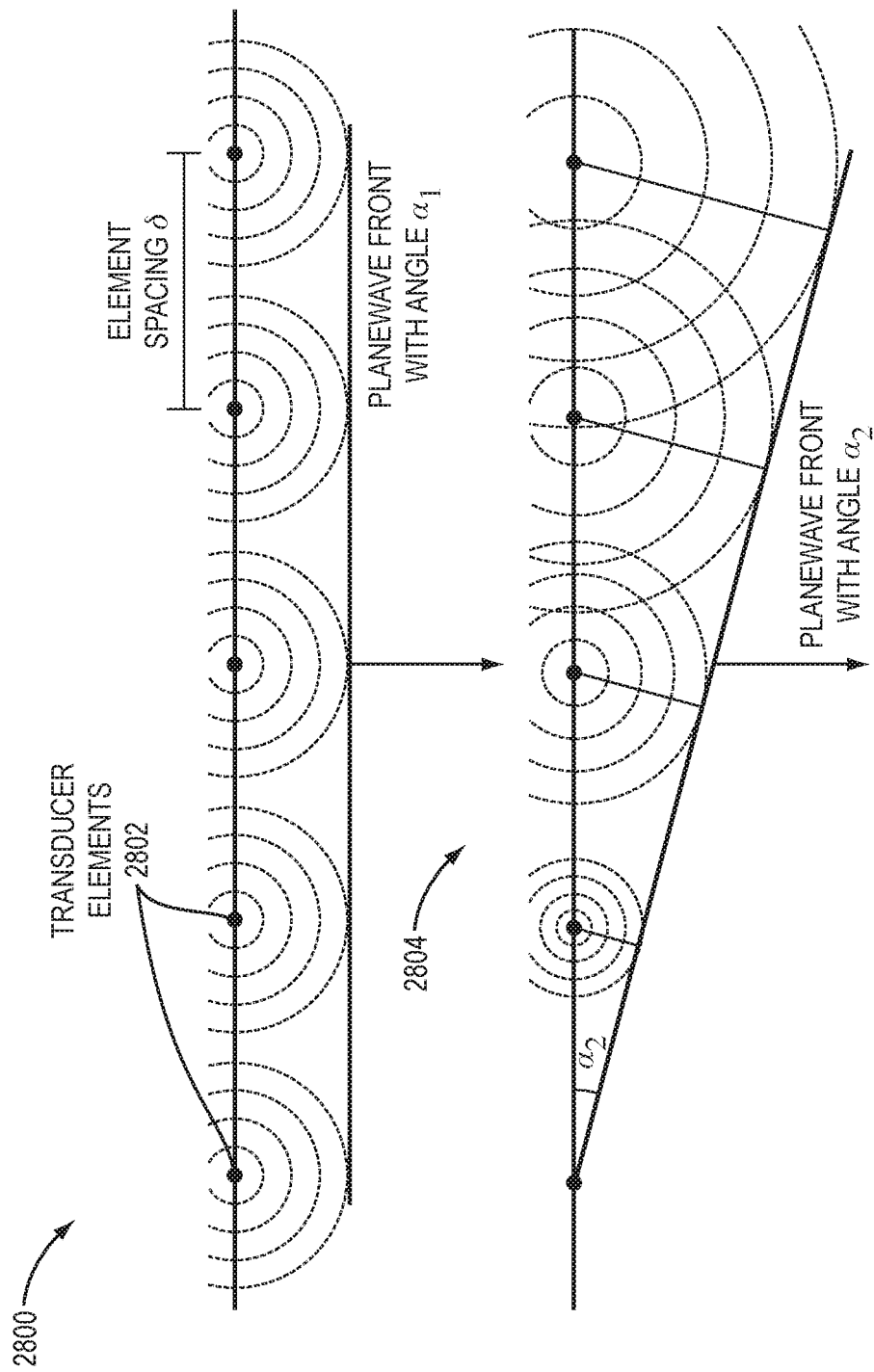
FIGS. 13A-C is an illustration of planewave imaging and catheter 3D coordinates, in accordance with one embodiment of the present invention.

Referring to FIG. 13A, there is shown a planewave transmission, in accordance with one embodiment of the present invention. By transmitting a pulse on all transducer elements 2802 simultaneously, a flat planewave 2800 may be emitted (top). The flat planewave may be further defined by a planewave front angle, $\alpha_1$. Through controlling the temporal delays between the triggering of the individual elements, an angled planewave 2804 may be generated (bottom). The angled planewave may be further defined by planewave front angle, $\alpha_2$.

Figure 13B:
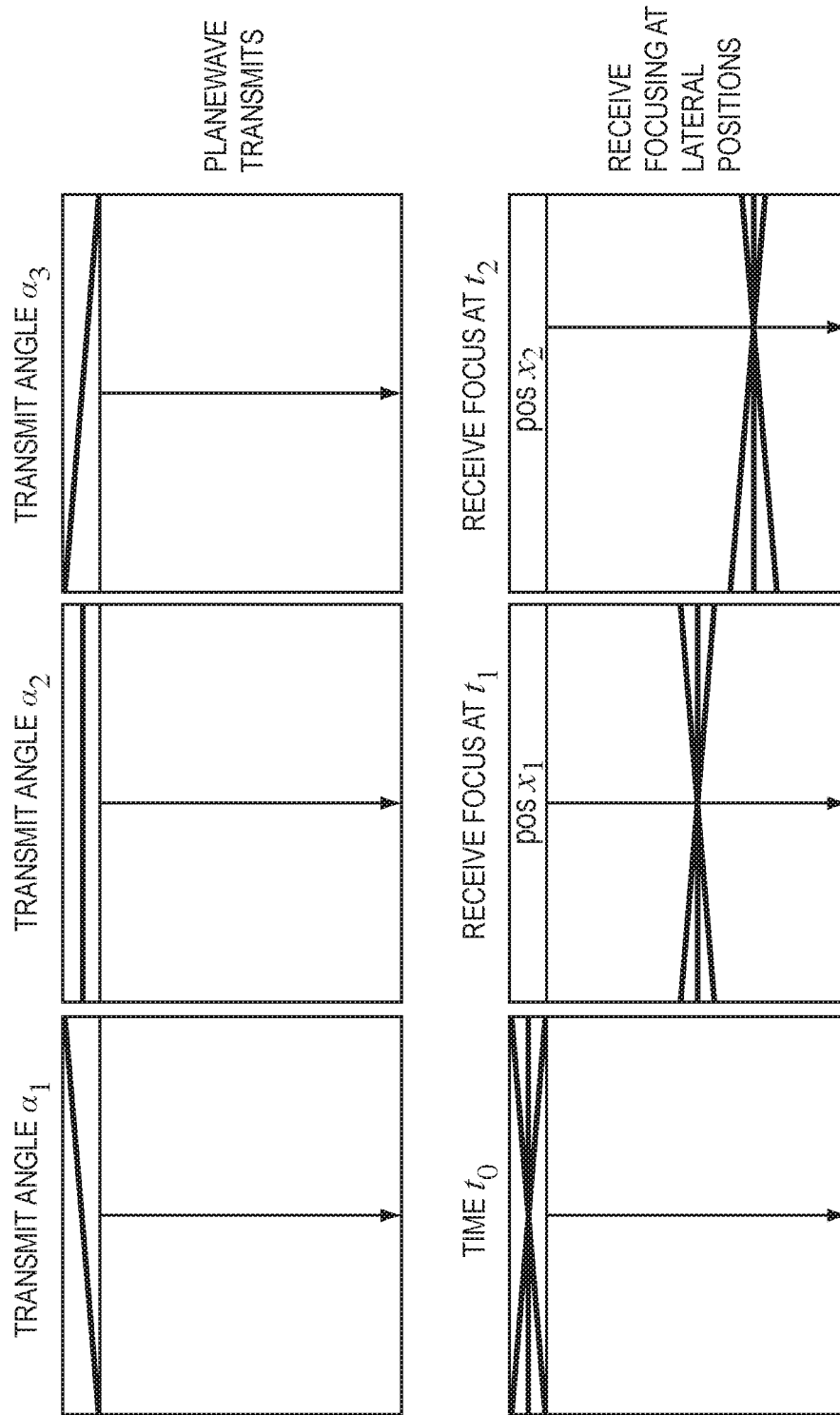

Referring to FIG. 13B there is shown planewave compounding to improve SNR and image quality, in accordance with one embodiment of the present invention. Illustrated herein are three planewave transmits with different angles. From the ultrasound array, several planewaves may be transmitted into the target tissue with different transmit angles, $\alpha_1$, $\alpha_2$ and $\alpha_3$ (top row). Through a coherent compounding of individually received planewave echoes, focusing may be achieved from the received data for each position (bottom).

More general, while the images reconstructed form a single planewave transmit are sufficient for 2D image reconstruction, the low signal amplitudes lead to a low SNR, which is why in practice multiple planewave transmits may be combined to improve the overall image contrast as well as the spatial resolution. In this respect, a series of planewave transmit-receive cycles may be performed with different planewave angles $\alpha_i$ instead of a single fixed transmit. This has been shown to provide image quality exceeding classical scanline imaging, as well as to enable the reconstruction of images with high quality from few planewave transmits. FIG. 13B shows an overview of the concept for the example of three planewave transmits with different angles. Thereby, each transmit-receive cycle is reconstructed into a 2D signal following Eq. (6) before a 2D frame is coherently compounded by a summation of the individually reconstructed 2D signals in Eq. (7).

$$I(x_k, y_k, \alpha) = \sum_{i_{lat} \in a} C(i_{lat}, \tau(x_k, y_k, \alpha, i_{lat})) \qquad (6)$$

$$I_{2D}(x_k, y_k) = \sum_{i=1}^{n} I(x_k, y_k, \alpha_i) \qquad (7)$$

With respect to selecting the appropriate set of transmit angles $\alpha_i$, the goal is to minimize the number of required angles while maximizing the resulting image quality. The maximum number of angles required to match scanline imaging may be derived from the angular spatial frequency defined by the specific transducer properties:

$$a_i = \arcsin\left(i\frac{\lambda}{L}\right), \ i = -\frac{n_{lat}}{2}, \ldots, \frac{n_{lat}}{2} - 1 \quad (8)$$

with L being the overall lateral transducer array length, $n_{lat}$ being the number of transducer elements, and $\lambda$ being the wavelength determined by the transmit pulse frequency $\lambda = cf$. From this definition, the maximum angle $\alpha_{max}$ for a symmetric transmit sequence yields:

$$a_{max} = \arcsin\left(\frac{n_{lat}\lambda}{2L}\right) \quad (9)$$

Similarly, the number of planewave angles $\alpha_i$ to match the quality of a classical focused scanline-based image is determined by:

$$n = \frac{L}{\lambda F} \quad (10)$$

with F as the characteristic F-number determining the directivity of the transducer array $$\left(F = \frac{y}{2a}\right).$$

For an ultrasound transducer with a total length of L=11.5 mm operating at 12.5 MHz ($\lambda$=0.1232 mm), this results for example in 38 angles to match classical scanline imaging. In practice, however, a lower number of transmits is still sufficient to allow for anatomical imaging of high quality.

Based on an empirical evaluation for the system, 30 angles are considered in moving forward as sufficient to match the image quality of traditional focused imaging. By combining the transmit cycles of 30 angles with a specific receive subgrouping of consecutive 30 angles in a moving window (for example, see FIG. 15), one can reconstruct high quality ultrasound data while maintaining the maximal achievable imaging rate only limited by the physical constraints determined by acoustic waves traveling from the transducer surface into the tissue and back. This is in contrast to an example where each reconstructed 2D image may have one full transmit-receive cycle with n angles. Hence, in contrast the original formulation of planewave imaging in Eq. (2), the imaging rate relates to:

$$f_{2D} = \frac{c}{(2d)} \quad (11)$$

$$t_{2D} = \frac{(2d)}{c} \quad (12)$$

resulting in $f_{2D}$=19.25 kHz for a target penetration depth of 40 mm. This may lay the foundation for ultrafast rotational imaging, where imaging sequences are acquired with high update rates rotationally around the catheter to provide 3D+t imaging.

The imaging techniques may allow for the reconstruction of image data with both superior image quality and high imaging rates. The catheter may employ coherent planewave compounding, where multiple planewave transmit cycles are used to receive echoes allowing for the reconstruction of image data with high signal to noise ratio. While the anatomical imaging principle described above may be applied directly when the transducer position is static, respective motions may be considered for the case of fast positional changes of the imaging array. In this context, o represents the angular position of the imaging array around its axis for a side-looking catheter array rotating around its longitudinal axis.

Figure 14:
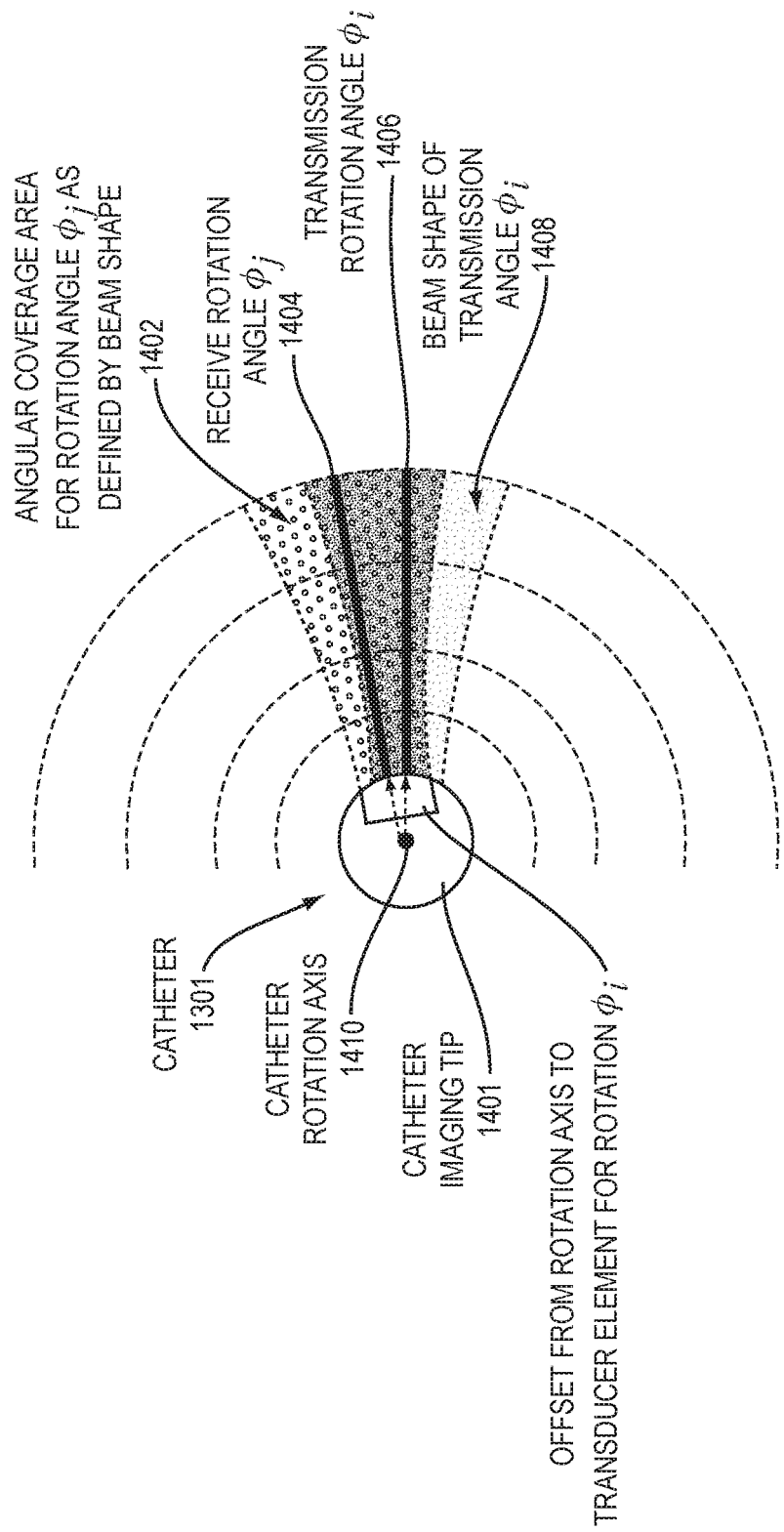
FIG. 14 is an illustration of a rotating catheter with simultaneous transmits and receive, in accordance with one embodiment of the present invention.

Following this rotational concept, the beamforming methods for ultrasound imaging with the proposed catheter system are modified to consider that both the catheter rotation angle ø as well as the plane wave tilt angle α may vary between transmitted and received echoes. FIG. 14 depicts the overall concept for a rotation catheter system in a top view (plan view). To consider this the rotational shift in the beamforming process, reconstruction may be directly performed in 3D space. Alternatively, a single planewave transmit-receive cycle (i.e. a fixed α) may also be assumed to be static, and a final image is reconstructed by compensating subsequent rotational transmit-receive events into a compounded image (correction of separately beamformed 2D images).

Figure 13C:
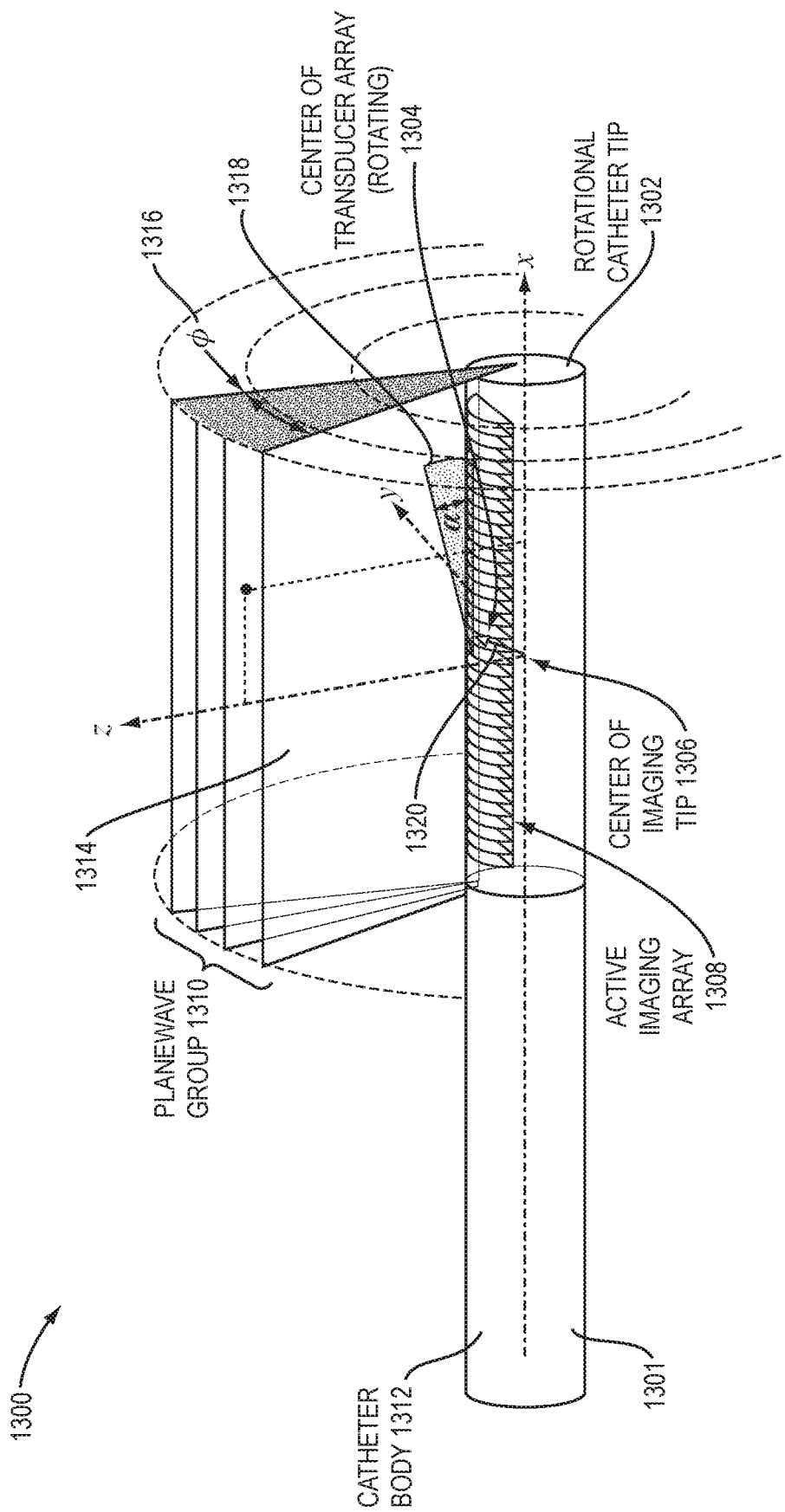

FIG. 13C is a schematic representation of transducer array 1300 within the acoustic/ultrasound housing, in accordance with one embodiment of the present invention. A catheter 1301 is shown with a catheter body 1312 comprising a proximal end and a distal end. The distal end of the catheter 1301 may comprise a catheter tip 1302. The catheter tip 1302 may be rotatable at different speeds. The catheter tip 1302 may include an ultrasound transducer array 1314 enclosed within an acoustic housing and extending along a longitudinal axis, x, of the catheter with center of imaging tip 1306. The ultrasound transducer array 1314 may comprise an active imaging array 1308 comprised of transducer elements (or acoustic transducers) configured to emit acoustic signals into a medium. From a single rotation around its longitudinal axis, x, the catheter 1301 may provide one full reconstructed 3D volume. The rotational resolution is thereby determined by the angle ø 1316 between each individual 2D image plane of image planewave group 1310. The center of the transducer array 1304 may rotate as the catheter rotates along its longitudinal axis, x.

The distal end of the catheter may be inserted into and guided to a site of a procedure in a medium. For example, the catheter may be inserted into the heart to aid in monitoring an ablation procedure. Upon activation, the ultrasound transducer array 1314 may be rotatable within the acoustic housing while transmitting ultrasound pulses and receiving ultrasound echoes from the surrounding medium.

The catheter, including the array of acoustic transducers of transducer array 1314, may rotate circumferentially about a longitudinal axis of the catheter, represented by axis x. Upon rotating circumferentially about longitudinal axis, x, the catheter may be positioned at an angle 1316 about the x-axis.

Upon rotating, the catheter may transmit, by an array of acoustic transducers at a set of different transmission angular positions (angle α, 1318) a plurality of incident acoustic wave signals representative of one or more plane waves of plane wave group 1310. The planewave group 1310 may aid in depiction of a 2D image or 3D image over time.

FIG. 14 is an illustration of the catheter 1301 of FIG. 13 from a view extending through the x-axis to illustrate the transmission angular position of the acoustic transducers, in accordance with one embodiment of the present invention. As the catheter 1301 is rotating continuously around its longitudinal axis, x, transmit and receive rotational angles may be different to each other, and one receive position reconstruction may include echo data from multiple transmit rotation positions. The catheter 1301 may have an angular coverage area 1402 for rotation angle defined by beam shape receive rotation angle ø 1404, transmission rotation angle ø 1406, and beam shape of transmission angle 1408 corresponding to catheter rotation axis 1410 of catheter imaging tip 1401. The angular coverage area 1402 may be offset from a catheter rotation axis 1410 to transducer element for rotation $ø_i$.

Because, in some embodiments, the transmission and reception angular positions may differ, beamforming may need to be rotationally corrected. To rotationally correct the beamforming, the definition of $\tau_{tx}$ and $\tau_{rx}$ may be extended to include varying rotational angles around the catheter as shown in equation (13), equation (14), and equation (15) below:

$$\tau_{tx}(p_k, \alpha, ø) = \frac{(p_k - m_ø) \times d_{\alpha ø}}{c} \quad (13)$$

$$m_ø = (0, r\cos(\varphi ø), r\sin(ø))^T \quad (14)$$

$$d_{\alpha ø} = (\cos(\alpha), \sin(\alpha)\cos(ø), \sin(\alpha)\sin(ø))^T \quad (15)$$

where:
$m_ø$ is the rotation-dependent center of the transducer array,
r the offset of the transducer elements to the catheter rotation axis, and
$d_{\alpha\omega}$ the direction of the tilted and rotated planewave.

On this basis, the receive delay may be determined by solving equation (16):

$$\tau_{rx}^2 c^2 = (y_k - \delta_y)^2 + (z_k - \delta_z)^2 + (x_k - \delta_x)^2 \quad (16)$$

where
$\delta_x$ is the location of the receiving element along the array, while $\delta_y$ and $\delta_z$ depend on $\tau_{rx}$ themself, as the catheter continues to rotate with $\omega = 2\pi f_{3D}$ to provide equation (17):

$$\delta_y = \cos(ø + \omega \tau_{rx})^* r, \delta_z = \sin(ø + \omega \tau_{rx})^* r \quad (17)$$

Together, $\delta_x, \delta_y,$ and $\delta_z$ may represent the vector pointing from the imaging origin to the specific lateral imaging transducer in 3D space. Following this definition, the incrementally changing rotation angle of the catheter may be directly included into the delays for each reconstructed RF, yielding an image for an ultrafast rotating catheter incorporating both the catheter rotational angles as well as lateral planewave tilts, as shown in equation (18) below:

$$I(x_k, y_k, \alpha, ø) = \sum_{i_{lat} \in a} C(i_{lat}, \tau(x_k, y_k, \alpha, ø, i_{lat})) \quad (18)$$

Figure 15:
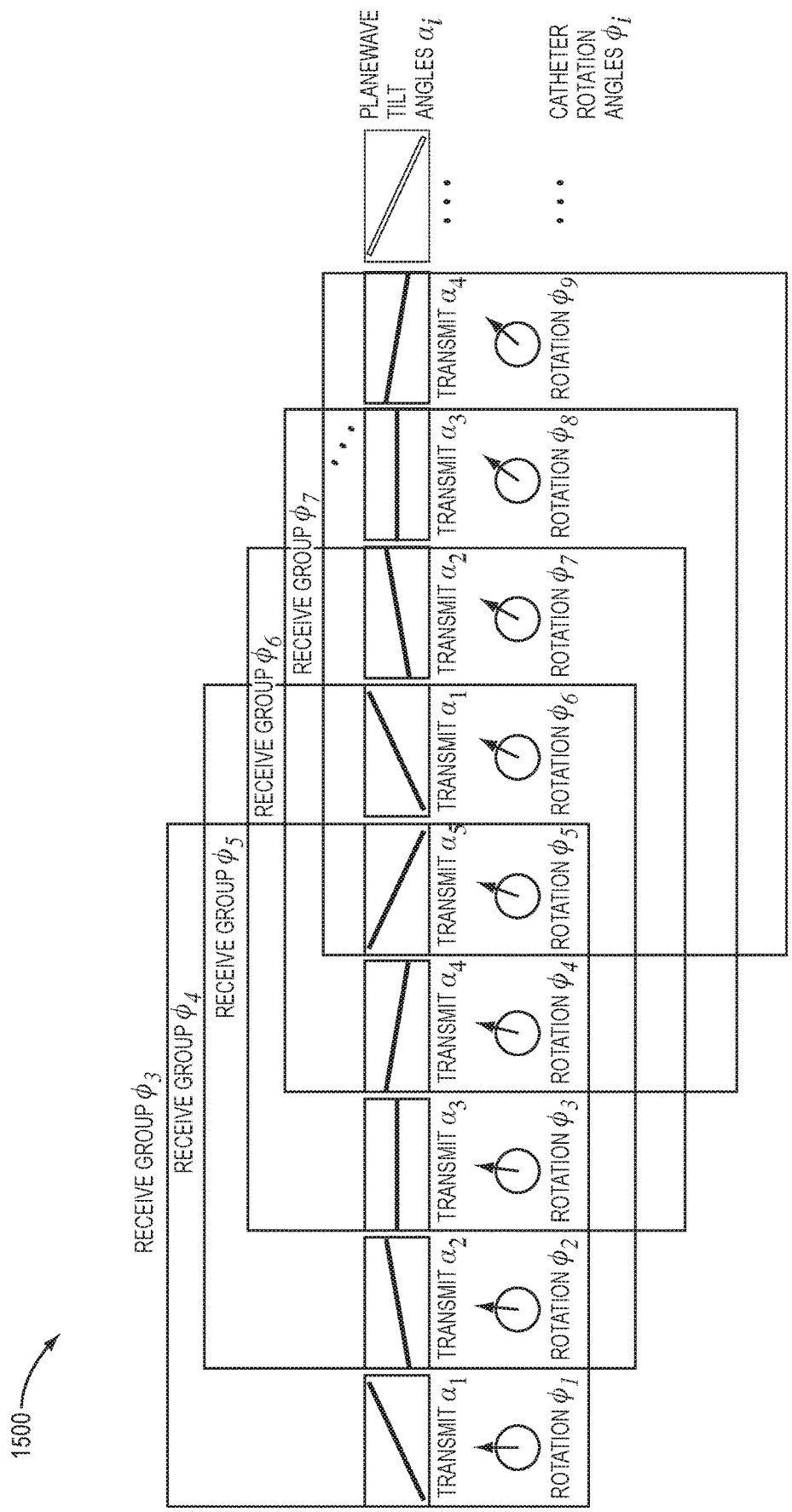
FIG. 15 is an illustration of ultrafast 3D planewave sequence, in accordance with one embodiment of the present invention.

FIG. 15 is an illustration of the ultrafast 3D planewave sequence, in accordance with one embodiment of the present invention. For rotational acquisitions, a series of planewave tilt angles $\alpha_i$ may be augmented by the continuous rotation of the catheter around its axis ø. Effectively, for each catheter rotational position, a receive group may integrate tilted planewaves in both planewave tilt angle α and catheter rotation angle ø, yielding an adaptive 3D planewave coherent compounding strategy.

As the approach described above may not allow for an explicit formulation of the receive delays, beamforming of the same low-resolution images is implicitly required multiple times. Thus, it may be beneficial to only approximate the correction for the rotation of the catheter and consider each individual transmit-receive cycle (for a single planewave) as static case. In this, the process of acquiring one low-resolution image as in Eq. (6) is considered to take place with a static catheter. On this basis, to account for the rotational movement of the catheter between successive tilted planewave emissions, the rotation of the catheter is taken into account for the approximate compounding by modifying equation (18), as shown in equation (19) below:

$$I_{2D}(x_k, y_k, ø) = \sum_{i=1}^{n} I(x_k, y_k + r(\cos(ø - ø_i) - 1), \alpha_i) \quad (19)$$

Figure 16:
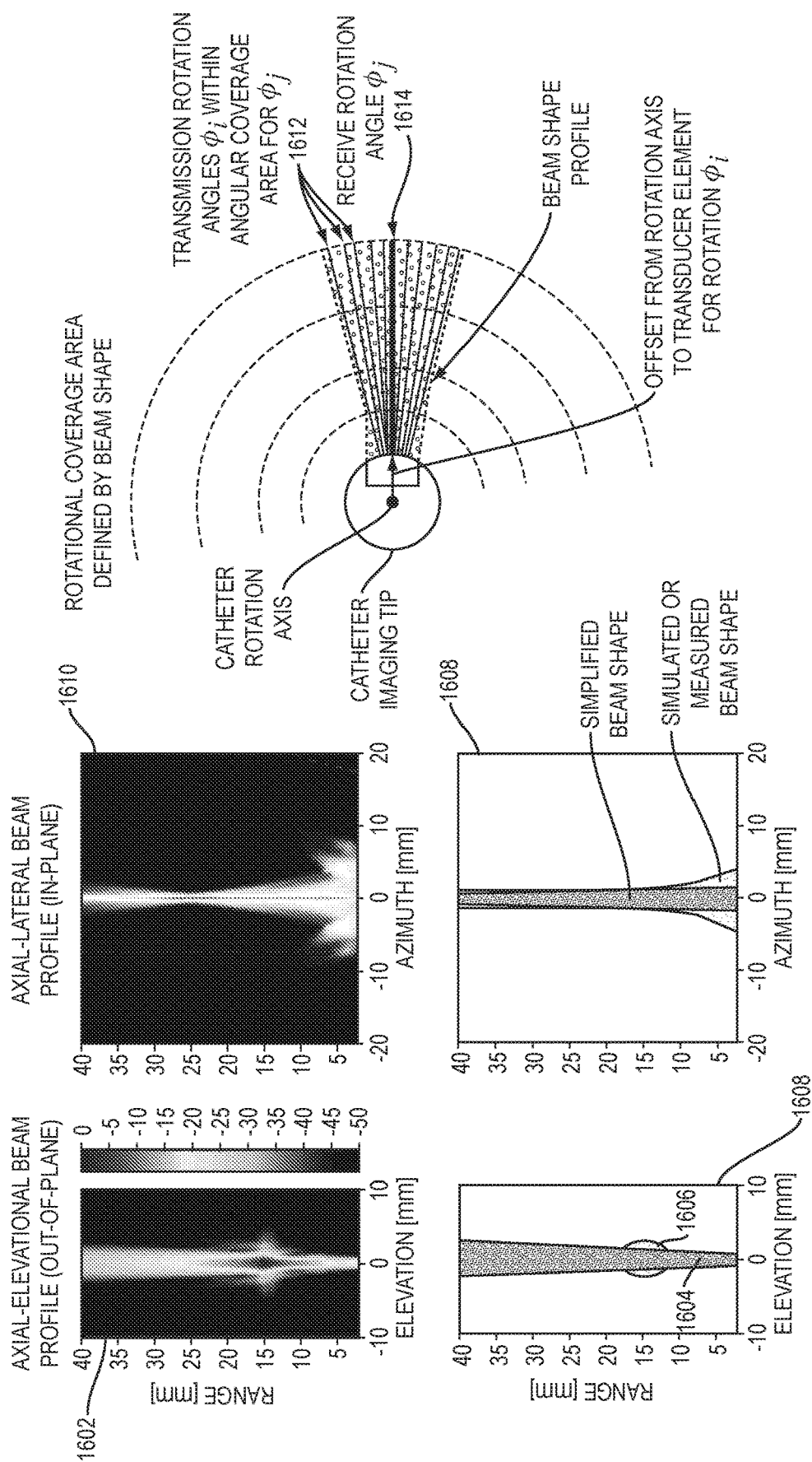
FIG. 16 is an illustration of parametrization of angular coverage, in accordance with one embodiment of the present invention.

FIG. 16 is an illustration of the parametrization of angular coverage, in accordance with one embodiment of the present invention. The beam shape (pressure profile of acoustic wave in 3D) of an ultrasound imaging system may be simulated or measured in axial-lateral 1602 and axial-elevational 1610 dimensions using simulation environments for ultrasound wave propagation, or experimental techniques such as pressure field measurements using hydrophones. Using a −30 or −60 dB cut-off, beam shapes may derived directly 1604, or used to retrieve a simplified definition of the coverage areas such as trapezoid shapes, angular or rectangular shapes 1606 from the cut off area of the beam profile (areas in 1608). These coverage areas may be used to select a neighborhood around each target receive position 1614 in which all received echoes from different transmit positions 1612 may be included into the reconstruction process (right).

With respect to this 3D rotational coherent planewave compounding with the methods described above, the angular aperture (e.g., all transmit-receive data to be considered for compounding depending on its angular distance to the central target image plane) may be defined manually or based on the elevational and lateral width of the ultrasound transmit beam. Thereby, the beam shape may be determined by the ultrasound transducer array properties as well as the specific imaging parameters. In practice, the beam shape in elevational direction (thickness) may be, for example between 0.5 mm and 5.0 mm and diverges in deeper tissue regions. In this regard, depending on the angular rotational speed and the 2D acquisition rates, a varying number of planewaves may be considered for 3D coherent compounding both angles α, ø. To select planewaves to be considered for the beamforming of a specific catheter rotation speed, a measured or simulated beam profile may be used to identify neighboring transmits falling in this coverage area (see FIG. 16 for a graphical representation). Alternatively, simplified coverage areas may be defined (e.g trapezoid 1604 or circular arc defining the coverage area in axial, lateral and elevational dimensions shown in graphs 1602 and 1610) to allow for an analytic/geometric determination of covered planewave transmit and receive events. Assuming a beam shape definition as circular arc (angle span around a specific catheter rotary position), FIG. 17 shows an exemplary consideration of the number of planewaves used for the reconstruction centered at each individual angular position assuming a 2D imaging rate of $f_{2D} = 19.2$ kHz. Following this, a beam resolution of 5 mm (realistic for unfocused planewaves) allows for example up to n=⌊38.20⌋=38 transmit angles to be considered for an imaging depth of 40 mm. From this example and the general formulation, it may be seen that this approach not only integrates additional information into the reconstruction (beamforming), but may also enable the utilization of planewave coherent compounding and ultrasound imaging with fast rotating ultrasound arrays in general.

FIG. 17 is a table of angular distance between slices (frames) and number of planewave transmits used for 3D compounding, in accordance with one embodiment of the present invention.

With a 2D imaging rate of 19.2 kHz, for example, the achievable imaging resolution may be limited by the distance of individual frames acquired rotationally around the catheter and may decrease with the distance to the transducer (reflected in table 1702) as well as with higher rotation speed. Depending on the spatial beam width in elevational directions, a series of planewave transmits may be used for beamforming and 3D coherent compounding, reflected in table 1704.

Improved Procedure Monitoring

In some embodiments, imaging catheters may be utilized for lesion map reconstruction by imaging an area before and after a procedure, comparing the results and identifying differences. This can help clinicians/doctors evaluate the success of their procedure.

Figure 18:
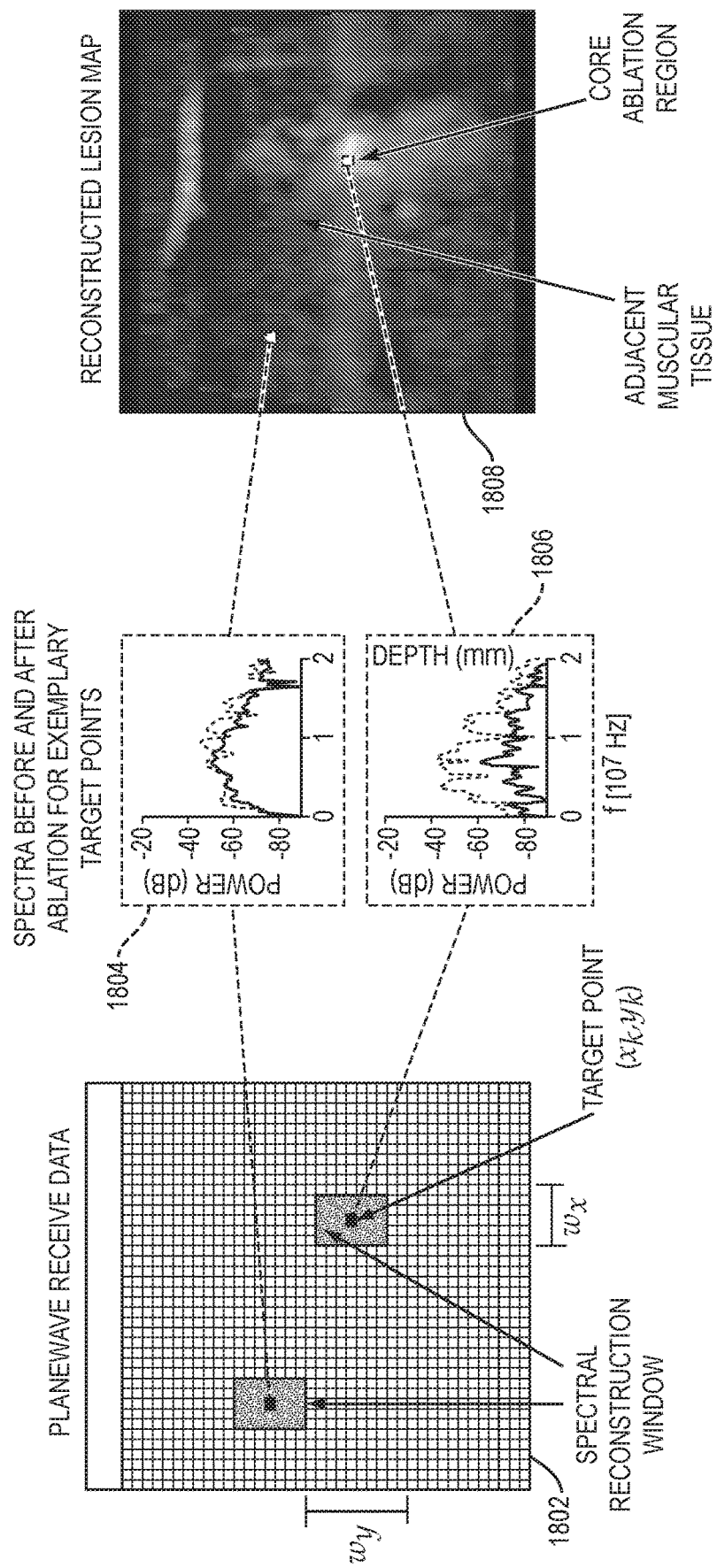
FIG. 18 is an illustration of lesion map reconstruction, in accordance with one embodiment of the present invention.

FIG. 18 is an illustration of an exemplary lesion map reconstruction process, in accordance with one embodiment of the present invention.

Assuming a planewave sequence with n transmits, angles are defined in a symmetric way, as shown in equations 20, 21 and 22 below:

$$\alpha_i = \left(\frac{2i}{n} - 1\right)\alpha_{max}, i = 0, \ldots, n \quad (20)$$

$$a_{max} = \arcsin\left(\frac{n_{lat}\lambda}{2L}\right) \quad (21)$$

$$I(x_k, y_k, \alpha) = \sum_{i_{lat} \in a} C(i_{lat}, \tau(x_k, y_k, \alpha, i_{lat})) \quad (22)$$

and $\alpha_{max}$ defined according to Eq. (22). From each individual set of echoes received per (titled) transmit planewave, raw radio-frequency data is reconstructed into individual sub-images $I(x_k, y_k, \alpha_i)$ through beamforming following Eq. (22). The sub-Image 1802 is an example of a mapping of planewave receive data for a particular transmit plan wave. Next, for each target point $p=(x_k, y_k)$ of the sub-image, a localized frequency-domain representation may be reconstructed. To extract a frequency-domain representation for each acquisition, a window with lateral and axial sizes $w_x$, $w_y$, centered around each target point p may be employed to retrieve a sample-set of RF data in axial and lateral directions. Following Eq. (22) data in axial direction corresponds to beamformed samples recorded in axial direction by one or multiple transducer channels with a sampling rate $f_s$. Thus, a spectral representation may be derived from each axial sample set $\in[y_k-w_y/2; y_k+w_y/2]$, where different methods may be employed to retrieve a local frequency-domain representation from the sample set, with suitable frequency-domain transforms being the Fourier transform, the Laplace transform, the Z transform, or the Wavelet transform. For each RF dataset reconstructed from a single planewave transmission, localized power spectra may be reconstructed for each point within the image from a window centered around each which may yield local spectra estimated frequency spectra 1804 and local spectra estimated frequency spectra 1806 for exemplary target points.

Figure 19:
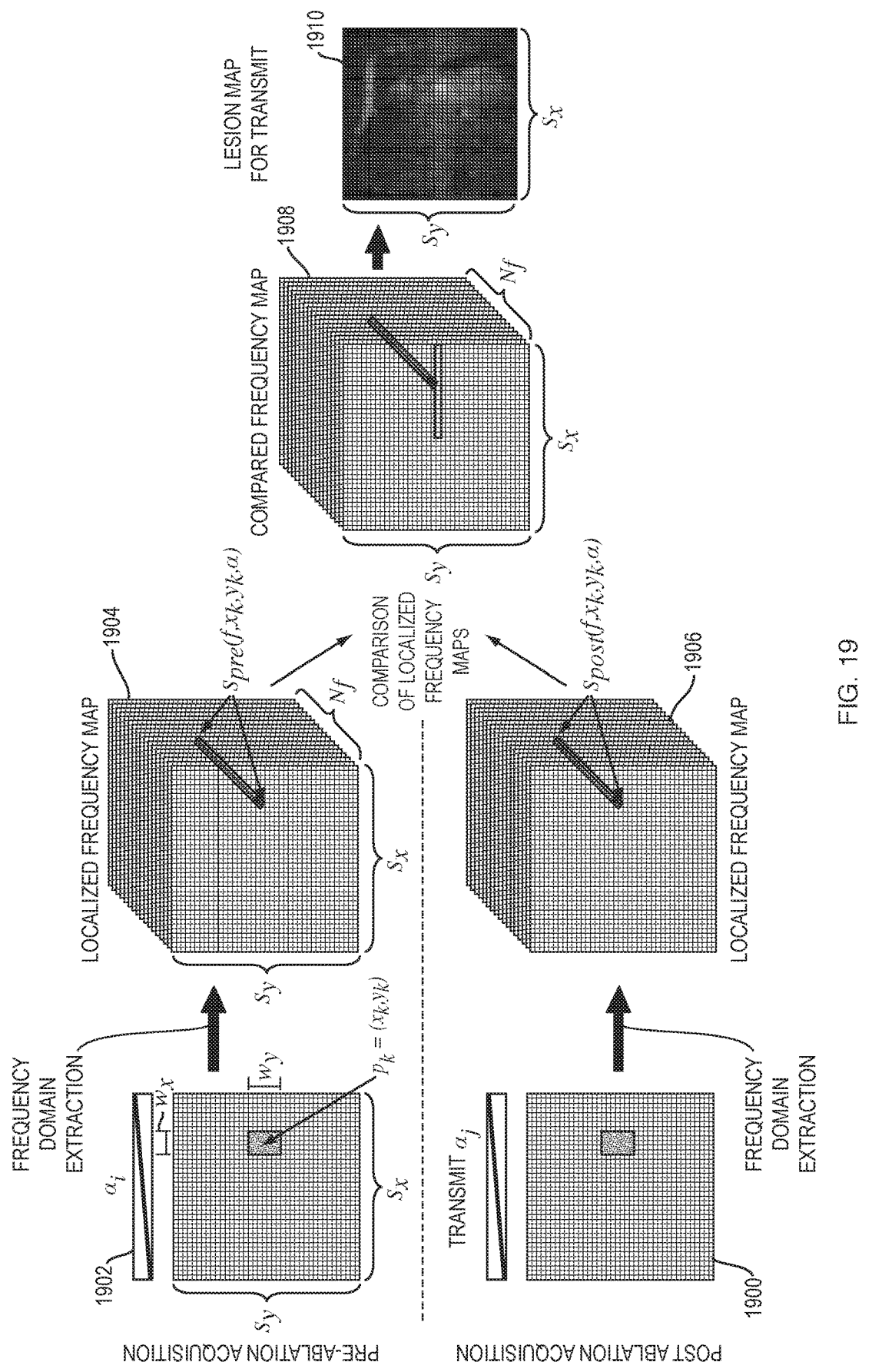
FIG. 19 is an illustration of exemplary lesion map, in accordance with one embodiment of the present invention.

In some embodiments, the imaging system may retrieve local frequency-domain representations for each target point (or pixel) of one or more sub-images before and after a procedure (e.g., ablation procedure), allowing for the differentiation of ablated from non-ablated regions through specific changes in characteristics of target point in the frequency-domain representation. As the evaluation of the frequency-domain representations from a single acquisition may not only contain the specific frequency-content of the target tissue but also other external factors such as the imaging pulse, instrumentation, overall attenuation in tissue etc., frequency-domain representations before and after one or multiple ablations are reconstructed. For example, FIG. 19 depicts pre and post ablation acquisition as well as a comparison of frequency maps. From these representations before and after ablation, specific comparisons may be employed in the time and frequency domains to retrieve specific information about the tissue and its changes after ablation with respect to the pre-ablation acquisition (see FIG. 19 for a graphical representation).

Initially, sub-images, such as sub-images 1900, 1902 representing a mapping of planewave receive data for a particular transmit plan wave are obtained for pre-ablation acquisition and post ablation acquisitions.

Figure 20:
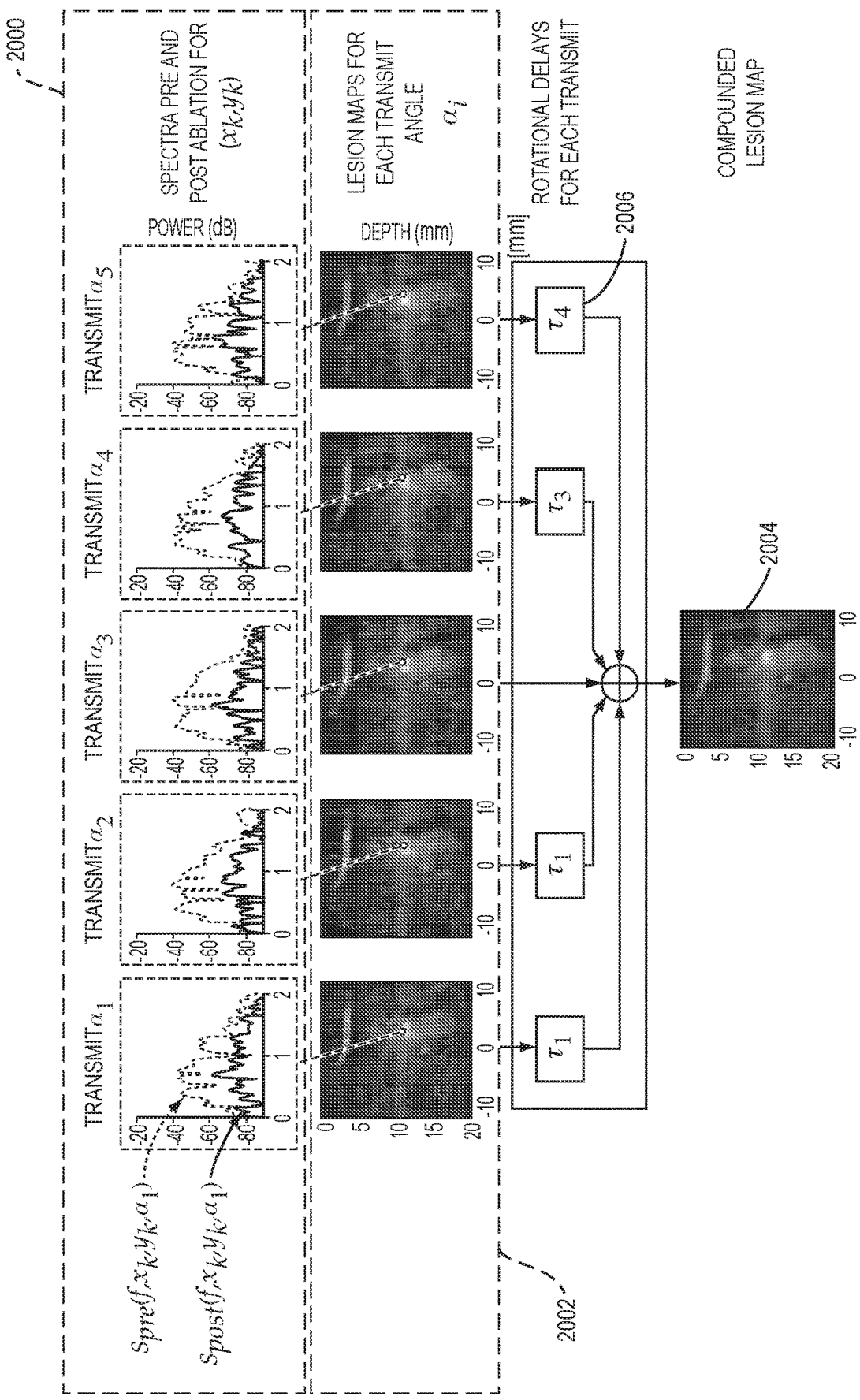
FIG. 20 is an illustration of lesion map compounding, in accordance with one embodiment of the present invention.

The pre-ablation localized spectra $S_{pre}(f, x_k, y_k, \alpha)$ 1904 related to one or more pre-ablation sub-images 1902 and post-ablation localized spectra $S_{post}(f, x_k, y_k, \alpha)$ 1906 related to one or more pre-ablation sub-images 1900 may be retrieved for each set of corresponding points $p_k$ using e.g., a Power Spectrum estimator (using fast Fourier transforms or autoregressive estimation methods) for each target position and angle $\alpha$. Thereby, the frequency $f \in [0, f_s/2]$ may be limited by the sampling frequency $f_s$ of the input data. To reconstruct a lesion map 1908 $L(x_k, y_k, \alpha_i)$, the ratio of spectral parameters pre and post ablation in dB are used to directly reconstruct a measure of overall spectral changes at each coordinate due to the ablation $$L(x_k, y_k, \alpha_i) = \sum_{f=0}^{\frac{fs}{2}} \frac{10\log_{10}(S_{pre}(f, x_k, y_k, \alpha_i))}{10\log_{10}(S_{post}(f, x_k, y_k, \alpha_i))} \quad (23)$$

where for each set of angles before and after ablation the ratio of localized spectra is calculated. To this end, the contributions of all planewave tilts $\alpha_i$ may be compounded into a single reconstructed lesion map 1908, under consideration of the catheter rotational position following the reconstruction approach in Eq. (24) and (25):

$$I_{2D}(x_k, y_k, \emptyset) = \sum_{i=1}^{n} I(x_k, y_k + r(\cos(\emptyset - \emptyset_i) - 1), \alpha_i) \quad (24)$$

$$L_{2D}(x_k, y_k, \emptyset) = \sum_{i=1}^{n} L(x_k, y_k + r(\cos(\emptyset - \emptyset_i) - 1), \alpha_i) \quad (25)$$

with $\alpha_i$, $\varphi_i$ the tilt and rotation angles for transmission i, and r the distance of the transducer surface to the rotation axis of the catheter (see FIG. 20).

FIG. 20 is an illustration of lesion map compounding, in accordance with one embodiment of the present invention. From a series of planewave transmit angles $\alpha_i$, individual localized spectral estimates are generated, providing angular estimates for each target point before and after ablation, 2000. These angular estimates may then be compounded into a single lesion map, 2002 under consideration of the different catheter rotation angles ø of the different transmits.

While the reconstruction in Eq. (23) and Eq. (24) demonstrate a specific example using a power spectrum estimator, the comparison of acquisitions before and after ablation may be realized in different forms. The key consideration for the present approach is that a frequency-domain representation may be employed for each point in space before and after ablation in order to detect local changes of the tissue state after ablation with respect to before ablation. In quantitative ultrasound imaging, spectral parameters may also be reconstructed locally for each point in space; however, common methods for instrument calibration (e.g. reference phantom method, planar reflector technique) are rendered inapplicable for highly heterogeneous tissue or dynamic acquisitions such as within the heart. In this regard, by employing a direct comparison of acquisition of the same region of interest before and after ablations, one may compensate for specific characteristics of the instrumentation and specifically focus on local changes of tissue between the evaluated acquisitions. In this regard, the comparison may be employed also with other mathematical operations, and may also include a direct comparison of frequency-domain features with techniques such as machine learning (e.g. convolutional neural networks considering frequency-domain representations).

Resolution-Preserving 3D Reconstruction

Following the reconstruction of $I_{2D}(x_k, y_k)$ and $L_{2D}(x_k, y_k)$ individually per 2D ultrafast transmit sequence acquired rotationally around the catheter axis, 3D anatomical and functional volumetric data may be reconstructed through a resolution-preserving 3D reconstruction approach.

During data acquisition, the specific 3D pose (position and orientation) of the respective imaging plane may be acquired for each input planewave transmit-receive cycle. This pose may be generated from either the rotational motor position, a dedicated tracking sensor (e.g. electromagnetic tracking, rotary encoders), or a combination of those. Using this 3D pose and its relation to the 2D image, the position $(x_k, y_k)$ of each 2D image point (e.g. anatomical or functional data) can be retrieved in 3D space, and may be indicated as sample position $s_j=(s_x, s_y, s_z)$. Thereby, the homogeneous transformation from the 2D image coordinates to the respective 3D sample position may be determined by the calibration of the ultrasound image position with respect to the tracking information (determined by mechanical construction) and the current 3D pose retrieved from the tracking data.

To reconstruct a 3D volume from a series of 2D input images with respective pose formation, a resolution preserving 3D reconstruction may be employed. Inspired by [13], all samples used to reconstruct a specific target voxel value are selected first. To do so, the field of view covered by the physical ultrasound beam is employed to select all samples within this space in 3D. For a desired target voxel, $v_i=(v_x, v_y, v_z)$, S is given by all samples which are lying inside an ellipsoid-region around $v_i$, where the ellipsoid is defined according to the specific coordinate spaces of the input samples $s_j$ and the maximum ultrasound beam dimensions $d_x$, $d_y$, $d_z$ in lateral, axial, and elevational direction $$\frac{(v_{i,x}^{s_j} - s_{j,x})^2}{d_x^2} + \frac{(v_{i,y}^{s_j} - s_{j,y})^2}{d_y^2} + \frac{(v_{i,z}^{s_j} - s_{j,z})^2}{d_z^2} \leq 1 \quad (26)$$

where the maximum distances $d_x$, $d_y$, $d_z$ can be selected based on the resolutions of planewave transmits in the different directions (see FIG. 20).

Following this sample selection, the respective value $U(v_i)$ of each target voxel may be reconstructed by an inverse distance weighting of the input sample intensities with respect to their distance to the target voxel. It is important to note, however, that based on the set of selected samples per voxel, various other interpolation schemes can be employed (e.g. nearest neighbor interpolation, spline fitting, or Gaussian weighting), thus enabling an adaptable 3D+t reconstruction approach.

To this end, the interpolation yields the reconstructed 3D value for each target voxel position, which allows for the reconstruction of an isotropically spaced 3D volume from the series of input 2D images with pose information. In general, this reconstruction approach may be independent of the specific input data, i.e. it can be applied to both the input 2D anatomical data $I_{2D}(x_k, y_k)$ as well as the functional data $L_{2D}(x_j, y_k)$ into respective 3D volumetric datasets $I_{3D}$ and $L_{3D}$.

Shear Wave Tracking in 3D

Figure 21:
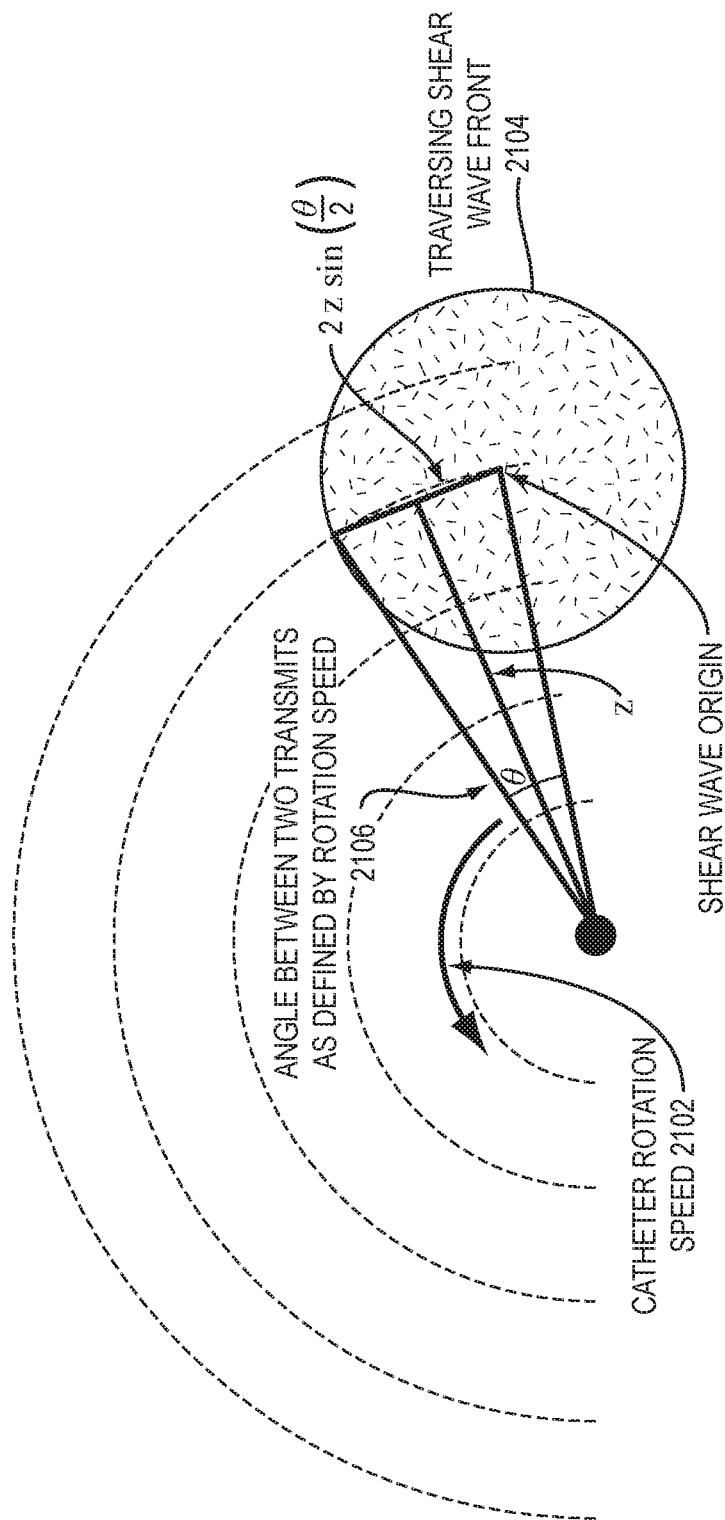
FIG. 21 is an illustration of 3D rotational shear wave tracking, in accordance with one embodiment of the present invention.

Further to the shearwave tracking description and corresponding FIGS. 2-3 mentioned above, in shear wave elastography, a long sequence ultrasonic pulse is used to induce a local deformation within the target tissue, which causes a shear wave propagating from the target point. This shear wave traverses the tissue 3D, opening up the way to track the wave directly in 3D using a rotational reconstruction scheme. As alternative to this acoustic-based induction of shear waves, other generators for shear waves can be used (e.g. external motors). While shear wave elastography (SWE) has been successfully employed for external 2D and 3D ultrasound imaging, the requirement to accurately track the propagation of shear waves as they traverse through tissue of varying elasticities poses specific challenges for a 3D rotational catheter concept. However, with a continuous acquisition of raw channel information (64 channels) at ultrafast imaging rates >10 kHz, the three-dimensional propagation of shear waves within the three-dimensional tissue can be retrieved from the observed raw data directly. In this respect, as shown in FIG. 21 the adaptive control of catheter rotation speed 2102 may be used to allow for the adaptive tracking of the shear wave speed in 3D of the shear wave front 2104, where the rotational speed may be matched to the shear wave speed. Common shear wave speeds in the heart are found in the range from 0.5 to $$S = \left\{ \frac{N}{j} \right\}$$

$$5 \frac{mm}{ms},$$

and also depends on the specific fiber orientation of the target myocardial tissue. Further to this, the distance $\delta_{SW}$ travelled by a shear wave front 2104 is directly related to the angle θ 2106 between two transmits as defined by rotation speed at a desired penetration depth, and thus also to the required rotation speed, as shown in the following equation:

$$\theta = 2\arcsin\left(\frac{\delta_{SW}}{2z}\right)\frac{180}{\pi} \quad (27)$$

where z is the distance from the transducer surface, and θ the angle between frames to match the travelling shear wave front 2104 around the catheter. From this relation, it can be observed that shear wave tracking in 3D may be enabled by a minimal rotation speed of $$0.7 \frac{°}{ms} (119 \text{ rpm}),$$

a maximal rotation speed of $$29.0 \frac{°}{ms} (4826 \text{ rpm}),$$

and an average rotation speed of $$8.3 \frac{°}{ms} (1383 \text{ rpm}).$$

This shows that the range of shear wave speeds in cardiac tissue may be covered at realistic depths and speeds when observed in vivo using a rotational catheter system (see FIG. 22).

FIG. 22 is a table of shear wave speed (similar to FIG. 3) and an equivalent rotational speed of the catheter, in accordance with one embodiment of the present invention. Indicated are the angular steps in degrees for common shear wave speeds and equivalent rotational speed in RPM, in the heart as observed radially around a catheter in depths between 10 and 40 mm.

While the evaluation discussed above has a focus on shear wave speed imaging, the same concept can be directly applied to myocardial strain imaging. In this regard, no shear wave is induced into the tissue, but rather the contraction of the heart muscle itself is used for estimation of tissue deformation. From these estimates, the strain of tissue (related to tissue stiffness) may retrieved from the compressional deformation estimates.

To track both the propagation of shear waves in 3D, as well as to estimate the deformations to cardiac tissue during myocardial contraction, rotational acquisitions around the catheter are recorded for a series of revolutions first. In this regard, raw signals are reconstructed first into 3D (continuously while the catheter is rotating), followed by scatterer tracking directly employed within the 3D volume. 3D-tracking is thereby provided analogous to conventional scatter tracking (e.g. autocorrelation, filter-based, based on machine learning, etc.) but employed directly on the rotational 3D data as acquired with varying rotational speeds.

Figure 23:
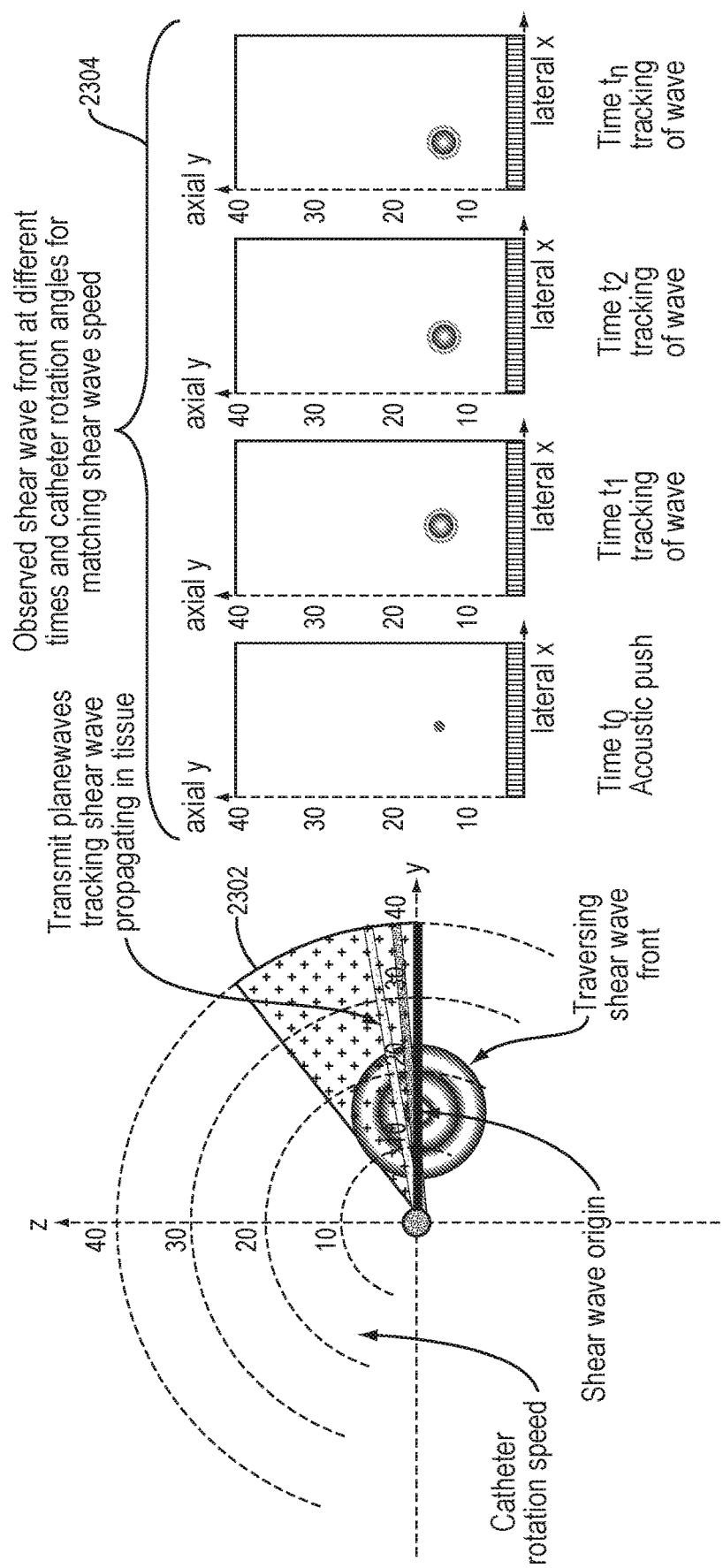
FIG. 23 is an illustration of volume-based shear wave imaging, in accordance with one embodiment of the present invention.

FIG. 23 is an illustration of volume-based shear wave imaging (similar to FIG. 3) while showing the propagation and angular coverage in more detail, in accordance with one embodiment of the present invention. For a dedicated set of rotary positions 2302 an acoustic push may be induced at depth 13 mm at $t_0$ as shown in graphic 2304. Over time ($t_1$ to $t_n$—graphics 2304), the shear wave may propagate within the tissue with a characteristic speed and may be tracked accordingly in reconstructed 3D data at appropriate speeds.

Imaging Catheter Calibration

Figure 24:
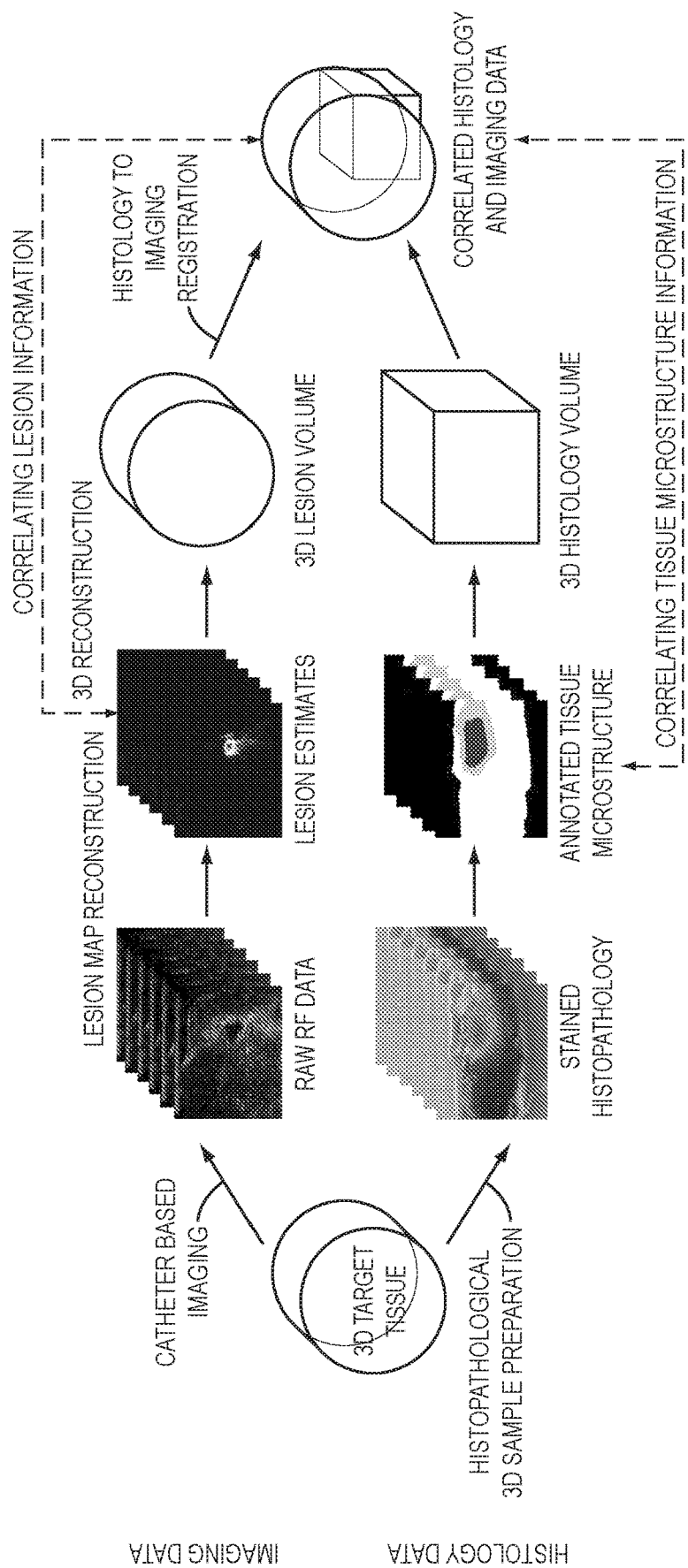
FIG. 24 is an illustration of calibration of lesion data using histology, in accordance with one embodiment of the present invention.

FIG. 24 is an illustration of calibration of lesion data using histology, in accordance with one embodiment of the present invention. Subsequent to the catheter-based imaging acquisitions for the reconstruction of lesion maps in 3D (as shown in FIGS. 18-19), the ablated tissue sample may be preserved, sliced and stained into a series of histopathological 2D images. These may be reconstructed into a labelled 3D volume representing the ground truth tissue microstructure. By registering the histopathological data to the imaging data, lesion information may be directly correlated and calibrated to allow for a direct mapping of tissue changes to the observed values of reconstructed lesion maps.

Methods

Figure 25:
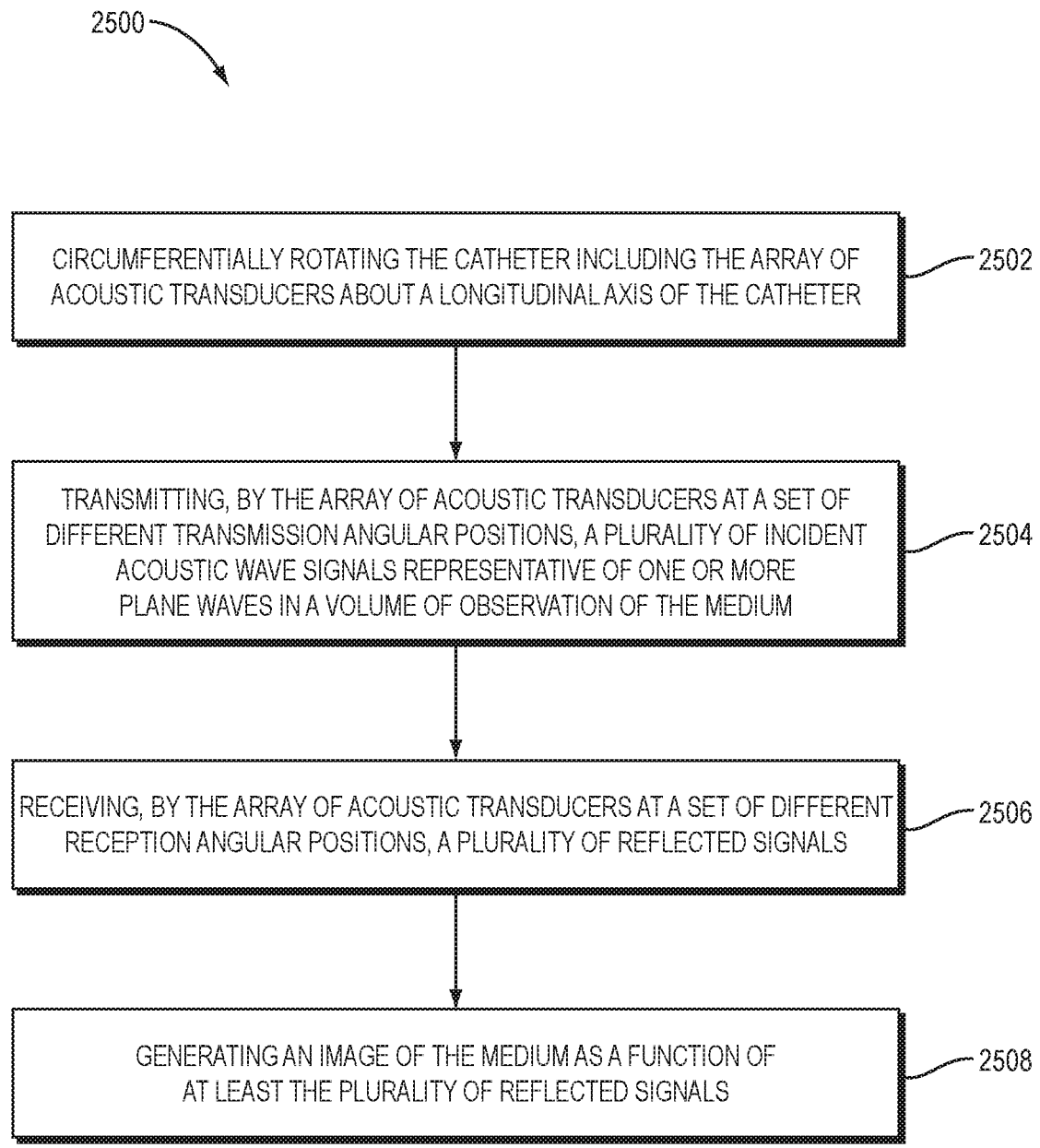
FIG. 25 is an exemplary illustration of a flow chart illustrating one embodiment of the present invention.
Figure 26A:
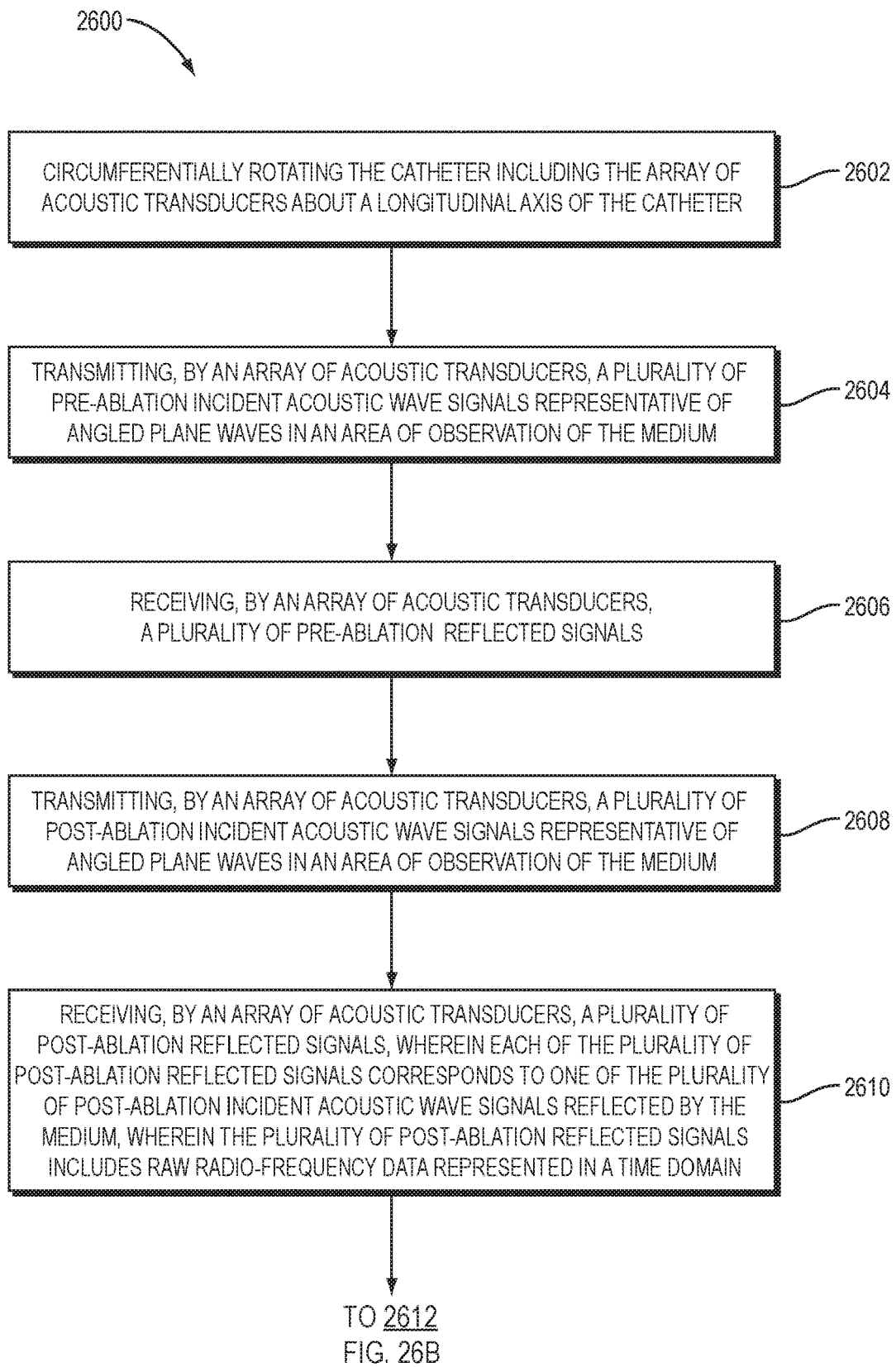
FIGS. 26A-26D is an exemplary illustration of a flow chart illustrating one embodiment of the present invention.
Figure 26B:
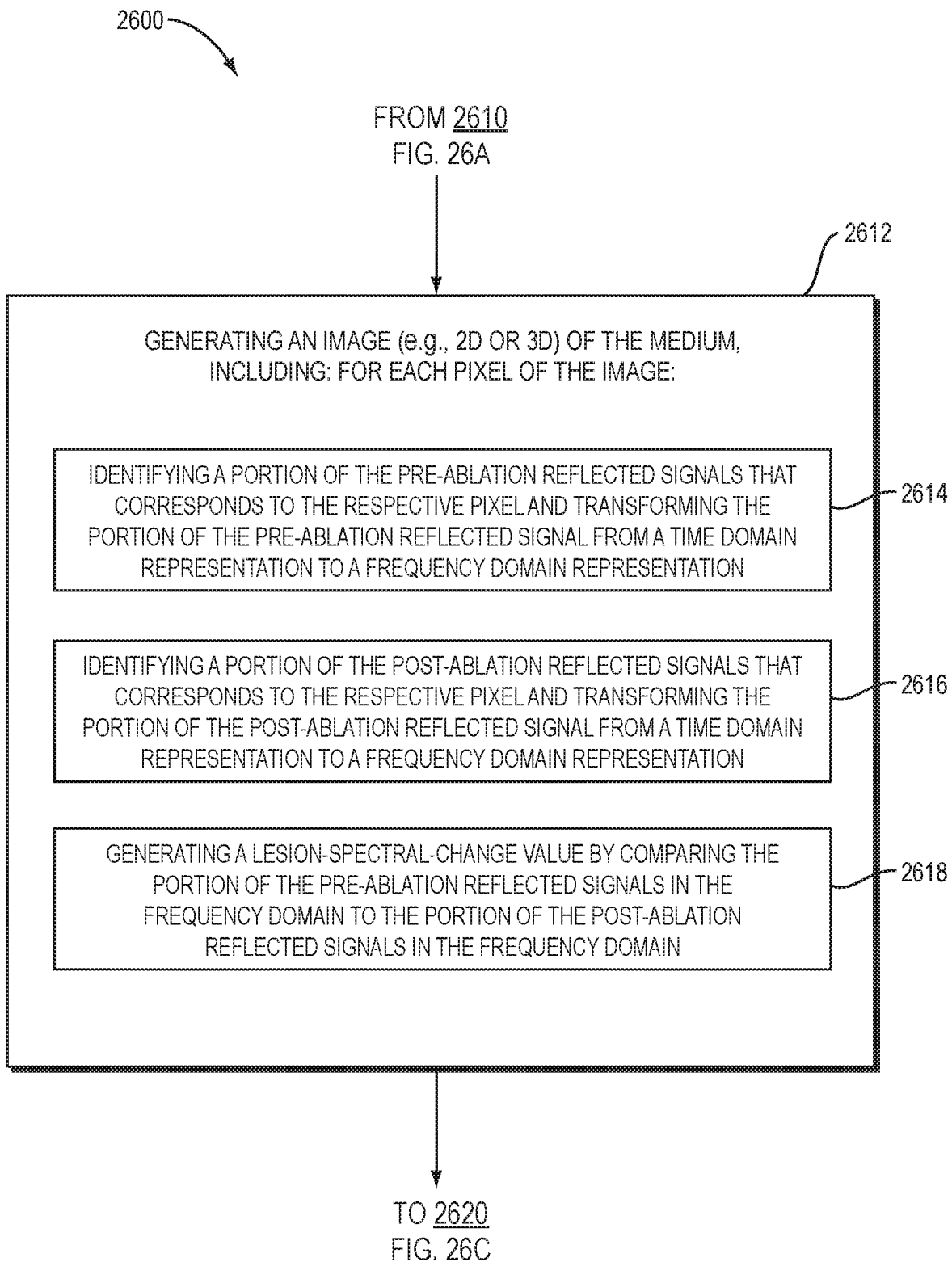
Figure 26C:
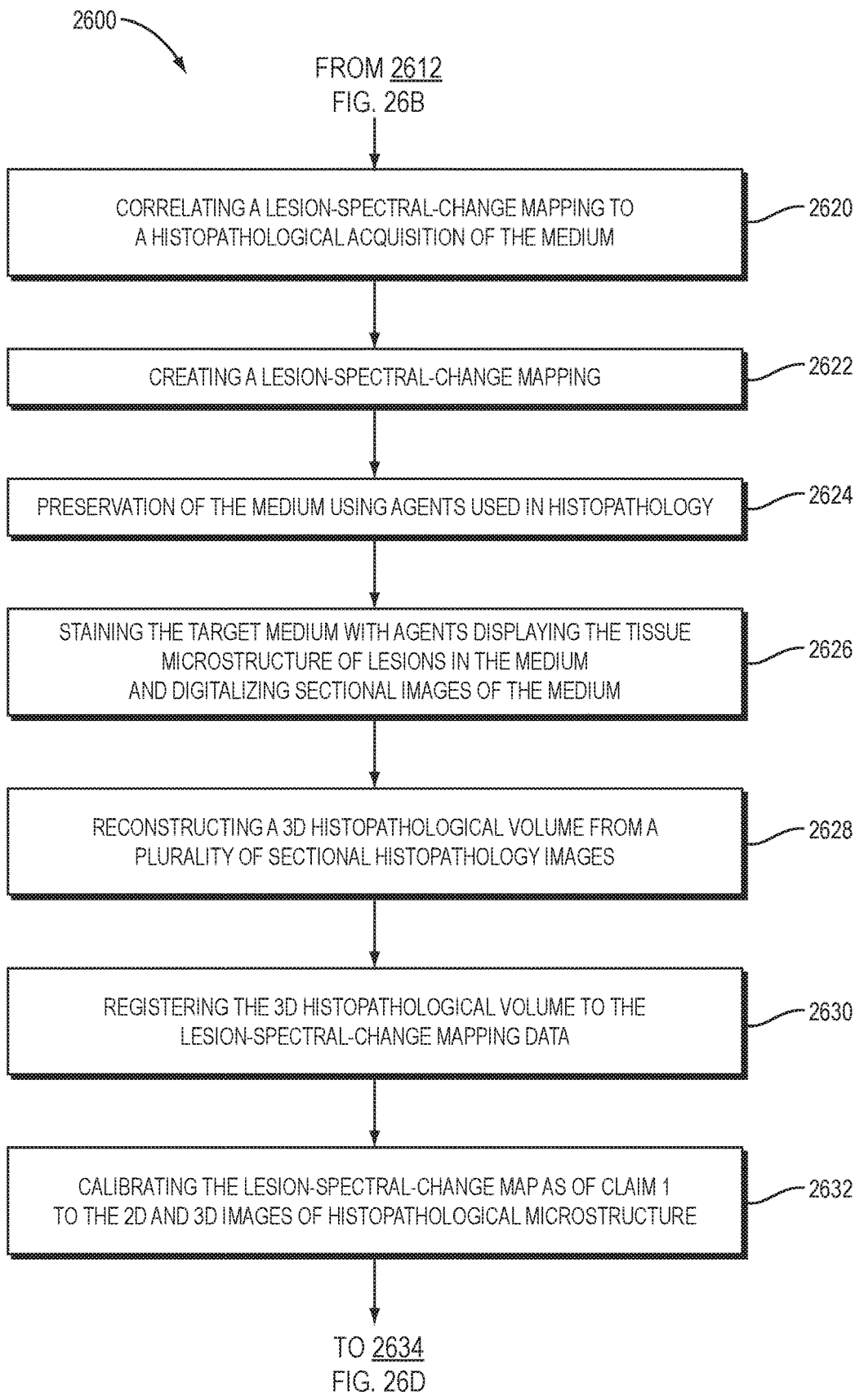
Figure 26D:
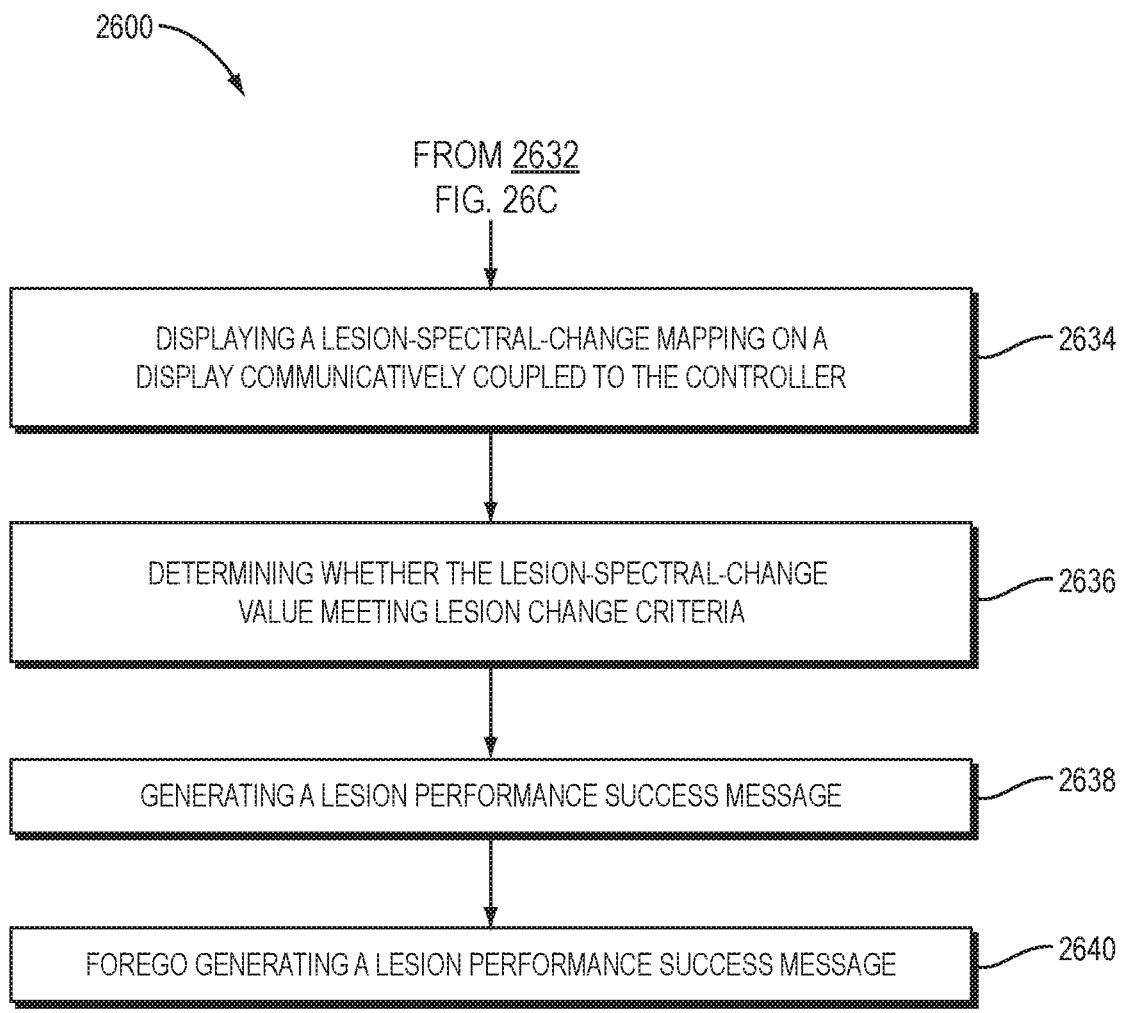

FIG. 25 is a flow chart, in accordance with a method for ultrasound imaging using an imaging system, in accordance with one embodiment of the present invention. The method 2500 may be implemented using a catheter (e.g., catheter 1301 shown in FIG. 13). The catheter 1301 may comprise a proximal end and a distal end, the distal end of the catheter comprising a catheter tip (e.g., rotational catheter tip 1302). The catheter tip may comprise an ultrasound transducer array (e.g., transducer array 1314) enclosed within an acoustic housing and extending along a longitudinal axis (e.g., axis x shown in FIG. 13 of the catheter). The distal end of the catheter may be configured to be inserted into and guided to a site of a procedure in a medium. The ultrasound transducer array (e.g., transducer array 1314) may be rotatable within the acoustic housing while transmitting ultrasound pulses and receiving ultrasound echoes from the surrounding medium.

A controller (e.g., console 402 in FIG. 5) may be communicatively coupled with the catheter (e.g., catheter 1301 shown in FIG. 13).

The method 2500 may comprise circumferentially rotating 2502 the catheter including the array of acoustic transducers about a longitudinal axis of the catheter (e.g., axis x shown in FIG. 13 of the catheter).

In one embodiment, while rotating the catheter, the method 2500 may comprise transmitting 2504 by the array of acoustic transducers at a set of different transmission angular positions, a plurality of incident acoustic wave signals representative of one or more plane waves in a volume of observation of the medium (e.g., as shown in FIG. 13C).

In one embodiment, the method 2500 may comprise receiving 2506 (e.g., receive group shown in FIG. 15), by the array of acoustic transducers at a set of different reception angular positions, a plurality of reflected signals. In one embodiment, each of the plurality of reflected signals corresponds to one of the plurality of incident acoustic wave signals reflected by the medium, wherein at least one of the plurality of reflected signals may be received by the array of acoustic transducers at a reception angular position that is different than the transmission angular position (e.g., transmit αi shown in FIG. 15) of the corresponding transmitted incident acoustic wave signal.

In one embodiment, the method 2500 may comprise generating 2508 an image of the medium as a function of at least the plurality of reflected signals, and for at least one of the respective reflected signals: (a) the transmission angular position of each of the acoustic transducers for the incident acoustic wave signal that corresponds to the respective reflected signal and (b) the reception angular position of each of the acoustic transducers for the respective reflected signal. In one embodiment, the reception angular position of the acoustic transducers for the respective reflected signal is different than the transmission angular position of the acoustic transducers for the respective reflected signal (e.g., as disclosed in Eq. 18).

In one embodiment, generating an image of the medium as a function of at least the plurality of reflected signals includes: for each of the respective reflected signals: (c) an angle of the plane wave; and (d) a rotational angle of the catheter (e.g., at transmission and reception); (e) the rotational axis of the catheter; and (f) an offset of the transducer elements relative to an apex (e.g., a left-most or center point on catheter rotation axis) (e.g., as disclosed in Eq. (15)).

In one embodiment, generating an image of the medium as a function of at least the plurality of reflected signals includes: an offset of the transducer array elements relative to the imaging apex in 2D; and an angle of the plane wave. In one embodiment, the method 2500 further comprising: reconstructing a rotation corrected compounded image from one or more individual 2D sub-images as a function of: a rotational angle of the catheter for each sub-image (e.g., as disclosed in Eq. (18)).

In one embodiment, a distance between the reception angular position for the respective reflected signal and the transmission angular position of the acoustic transducers for the respective reflected signal is a function of: (a) a rotational speed of the catheter; (b) a target imaging focal depth (e.g., 40 mm deep tissue), (c) a speed of sound in the medium (e.g. 1540 m/s), (d) a transmit pulsing rate of the imaging console (i.e. pulse repetition frequency, PRF), and (e) a target 3D imaging rate (e.g. 20 Hz). Thereby, the target PRF is limited by the target penetration focal depth $d_a$ and the speed of sound c through $$f_{2D,max} = \frac{c}{2d_a}, \quad (28)$$

where the rotational speed of the catheter $\omega=2\pi f_{3D}$ is determined by the target 3D imaging rate $f_{3D}$, the distance between angular positions is determined by Eq. (1) with the angle between planes $\phi$ defined by Eq (2).

In one embodiment, the number of reflected signals may be determined as a function of a beam shape profile of the transmission wave signal (e.g., as shown in FIG. 16).

In one embodiment, the generated image may represent an imaging depth as a function of: (a) a transmit pulsing rate of the imaging console (i.e., pulse repetition frequency), (b) a rotational speed of the catheter, (c) a speed of sound in the target medium, (d) a number of plane wave transmits used for imaging (e.g., sub-image or full image) (e.g., as described in Eqs. (3) and (28)).

In one embodiment, the catheter is rotated at a speed as a function of: (a) a target volumetric imaging rate required to image the area of observation (e.g., at least 20 Hz required for artifact-free imaging of the heart), (b) a target volumetric spatial resolution (e.g., 0.25 mm) within the area of observation, (c) an imaging depth (e.g., 40 mm), (d) a transmit pulsing rate of the imaging console (i.e., pulse repetition frequency) (e.g., as described in Eqs. (1)-(2)).

In one embodiment, each of the plurality of reflected signals is received by the array of acoustic transducers at a reception angular position that is different than the transmission angular position of the corresponding transmitted incident acoustic wave signal.

In one embodiment, generating an image of the medium as a function of at least the plurality of reflected signals includes: a beam width profile of the plane wave (e.g., 3D beam shape defined by pressure field of acoustic wave) (e.g., as shown in FIG. 16).

Referring to FIGS. 26A-26F, there is shown a flow chart in accordance with an exemplary embodiment of the present invention. The method 2600 for ultrasound imaging may use an imaging system including (i) a catheter (e.g., catheter 1301) comprising a proximal end and a distal end, the distal end of the catheter comprising a catheter tip (e.g., catheter tip 1302), the catheter tip comprising an ultrasound transducer array (e.g., array 1314) enclosed within an acoustic housing and extending along a longitudinal axis of the catheter, wherein the distal end of the catheter is configured to be inserted into and guided to a site of a procedure in a medium, and wherein the ultrasound transducer array is rotatable within the acoustic housing while transmitting ultrasound pulses and receiving ultrasound echoes from the surrounding medium, and (ii) a controller (e.g., console 402) communicatively coupled with the catheter.

The method 2600 may comprise, before an ablation procedure, circumferentially rotating 2602 the catheter including the array of acoustic transducers about a longitudinal axis (e.g., axis x of FIG. 13C) of the catheter.

In one embodiment, while circumferentially rotating 2602 the catheter: transmitting 2604, by an array of acoustic transducers, a plurality of pre-ablation incident acoustic wave signals (e.g., planewaves associated pre-ablation acquisition 1902) representative of angled plane waves in an area of observation of the medium.

In one embodiment, receiving 2606, by an array of acoustic transducers, a plurality of pre-ablation reflected signals (e.g., pre ablation acquisition 1902), wherein each of the plurality of pre-ablation reflected signals corresponds to one of the plurality of pre-ablation incident acoustic wave signals reflected by the medium, wherein the plurality of pre-ablation reflected signals includes raw radio-frequency (i.e., directly after analog to digital conversion (minimal processing)) data represented in time domain.

In one embodiment, after the ablation procedure, circumferentially rotating the catheter including the array of acoustic transducers about a longitudinal axis of the catheter. In one embodiment, while circumferentially rotating the catheter: transmitting 2608, by an array of acoustic transducers, a plurality of post-ablation incident acoustic wave signals (e.g., planewaves associated post ablation acquisition 1900) representative of angled plane waves in an area of observation of the medium.

In one embodiment, receiving 2610, by an array of acoustic transducers, a plurality of post-ablation reflected signals (e.g., post ablation acquisition 1900), wherein each of the plurality of post-ablation reflected signals corresponds to one of the plurality of post-ablation incident acoustic wave signals reflected by the medium, wherein the plurality of post-ablation reflected signals includes raw radio-frequency data represented in a time domain.

In one embodiment, generating 2612 an image (e.g., 2D or 3D) of the medium, including: for each pixel of the image: identifying 2614 a portion of the pre-ablation reflected signals that corresponds to the respective pixel and transforming the portion of the pre-ablation reflected signal from a time domain representation to a frequency domain representation (e.g., as shown in FIG. 18).

In one embodiment, identifying 2616 a portion of the post-ablation reflected signals that corresponds to the respective pixel and transforming the portion of the post-ablation reflected signal from a time domain representation to a frequency domain representation (e.g., as shown in FIG. 18). In one embodiment, generating 2618 a lesion-spectral-change value by comparing the portion of the pre-ablation reflected signals in the frequency domain to the portion of the post-ablation reflected signals in the frequency domain (e.g., as shown in FIG. 19).

In one embodiment, comparing the portion of the pre-ablation reflected signals (e.g., graph of pre and post spectra 1804 and 1806 as shown in FIG. 1320 18), in the frequency domain to the portion of the post-ablation reflected signals in the frequency domain includes: calculating a difference (e.g., Eq. (23)) between the portion of the pre-ablation reflected signals in the frequency domain to the portion of the post-ablation reflected signals in the frequency domain (e.g., graph or pre and post spectra 1804 and 1806 as shown in FIG. 18).

In one embodiment, comparing the portion of the pre-ablation reflected signals in the frequency domain to the portion of the post-ablation reflected signals in the frequency domain includes: transforming the pre ablation signals and the post ablation reflected signals into the frequency domain by power spectrum estimations using the Fast Fourier Transform (e.g. before and after ablation for exemplary target points, 1804 and 1806, is calculated using Fast Fourier Transform).

In one embodiment, the generation of an image (e.g., 2D or 3D) of lesion-spectral-change values comprises of a plurality of individual images of lesion-spectral-change values (e.g., lesion maps for each transmit angle αi 2002) reconstructed into a rotation correct compounded image (e.g., compounded lesion map 2004) of lesion-spectral change values as a function of: a) a rotational angle of the catheter for each sub-image (e.g., rotational delays for each transmit, 2006) b) a plane wave angle for each sub-image (e.g., plane wave angle ø of planewave group 1310), and c) a distance of the transducer elements to the catheter rotation axis 1320 (e.g., as shown in FIG. 13).

In one embodiment, comparing the portion of the pre-ablation reflected signals in the frequency domain to the portion of the post-ablation reflected signals in the frequency domain includes (e.g., equation 23):

$$L(x_k, y_k, \alpha_i) = \sum_{f=0}^{\frac{fs}{2}} \frac{10 \log_{10}(S_{pre}(f, x_k, y_k, \alpha_i))}{10 \log_{10}(S_{post}(f, x_k, y_k, \alpha_i))}$$

The method 2600 may further comprise, correlating 2620 a lesion-spectral-change mapping (e.g., reconstructed lesion map 1808) to a histopathological acquisition (e.g., histology data shown in FIG. 23) of the medium. In one embodiment, this may include: creating 2622 a lesion-spectral change mapping. In one embodiment, preservation 2624 of the medium using agents used in histopathology; staining 2626 (e.g., stained histology shown in FIG. 24) the target medium with agents displaying the tissue microstructure of lesions (e.g., annotated tissue microstructure shown in FIG. 24) in the medium and digitalizing sectional images of the medium. In one embodiment, reconstructing 2628 3D histopathological volume (e.g., 3D histology volume shown in FIG. 24) from a plurality of sectional histopathology images. In one embodiment, registering 2630 the 3D histopathological volume to the lesion-spectral-change mapping data. In one embodiment, calibrating 2632 the lesion-spectral-change map to the 2D and 3D images of histopathological microstructure (e.g., correlated histology and imaging data shown in FIG. 24).

The method 2600 may further comprise, displaying 2634 a lesion-spectral-change mapping (e.g., reconstructed lesion map 1808) on a display communicatively coupled to the controller. The method 2600 may further comprise, determining 2636 whether the lesion-spectral-change value meets lesion change criteria and in accordance with determining 2636 that the lesion-spectral-change value meets lesion change criteria, generating 2638 a lesion performance success message. In one embodiment, in accordance with determining that the lesion-spectral-change value does not meet lesion change criteria, forego generating 2640 a lesion performance success message.

Figure 27:
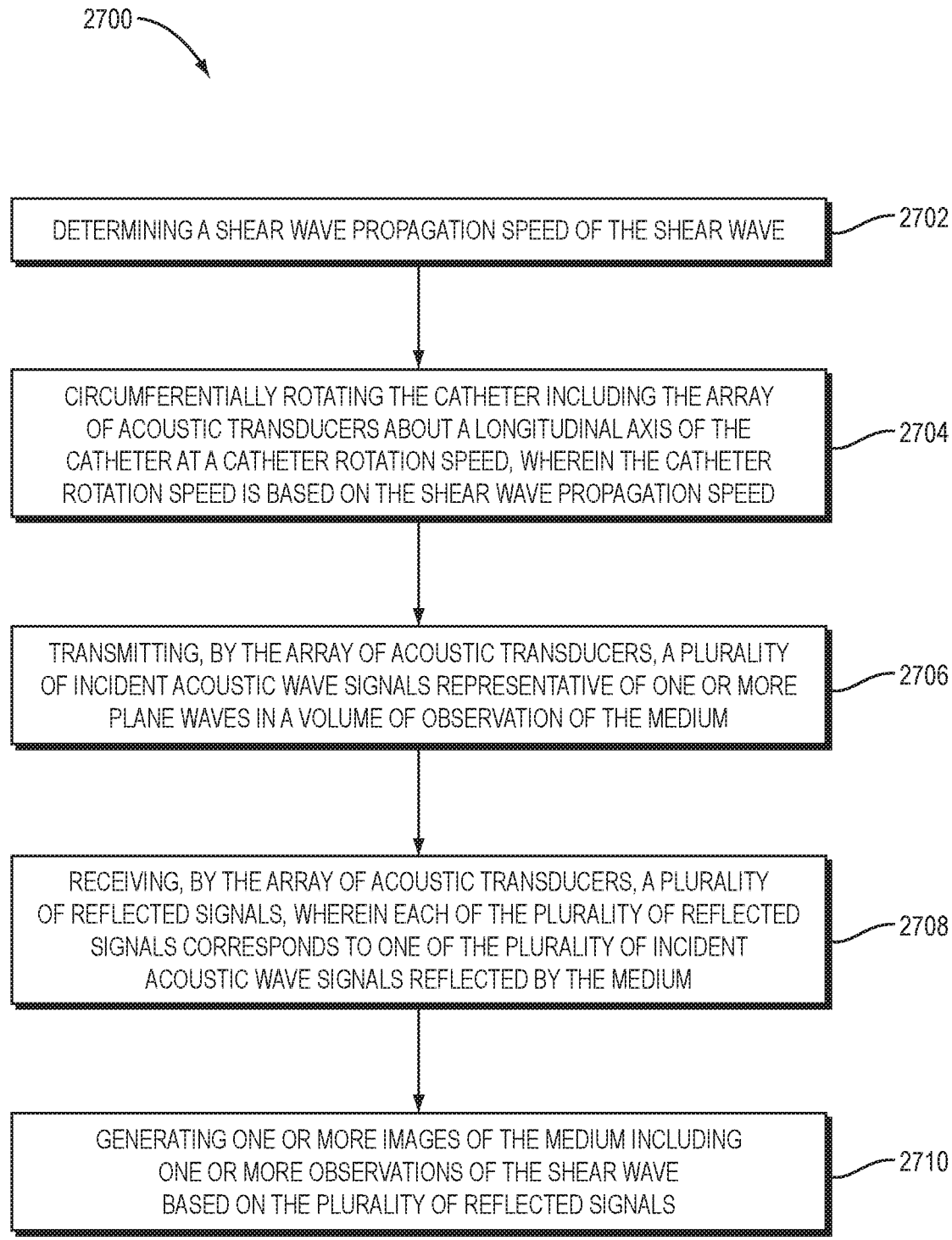
FIG. 27 is an exemplary illustration of a flow chart illustrating one embodiment of the present invention.

Referring to FIG. 27, there is shown a flow chart in accordance with an exemplary embodiment of the present invention. The method 2700 for ultrasound imaging of a medium may include a shear wave using an imaging system including (i) a catheter (e.g., catheter 1301) comprising a proximal end and a distal end, the distal end of the catheter comprising a catheter tip (e.g., catheter tip 1302), the catheter tip comprising an ultrasound transducer array (e.g., array 1314) enclosed within an acoustic housing and extending along a longitudinal axis of the catheter, wherein the distal end of the catheter is configured to be inserted into and guided to a site of a procedure in a medium, and wherein the ultrasound transducer array is rotatable within the acoustic housing while transmitting ultrasound pulses and receiving ultrasound echoes from the surrounding medium, and (ii) a controller (e.g., console 402) communicatively coupled with the catheter.

The method 2700 comprising: determining 2702 a shear wave propagation speed (e.g., $\delta_{SW}$ in equation 27) of the shear wave. In some embodiments, shearwave propagation speed is given by scientific evaluations, and the tuning of shear waves can be adopted based on estimated shear waves speeds to be observed in cardiac tissue. FIG. 22 shows exemplary shear wave speeds, where higher shear wave speed corresponds to an increase in tissue stiffness. As one example, the average shear wave speed in unablated (i.e. healthy) atrial tissue can be in the range from 1.0 to $$1.5 \frac{m}{s},$$

and increases to shear wave speeds of 2.3 to $$4.3 \frac{m}{s}$$

after tissue ablation (corresponding to higher tissue stiffness of ablated versus healthy tissue).

The method 2700 comprising: circumferentially rotating 2704 the catheter including the array of acoustic transducers about a longitudinal axis of the catheter at a catheter rotation speed (e.g., catheter rotation speed 2102), wherein the catheter rotation speed is based on the shear wave propagation speed.

In one embodiment, the method 2700 comprising while circumferentially rotating the catheter: transmitting 2706, by the array of acoustic transducers, a plurality of incident acoustic wave signals representative of one or more plane waves in a volume of observation of the medium (e.g., as shown in FIG. 21).

In one embodiment, the method 2700 comprising receiving 2708, by the array of acoustic transducers, a plurality of reflected signals, wherein each of the plurality of reflected signals corresponds to one of the plurality of incident acoustic wave signals reflected by the medium (e.g., as shown in FIG. 21).

In one embodiment, the method 2700 comprising generating 2710 one or more images of the medium including one or more observations of the shear wave based on the plurality of reflected signals.

In one embodiment, the catheter rotation speed is at least the shear wave propagation speed (e.g., shear wave speed ranges as shown in FIG. 22).

In one embodiment, the catheter rotation speed is static relative to the shear wave propagation speed (e.g., static may refer to catheter rotation speed being relatively the same through an entire rotation of the catheter within a tolerance of 1 revolution per minute or 0.1 revolutions per minute.)

In one embodiment, a difference between the catheter rotation speed and the shear wave propagation speed is less than 1 revolution per minute.

In one embodiment, the catheter rotation speed is in the range of 110 revolutions per minute to 4900 revolutions per minute (e.g., shear wave speed minimum to maximum values shown in equivalent rotational speed in RPM table of FIG. 22).

In one embodiment, the catheter rotation speed is in the range of 600 revolutions per minute to 2400 revolutions per minute.

In one embodiment, the catheter rotation speed is in the range of 900 revolutions per minute to 1500 revolutions per minute.

In one embodiment, transmitting, by the array of acoustic transducers, a plurality of incident acoustic wave signals includes: transmitting, by the array of acoustic transducers at a set of different transmission angular positions, the plurality of incident acoustic wave signals representative of one or more plane waves in a volume of observation of the medium (e.g., as shown in FIG. 15).

In one embodiment, receiving, by the array of acoustic transducers, a plurality of reflected signals includes: receiving, by the array of acoustic transducers at a set of different reception angular positions, the plurality of reflected signals, wherein each of the plurality of reflected signals corresponds to one of the plurality of incident acoustic wave signals reflected by the medium, wherein at least one of the plurality of reflected signals is received by the array of acoustic transducers at a reception angular position that is different than the transmission angular position of the corresponding transmitted incident acoustic wave signal (e.g., as shown in FIG. 15).

In one embodiment, generating the image of the medium includes: generating the image as a function of: for at least one of the plurality of reflected signals: (a) the transmission angular position of each of the acoustic transducers for the incident acoustic wave signal that corresponds to the respective reflected signal and (b) the reception angular position of each of the acoustic transducers for the respective reflected signal, wherein the reception angular position of the acoustic transducers for the respective reflected signal is different than the transmission angular position of the acoustic transducers for the respective reflected signal (e.g., as disclosed in Eq. (18)).

In one embodiment, the catheter rotation speed is a function of: (a) the shear wave propagation speed, (e.g., $\delta_{SW}$ in Eq. (27)) (b) a distance between the shear wave and the array of acoustic transducers (z in Eq. (27)), and (c) an angle of the catheter between subsequent transmissions by the array of acoustic transducers (e.g., $\theta$ in Eq. (27)).

While particular embodiments of the present invention have been shown and described, it will be obvious to those skilled in the relevant arts that changes and modifications may be made without departing from the invention in its broader aspects. Therefore, the aim in the appended claims is to cover all such changes and modifications that fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The terminology used herein is for the purpose of describing particular embodiments only and is not intended to limit the invention. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly-understood by one of ordinary skill in the art to which this invention belongs. Furthermore, terms, such as those defined in commonly-used dictionaries, should be interpreted as having a meaning that is consistent with their meaning in the context of the relevant art, and will not be interpreted in an idealized or overly formal sense unless expressly so defined herein.

What is claimed is:

1. An imaging system comprising a console that is configured to be operably associated with a catheter-based ultrasound imaging device that is configured to operate in a wave imaging mode causing an ultrasound transducer array of the catheter-based ultrasound imaging device to carry out multiple wave transmit-receive cycles, each cycle comprising transmission of a wave front to, and receipt of echoes of the wave front from, surrounding intravascular tissue, wherein the ultrasound transducer array comprises a plurality of acoustic transducers set at different transmission angular positions configured to transmit a plurality of incident acoustic wave signals representative of one or more waves in a volume of observation of the surrounding intravascular tissue and the ultrasound transducer array further comprises the plurality of acoustic transducers set at different reception angular positions configured to receive a plurality of reflected signals, wherein each of the plurality of reflected signals corresponds to one of the plurality of incident acoustic wave signals reflected by the intravascular tissue, wherein at least one of the plurality of reflected signals is received by the array of acoustic transducers at a reception angular position that is different than the transmission angular position of the corresponding transmitted incident acoustic wave signal, the console comprising a processor configured to:

control and cause continuous full rotation of the ultrasound transducer array about a longitudinal axis of the catheter;

control and cause transmission of multiple wave transmit cycles from the ultrasound transducer array to, and receipt of multiple wave receive cycles from, the surrounding intravascular tissue;

receive wave data from the catheter-based ultrasound imaging device, wherein the wave data is associated with one or more wave transmit-receive cycles carried out with respect to surrounding intravascular tissue via the catheter-based ultrasound imaging device and the wave data comprises at least one of plane wave data and diverging wave data; and reconstruct one or more images from the wave data to generate a full circumferential, 360-degree view of intravascular tissue, wherein at least one image of the intravascular tissue is reconstructed as a function of at least:

the plurality of reflected signals, and, for at least one of the respective reflected signals:

the transmission angular position of each of the plurality of acoustic transducers for the incident acoustic wave signal that corresponds to the respective reflected signal; and the reception angular position of each of the plurality of acoustic transducers for the respective reflected signal, wherein the reception angular position of the acoustic transducers for the respective reflected signal is different than the transmission angular position of the acoustic transducers for the respective reflected signal.

2. The system of claim 1, wherein the processor of the console is further configured to:

process the reflected signal data using a compounding algorithm and reconstruct at least one of a two-, three-, or four-dimensional image from reflected signal data; and output, via a display, the reconstructed two-, three-, or four-dimensional image to an operator depicting visualization of the intravascular tissue.

3. The system of claim 1, wherein the ultrasound transducer array comprises a 64-channel array design allowing ultrafast wave imaging, wherein the wave imaging mode comprises capturing plane wave reflected signal data at a rate of at least 10 kHz.

4. The system of claim 1, wherein the ultrasound transducer array comprises a cylindrical array of ultrasound transducer elements.

5. The system of claim 1, wherein the ultrasound transducer array comprises a linear array of ultrasound transducer elements.

6. The system of claim 1, wherein the ultrasound transducer array comprises a 2D array of transducer elements.

7. The system of claim 1, wherein reconstructing an image of the intravascular tissue as a function of at least the plurality of reflected signals comprises, for each of the respective reflected signals:

an angle of the wave;

a rotational angle of the catheter;

the rotational axis of the catheter; and an offset of the transducer elements relative to an apex.

8. The system of claim 1, wherein reconstructing an image of the intravascular tissue as a function of at least the plurality of reflected signals comprises:

an offset of the transducer array elements relative to the imaging apex in two-dimensional form; and an angle of the wave;

wherein the console is configured to reconstruct a rotation corrected compounded image from one or more individual two-dimensional sub-images as a function of a rotational angle of the catheter for each sub-image.

* * * * *